United States Patent
Choi et al.

(10) Patent No.: US 10,485,691 B2
(45) Date of Patent: Nov. 26, 2019

(54) INDEPENDENTLY ADJUSTABLE SUPPORT SYSTEM

(71) Applicant: PRS Medical Technologies, Inc., Atherton, CA (US)

(72) Inventors: George Y. Choi, Atherton, CA (US); Nikhil Bhat, Fremont, CA (US); Allen J. Li, San Francisco, CA (US); Trevor M. Hannon, Hayward, CA (US); Robert A. Brommer, Fremont, CA (US)

(73) Assignee: PRS Medical Technologies, Inc., Menlo Park, CA (US)

( * ) Notice: Subject to any disclaimer, the term of this patent is extended or adjusted under 35 U.S.C. 154(b) by 405 days.

(21) Appl. No.: 13/784,035

(22) Filed: Mar. 4, 2013

(65) Prior Publication Data
US 2013/0180531 A1    Jul. 18, 2013

Related U.S. Application Data

(63) Continuation-in-part of application No. 13/760,482, filed on Feb. 6, 2013, now abandoned, which is a
(Continued)

(51) Int. Cl.
*A47C 7/02* (2006.01)
*A61G 7/057* (2006.01)
(Continued)

(52) U.S. Cl.
CPC ............... *A61F 5/34* (2013.01); *A61F 5/32* (2013.01); *A61G 5/1043* (2013.01);
(Continued)

(58) Field of Classification Search
CPC ...... A61F 5/00; A61F 5/01; A61F 5/30; A61F 5/32; A61F 5/34; A61F 13/00;
(Continued)

(56) References Cited

U.S. PATENT DOCUMENTS

| 3,748,669 | A |   | 7/1973 | Warner |
| 4,073,021 | A | * | 2/1978 | Carlisle ............... A47C 27/081 5/654 |

(Continued)

FOREIGN PATENT DOCUMENTS

| WO | WO 2001/089433 | 11/2001 |
| WO | WO 2002/074205 | 9/2002 |

(Continued)

OTHER PUBLICATIONS

U.S. Appl. No. 13/784,133, filed Mar. 4, 2013.
(Continued)

*Primary Examiner* — Kari K Rodriguez
*Assistant Examiner* — Camtu T Nguyen
(74) *Attorney, Agent, or Firm* — Levine Bagade Han LLP

(57) ABSTRACT

Apparatus and methods for adjusting a support to a body are described in which a portable support assembly may be worn or used by a bed-stricken or wheel-chair restricted individual around particular regions of the body where pressure ulcers tend to form. The portable support assembly may generally include adjustable supports which conform the assembly to the patient's body and which also help to distribute one or more fluid pad assemblies relative to the body. The support assembly may be incorporated into a design for a wheelchair or a bed.

17 Claims, 35 Drawing Sheets

Related U.S. Application Data continuation-in-part of application No. 13/693,691, filed on Dec. 4, 2012, now Pat. No. 9,326,905, which is a continuation-in-part of application No. 13/683,198, filed on Nov. 21, 2012, now Pat. No. 9,339,407, which is a continuation-in-part of application No. 13/407,628, filed on Feb. 28, 2012, now Pat. No. 8,656,919, which is a continuation-in-part of application No. 13/189,320, filed on Jul. 22, 2011, now Pat. No. 8,776,798.

(51) Int. Cl.

| | | |
|---|---|---|
| *A61F 5/30* | (2006.01) | |
| *A61F 5/32* | (2006.01) | |
| *A61F 5/34* | (2006.01) | |
| *A61G 5/10* | (2006.01) | |
| *A61G 7/05* | (2006.01) | |
| *A61G 7/075* | (2006.01) | |

(52) U.S. Cl.
CPC ..... *A61G 7/05769* (2013.01); *A61G 7/05776* (2013.01); *A61G 7/0525* (2013.01); *A61G 7/0573* (2013.01); *A61G 7/075* (2013.01); *A61G 2203/34* (2013.01)

(58) Field of Classification Search
CPC ...... A61F 13/06; A61F 13/064; A61F 13/069; A61F 2007/0215; A61F 2007/0217; A61F 2007/0219; A61F 2007/022; A61F 2007/023; A61F 2007/0222; A61F 2007/0236; A61G 7/00; A61G 7/002; A61G 7/015; A61G 5/1043; A61G 7/05769; A61G 7/05776; A61G 7/0525; A61G 5/0573; A61G 5/075; A61G 7/057; A61G 7/001; A61G 5/1045; A47C 7/02; A47C 7/021; A47C 7/0213; A47C 21/04
USPC ........ 128/846, 869, 888, 889; 602/5, 13, 19, 602/20
See application file for complete search history.

(56) References Cited

U.S. PATENT DOCUMENTS

| | | | |
|---|---|---|---|
| 4,175,548 A | | 11/1979 | Henry |
| 4,370,769 A | | 2/1983 | Herzig et al. |
| 4,389,742 A | * | 6/1983 | DeWitt ................ A47C 7/021 5/654 |
| 4,405,129 A | * | 9/1983 | Stuckey ............ A63B 21/0085 482/112 |
| 4,483,030 A | | 11/1984 | Flick et al. |
| 4,534,078 A | | 8/1985 | Viesturs et al. |
| 4,559,933 A | | 12/1985 | Batard et al. |
| 4,617,690 A | | 10/1986 | Grebe |
| 4,622,957 A | | 11/1986 | Curlee |
| 4,673,605 A | | 6/1987 | Sias et al. |
| 4,682,588 A | | 7/1987 | Curlee |
| 4,726,624 A | | 2/1988 | Jay |
| 4,836,194 A | | 6/1989 | Sebastian et al. |
| 4,934,002 A | | 6/1990 | Watanabe |
| 5,040,525 A | | 8/1991 | Georgijevic |
| 5,122,111 A | | 6/1992 | Sebastian et al. |
| 5,144,705 A | | 9/1992 | Rogers |
| 5,152,023 A | | 10/1992 | Graebe |
| 5,303,436 A | | 4/1994 | Dinsmoor, III et al. |
| 5,388,292 A | | 2/1995 | Stinson et al. |
| 5,421,874 A | | 6/1995 | Pearce |
| 5,489,259 A | | 2/1996 | Jacobs et al. |
| 5,671,552 A | | 9/1997 | Pettibone et al. |
| 5,771,514 A | * | 6/1998 | Wilhoit ............ A47G 9/1027 5/421 |
| 5,794,289 A | * | 8/1998 | Wortman ............ A61G 7/001 5/423 |
| 5,829,081 A | * | 11/1998 | Pearce ................ A47C 27/083 5/654 |
| 5,843,008 A | | 12/1998 | Gerhard |
| 6,012,188 A | | 1/2000 | Daniels et al. |
| 6,020,055 A | | 2/2000 | Pearce |
| 6,026,527 A | | 2/2000 | Pearce |
| 6,047,425 A | | 4/2000 | Khazaal |
| 6,065,166 A | | 5/2000 | Sharrock et al. |
| 6,197,099 B1 | | 3/2001 | Pearce |
| 6,216,299 B1 | | 4/2001 | Kohlman |
| 6,226,820 B1 | * | 5/2001 | Navarro ............ A47C 27/085 5/654 |
| 6,560,803 B2 | | 5/2003 | Zur |
| 6,640,347 B2 | * | 11/2003 | Fukasawa ........... A63B 33/002 2/428 |
| 6,640,367 B2 | | 11/2003 | Hsia |
| 6,813,790 B2 | | 11/2004 | Flick et al. |
| 6,874,185 B1 | | 4/2005 | Phillips et al. |
| 6,896,662 B2 | | 5/2005 | Heffez |
| 7,060,213 B2 | | 6/2006 | Pearce |
| 7,063,677 B1 | | 6/2006 | Daggett |
| 7,141,032 B2 | | 11/2006 | Flam et al. |
| 7,216,388 B2 | | 5/2007 | Bieganek et al. |
| 7,254,852 B2 | | 8/2007 | Martin |
| 8,216,169 B2 | * | 7/2012 | Koby .................... A61F 5/0118 128/846 |
| 8,656,919 B2 | | 2/2014 | Bhat et al. |
| 8,776,798 B2 | | 7/2014 | Choi et al. |
| 2003/0041379 A1 | | 3/2003 | Habboub et al. |
| 2003/0120191 A1 | | 6/2003 | Clement |
| 2005/0177952 A1 | | 8/2005 | Wilkinson et al. |
| 2005/0262639 A1 | | 12/2005 | Butler |
| 2006/0010607 A1 | | 1/2006 | Schneider |
| 2007/0063368 A1 | | 3/2007 | Schindler |
| 2008/0249449 A1 | | 10/2008 | Brown et al. |
| 2009/0070939 A1 | | 3/2009 | Hann |
| 2009/0095566 A1 | | 4/2009 | Leong et al. |
| 2009/0194115 A1 | | 8/2009 | Squitieri |
| 2009/0254015 A1 | | 10/2009 | Segal et al. |
| 2010/0152821 A1 | | 6/2010 | Rein et al. |
| 2010/0229308 A1 | | 9/2010 | Pearce et al. |
| 2010/0242182 A1 | | 9/2010 | Chuang et al. |
| 2011/0099714 A1 | | 5/2011 | Svoboda |
| 2011/0126356 A1 | | 6/2011 | Steppat et al. |
| 2011/0239372 A1 | * | 10/2011 | Bhat et al. ........................ 5/690 |
| 2012/0311787 A1 | | 12/2012 | Purdy et al. |
| 2013/0019873 A1 | | 1/2013 | Choi et al. |
| 2013/0019881 A1 | | 1/2013 | Bhat et al. |
| 2013/0092175 A1 | | 4/2013 | Bhat et al. |
| 2013/0112213 A1 | | 5/2013 | Bhat et al. |
| 2013/0174855 A1 | | 7/2013 | Choi et al. |
| 2013/0174856 A1 | | 7/2013 | Choi et al. |
| 2013/0174859 A1 | | 7/2013 | Bhat et al. |
| 2013/0180530 A1 | | 7/2013 | Choi et al. |
| 2013/0255699 A1 | | 10/2013 | Squitieri |

FOREIGN PATENT DOCUMENTS

| | | |
|---|---|---|
| WO | WO 2007/047379 | 4/2007 |
| WO | WO 2010/017667 | 2/2010 |
| WO | WO 2013/016241 | 1/2013 |
| WO | WO 2014/081521 | 5/2014 |

OTHER PUBLICATIONS

U.S. Appl. No. 13/784,215, filed Mar. 4, 2013.
U.S. Appl. No. 13/784,260, filed Mar. 4, 2013.
U.S. Appl. No. 13/945,684, filed Jul. 18, 2013.
U.S. Appl. No. 13/189,320, filed Jul. 22, 2011.
U.S. Appl. No. 13/407,628, filed Feb. 28, 2012.
U.S. Appl. No. 13/683,198, filed Nov. 21, 2012.
U.S. Appl. No. 13/693,691, filed Dec. 4, 2012.
U.S. Appl. No. 13/760,482, filed Feb. 6, 2013.

* cited by examiner

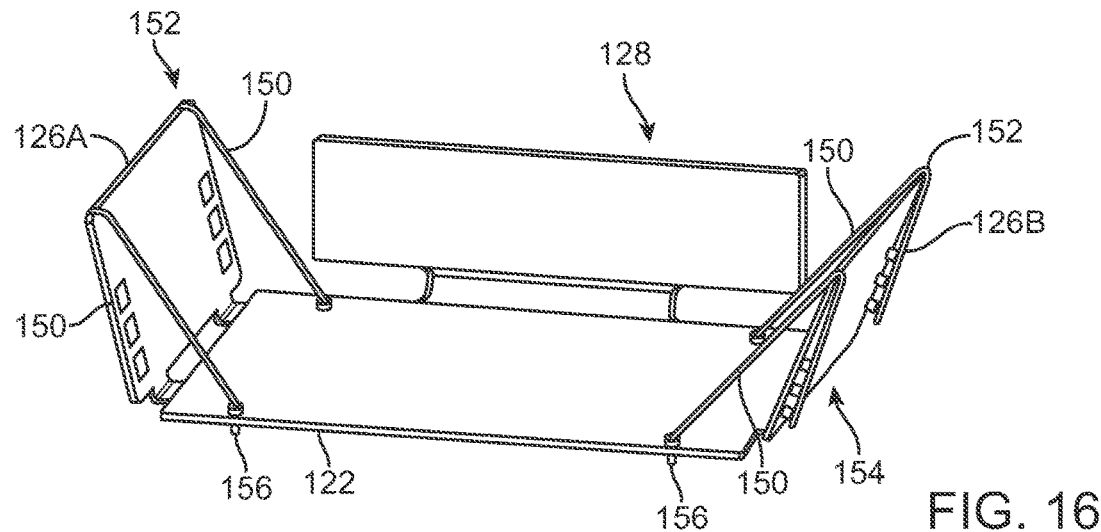
FIG. 16
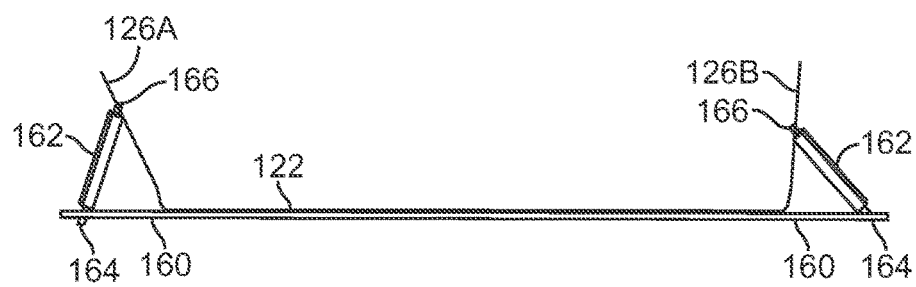
FIG. 17A
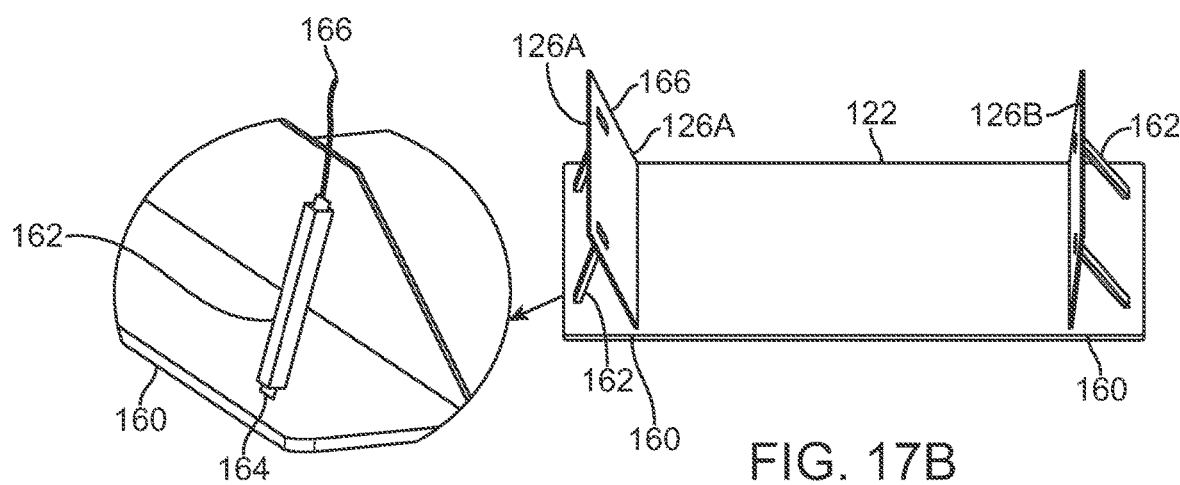
FIG. 17B
FIG. 17C

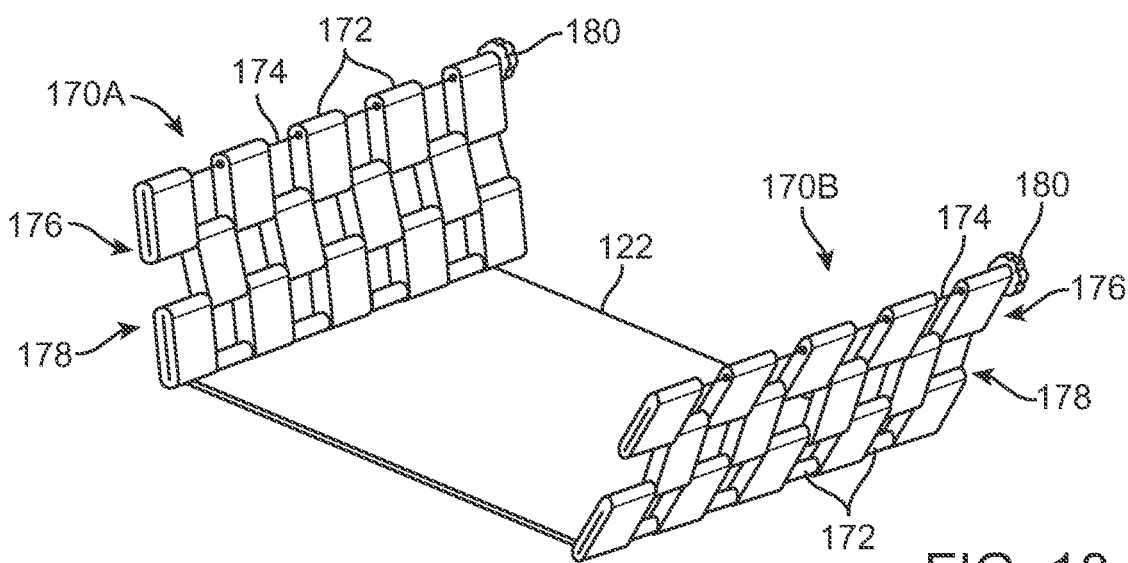
FIG. 18
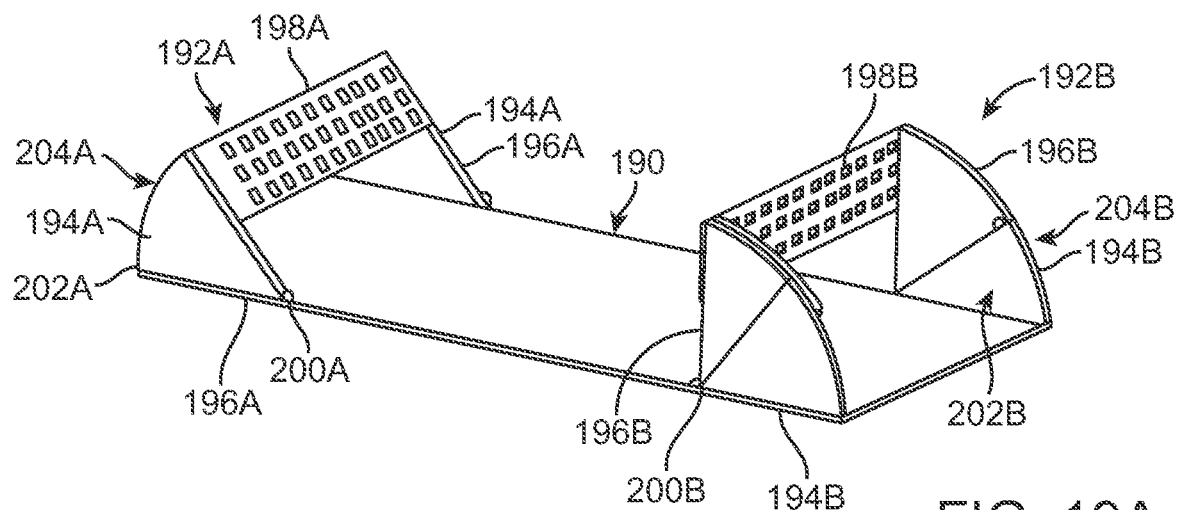
FIG. 19A
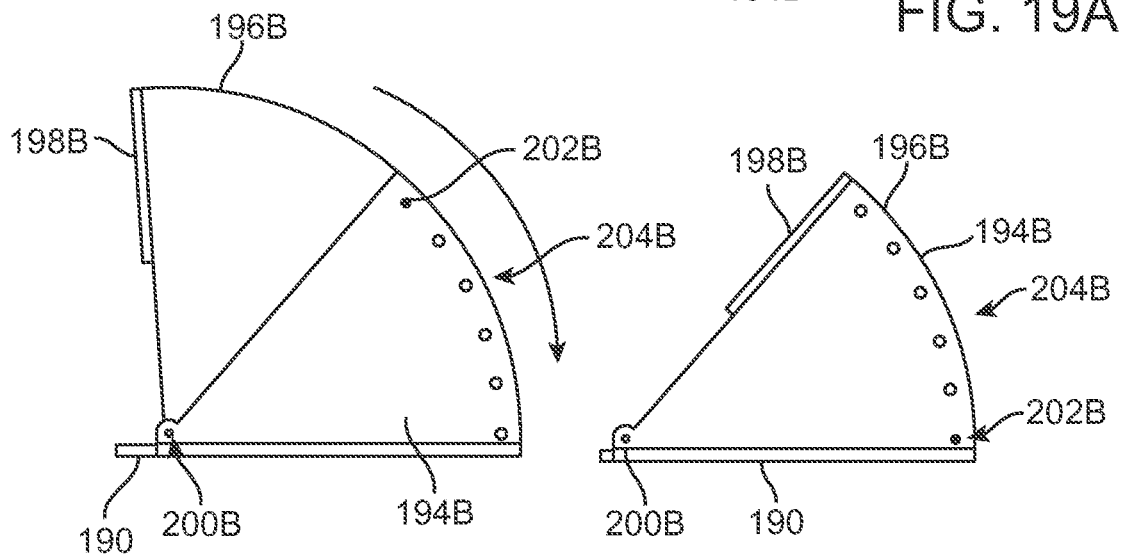
FIG. 19B
FIG. 19C

INDEPENDENTLY ADJUSTABLE SUPPORT SYSTEM

This application is a continuation-in-part of U.S. application Ser. No. 13/760,482 filed Feb. 6, 2013, which is a continuation-in-part of U.S. application Ser. No. 13/693,691 filed Dec. 4, 2012, which is a continuation-in-part of U.S. application Ser. No. 13/683,198 filed Nov. 21, 2012, which is a continuation-in-part of U.S. application Ser. No. 13/407,628 filed Feb. 28, 2012, which is a continuation-in-part of U.S. application Ser. No. 13/189,320 filed Jul. 22, 2011, each of which is incorporated herein by reference in its entirety.

FIELD OF THE INVENTION

The present invention relates to devices and methods for preventing and treating pressure ulcers. More particularly, the present invention relates to devices and methods for preventing and treating pressure ulcers with cushioning devices which are integrated into surfaces on which an individual sits, lies, or stands or are adapted to be applied to such surfaces and easily conformed to various regions of the patient's body by utilizing individual cushioning pods which are supported within an inner fluid pad as well as an outer fluid pad.

BACKGROUND OF THE INVENTION

Individuals who are forced to sit or lie down for extended periods of time typically experience tissue necrosis over localized regions of their body known as decubitus ulcers or pressure sores. In 2009 more than a million people in acute care centers were affected with pressure ulcers. In addition to acute care centers, more than 500,000 people in long-term care centers are diagnosed with pressure ulcers every year. Pressure ulcers generally occur at locations of the body where the bony prominence is high and the underlying skin breaks down when constant pressure is placed against the skin. Blood circulation is inhibited or prevented in these localized areas and can even occur when the patient has been lying against or upon cushioning devices. Examples of areas of the body where pressure sores typically occur include the sacrum, greater trochanter, ischial tuberosity, malleolus, heel, etc. When pressure ulcers form, they can lead to extensive stays in the hospital or even to amputation.

Conventional cushioning devices generally utilize flexible materials such as foam or springs which allow for the cushion to deform and conform to the patient's body. While the cushioning device attempts to redistribute the loading from localized regions of the patient's body to a larger area over the rest of the body, such devices typically bottom out such that the patient's body contacts the underlying platform and nonetheless localizes the pressure onto the body.

Other cushioning devices have utilized fluid-filled cushions which consist of large single bladders or compartmentalized fluid or gas-filled bladders which inhibit fluid contained within the bladders from flowing laterally. In a fluid filled bladder disposed on a contoured seat, the fluid filled bladder typically bottoms out in one or more areas when supporting a patient's body weight. The places where the bladder bottoms out are sources of high localized pressure. Thus, such an assembly does not distribute pressure evenly across the portions of the anatomy in contact with the bladder. The amount of water that is used in such a bladder can be increased such that bottoming out does not occur. However, this design sacrifices stability. Additionally, since such cushions are typically designed to accommodate a wide range of patient populations, patients who are not as heavy as the maximum for which the cushion was designed for will suffer even more lack of stability than would be needed.

Another problem with simply increasing the amount of fluid to prevent bottoming out is that this requires significant volume of fluid beneath the patient and/or require specialized bedding. Additionally, many fluid filled membranes are too thick to provide adequate pressure relief because the hammocking that occurs in the regions of high protrusions. Thus, the suspension of the patient's body typically results in significantly non-uniform pressure application, with higher pressures being applied to protruding portions of the patient's body due to lack of adequate conformance of the bladder material to the patient's body.

Yet other cushioning devices utilize segmented bladders in an attempt to isolate individual bladders from one another. Yet such segmented cushions may fail to allow for the cushion to fully conform to the patient's body as fluid between each of the segmented cushions is prevented.

Accordingly, there exists a need for a cushioning device which may conform to regions of the patient's body to prevent decubitis ulcers in a manner which is more cost efficient, convenient, and effective.

BRIEF SUMMARY OF THE INVENTION

A portable support assembly may be integrated into a piece of furniture on which an individual sits, lies, or stands for an extended period of time to prevent the formation of pressure ulcers. Such a portable support assembly may be configured to conform to particular regions of the body where pressure ulcers tend to form, e.g., sacrum, trochanter, ischium, as well as any other region of the body where support is desired. The portable support assembly may be formed into an elongated shape to be wrapped entirely around the patient's body. e.g., around the hips or lower back, or a portion of the body, e.g., around the ankles or feet. For example, the support assembly may be placed upon a bed, wheelchair, or platform (or directly integrated into the bed, wheelchair, or platform) upon which the patient is resting.

The support assembly may be configured to be portable such that it may be worn directly over or upon the patient's body independently from the underlying bed or cushion. Accordingly, the patient may utilize the support assembly on any underlying bed or platform. Additionally, while the examples described illustrate portable support assemblies, the support assembly may be integrated into a bed, underlying cushion, and/or mattress pad if so desired and as previously described.

If integrated into a bed, the support assembly may further comprise a mattress, such as a spring mattress, a foam mattress, a low air loss mattress, a segmented air mattress, or a cyclical air pressure mattress. The mattress may include a recess in which the assembly or the outer pad is seated.

Generally, the support assembly may comprise one or more pods positioned adjacent to one another, an inner pad enclosing the one or more pods such that compression of the pods is controlled by the inner pad, an outer pad enclosing the inner pad, and an outer shell attached to the outer pad, wherein the outer shell is sufficiently flexible to be worn upon a portion of a subject's body.

In use, the support assembly may support the desired region of the body by securing a portable support assembly directly to the region of the body to be supported, controlling displacement of one or more pods positioned along the support assembly beneath the region via an inner pad enclosing the one or more pods, and redistributing a pressure load from the one or more pods and inner pad to an outer pad positioned along the support assembly and enclosing the inner pad, wherein the redistributed pressure load is exerted upon the body surrounding the supported region.

One variation of the portable support assembly may generally define a securement area for placement against the region of the body requiring support such as the sacrum. The securement area may generally comprise a central portion with a first conformable portion and/or second conformable portion extending from either side of the central portion. The first and/or second conformable portions may be flexible enough to allow for the portions to be wrapped around or about at least a portion of the patient's body such that the assembly may remain secured to the body even when the patient moves about thereby maintaining the central portion against the supported region of the body.

The central portion may provide the greatest amount of localized support to the patient body by utilizing several fluid layers which are contained one within another to receive the localized loading from the protuberance from the patient's body and distribute the localized load onto the surrounding areas and to further control displacement or inhibit or prevent the bottoming out of the fluid layers. The central portion may thus contain one or more fluid filled individual pods which may be enclosed entirely within an inner fluid pad which envelopes the one or more pods within a secondary layer of fluid. The inner fluid pad may be localized along the central portion. Both the one or more pods and inner fluid pad are then enclosed entirely by a tertiary layer of fluid within an outer fluid pad which may extend over the entire assembly. Each of the fluid layers may be secured to an outer shell which is relatively stiffer than the fluid layers and may restrict or limit the expansion or movement of the fluid pods and/or fluid pads. While the assembly is adjustable to fit a particular patient, the outer pad, in particular, may optionally be filled with the fluid to a variable amount to further ensure that the assembly may be fitted or conformed to the anatomy of a particular patient.

Each of the one or more pods may be separated from one another such that no fluid communication occurs between the pods and/or with the inner pad. Similarly, the inner pad may be separate from the outer pad such that no fluid communication occurs between the two. In other variations, some fluid communication may occur between the inner pad and outer pad so long as the inner pad constrains and prevents the over-compression of the one or more pods to control their displacement and inhibit their bottoming out.

Each of the pods and/or fluid pads may be filled with an incompressible fluid such as water, viscous oil, or some other biocompatible fluid. Yet in other variations, the pods and/or fluid pads may be filled alternatively with a gas such as air, nitrogen, etc. In yet additional variations, the one or more pods and/or fluid pads may be filled with either a fluid or gas or a combination of both depending upon the desired degree of cushioning and force distribution. The fluid may be a low density fluid with a specific gravity of less than 0.9 or with a specific gravity of less than 0.7. The pods and/or fluid pads may contain solids in addition to fluid. Examples of such solids include glass microspheres. The solid may have a specific gravity of less than 0.9 or less than 0.7. Using low density materials can reduce the weight of the apparatus without reducing its size.

The one or more fluid pods may each occupy an envelope of e.g., 1 cm×1 cm×0.5 cm to about 3 cm×3 cm×3 cm, in an uncompressed state and they may be formed into various shapes, e.g., spherical, cylindrical, cubical, etc. Moreover, each of the pods may be formed from various materials such as polyurethane, silicone, vinyl, nylon, polyethylene vinyl acetate (PEVA), etc. having a thickness ranging from, e.g., 0.1 mm to 5 mm. Although the figure illustrates four pods, the number of pods contained within the inner pad may range anywhere from, e.g., 1 to 30 or more, arranged either uniformly or arbitrarily within the inner pad. Additionally, while the pods may be unconstrained within the inner pad such that they freely move relative to one another, the pods may be secured within the inner pad either to one another or to the inner pad itself such that their relative movement is constrained.

In yet other variations, rather than utilizing pods having a fluid contained within, one or more spring assemblies may be used to provide the cushioning support. These spring assemblies may utilize various spring types such as leaf or compression springs or various other types of biasing mechanisms.

In either case, the pods may transfer localized loads from the patient received by a few pods either to adjacent pods through the compression and transfer of pressure to adjacent contacting pods or through transmission via the fluid in the inner pad and/or outer pad. The amount of compression of the pods themselves may be controlled by the inner pad which envelopes the pods within a pad localized over the central portion. The inner pad may function as a hammocking layer to constrain the amount of displacement experienced by the individual pods but because the inner pad itself may be fluid filled, the inner pad may further provide support to the patient's body while also restricting compression of the pods. The amount of compression experienced by the individual pods may thus be controlled by the inner pad to range anywhere from, e.g., 0% to 90% (or 10% to 90%), of the uncompressed height of the pods.

The inner pad may be sized into various configurations depending upon, e.g., the number of pods or the area of the body to be supported. Moreover, the inner pad may also be made from the same or similar material as the pods, e.g., polyurethane, silicone, vinyl, nylon, polyethylene vinyl acetate (PEVA), etc. While the inner pad may be filled with a fluid (or gas or combination of both), as described above, the inner pad may alternatively be devoid of fluid and instead be used to constrain the expansion of the individual pods. Thus, inner pad may be optionally vented to allow for any trapped air to vent from between the pods when the pods undergo compression.

While the one or more pods and inner pad may be concentrated particularly around the region of the body to be supported, an additional outer pad may enclose and surround the inner pad which further encloses the one or more pods. The outer pad may be similarly filled with a fluid or gas (or combination of both), as described above, and may be enclosed by a layer of material either the same or similar to the material of the inner pad and/or pods and further have a uniform or variable thickness ranging from, e.g., 0.5 mm to 4 cm. The outer pad may further constrict the compression of the inner pad which in turn constricts the compression of the one or more pods while additionally providing cushioning support to the surrounding tissue or body structures. Moreover, the outer pad may further extend over the length of the entire assembly to provide cushioning support to the region of the body upon which the assembly is secured.

Further supporting the assembly is the outer shell which may function as a restricting support to control displacement and inhibit the further compression of the outer pad to prevent the patient's body from bottoming out. The outer shell may be formed on a single side of the assembly such that when the assembly is worn or used by the patient, the outer shell may be positioned away from the skin of the patient such that the outer pad remains in contact with the patient. The outer shell may be accordingly made to be relatively stiffer than the outer pad yet still be flexible enough for conforming over or around the patient's body. Accordingly, the outer shell may be made from materials including plastics such as polypropylene, ABS, PVC, polyethylene, nylon, acrylic, polycarbonate, etc. The outer shell may also be fabricated from other materials such as polymers, carbon fiber, light weight metals, elastomeric materials, rubbers, foams, etc. Depending upon the material used, the outside shell can have a thickness ranging from, e.g., 1 mm to 3 cm.

When the patient wears or uses the support assembly, the one or more fluid filled pods may thus support the body portion (such as the sacrum or trochanter) and due to the weight of the patient, the one or more pods may compress against one another by a limited amount. However, the one or more pods may be inhibited from bottoming out due to the surrounding hammocking inner pad. The pressure on the body portion may thus be reduced and distributed/transferred to the surrounding fluid present in the inner pad. Moreover, the presence of the surrounding outer pad may further transmit and redistribute the induced pressure upwards towards and against the surrounding body portions, such as the thigh area. This decrease in pressure can lead to a reduction in pressure against the localized body region to a value of less than or approximately 4.3 kPa and hence prevent tissue necrosis and reduce the occurrence of pressure ulcers.

In yet another variation, an assembly may further incorporate additional localized support regions along different portions of the assembly. Other variations of the assembly may incorporate baffles and other mechanisms to optionally create interconnected fluid regions. These regions may allow for reducing the amount of fluid in the entire system and prevent the fluid from pooling in one area.

In yet another variation, open cell foam may be placed between the individual inner and outer fluid layers. This foam layer may be saturated with fluid and allow for the transfer of fluid pressure between the different fluid layers.

Additional variations may incorporate a breathable layer covering at least a portion of the outer pad. The layer may be porous and can be made from materials such as cotton, etc., such that air may circulate through the pores or openings.

In yet other variations, one or more vibrating elements may be attached or integrated into the assembly, e.g., along the outer layer of the outer pad. These vibrating elements may vibrate to impart micro or macro vibrations directly against the contacted skin surface to relieve pressure over the contact area or into the fluid pad itself to indirectly vibrate against the skin surface. The vibrating elements may generate micro-vibrations on the order of about, e.g., 10 to 500 microns, in amplitude with a frequency ranging from about, e.g., 10 Hz to 300 Hz. These vibrations may allow for increased blood circulation and may also help decrease the incidence of pressure ulcers. Moreover, the vibrating elements may be comprised of piezoelectric, nitinol, or any other actuator driven elements.

In yet other variations, any of the embodiments described herein may incorporate various temperature control mechanisms. These may include one or more regions within the support pad assemblies which may be cooled and/or heated to prevent and/or treat pressure ulcers.

Alternative variations of the outer shell assembly may be utilized with any of the features described herein. One variation may include a support assembly having a central support which incorporates a fabric portion. A first support portion and a corresponding second support portion on an opposite side may each be angularly coupled to central portion and a separate back support portion may also be coupled to the central support.

The central portions as well as support portions and back support portion may be comprised of a conformable material (e.g., malleable metal such as aluminum or plastics, foams, or any other bendable material) which is relative stiffer than the fabric portion and inner or outer pads. The supporting portions may provide adequate support to a patient when the assembly is placed, e.g., upon a mattress or platform, while enabling the assembly to bend or flex into placement against the patient body when the patient lies upon the assembly. The support portions may incorporate a corresponding first conformable portion and second conformable portion fabricated from a stretchable or distendible material such as a mesh or fabric which is supported by one or more adjustable straps (e.g. straps with hook-and-loop fastening portions) coupling the conformable portions to their respective support portions. The flexibility of the conformable portions may enable the shell assembly to shape or conform more closely to the patient body and may also provide for enhanced comfort.

In another variation, the support portions may be attached to the central portion via one or more adjustable cords (e.g., bungee cords) columns pivotably attached to a platform and extending into connection with one or more openings within the respective support portions. In yet other variations, the supporting side portions may be comprised of composite assemblies which are adjustably configurable. The composite assembly may generally include a number of individual support elements (e.g., plastic, metal, foam, etc.) which are connected to one another along respective longitudinal axes in an alternating pattern. A tensioning member such as a wire, screw, etc., may be passed through each end of the support elements along the longitudinal axes with a tightening member coupled at the ends of the tensioning member.

In yet another outer shell assembly, the support portions may be comprised of angled supports which are adjustably secured to respective first and second adjustable supports which may be rotatable about first and second pivots. The adjustable supports may each support respective first and second conformable portions which provide a surface for supporting the bladder assembly against the patient.

In yet another variation of the outer shell assembly, the conforming supports may extend in a curved or arcuate mailer from the central support portion in a shaped shell configuration. The conforming supports may extend in strips or members which are shaped, e.g., like flower petals, and the supports may be secured in place using any number of securement mechanisms, e.g., friction hinge mechanisms, electromechanical locking systems, hydraulic locking systems, magnetic locking systems, electro or magneto-rheological locking systems, etc.

Additionally and/or optionally, any of the outer shell assemblies may incorporate one or more zones throughout various regions of the shell which may selectively or simultaneously squeeze, vibrate, or otherwise actuate. These selective zones may vibrate at a selected frequency and/or amplitude and may be actuated at fixed intervals or times.

Yet another variation of the outer shell assembly may include conforming supports which extend in a curved or arcuate shape for conforming more closely against the patient's body. The supports may each integrate one or more support members which are adjacent to respective sliding supports which may be tuned to push in or out relative to the central support portion to adjust a rotation or bend radius of each support independently of one another or simultaneously with each support. By moving or conforming the support portions against the patient's body, the fluid within the pad may be redistributed to reduce any pressure that may result below any bony prominences of the patient body.

With any of the variations described herein, different features and aspects from each of the variations may be combined with one another in various combinations.

BRIEF DESCRIPTION OF THE DRAWINGS

FIG. 16 shows a perspective view of another variation of an outer shell assembly where the support portions may be secured with one or more adjustable cords.

FIGS. 17A to 17C show front and perspective views of yet another variation of the supporting shell assembly utilizing columns for adjustably supporting the support portions.

FIG. 18 shows a perspective view of yet another variation where the central portion may incorporate respective composite assemblies which are adjustably configurable.

FIGS. 19A to 19C show perspective and side views of yet another outer shell assembly which incorporates a central support portion with respective first and second support portions which are angularly adjustable.

FIG. 37 shows individually shaped sections for head, pelvic region, and feet regions of a patient.

FIG. 38 shows cushioning that extends the entire length of the body with individually adjustable sections.

DETAILED DESCRIPTION OF THE INVENTION

Figure 1A:
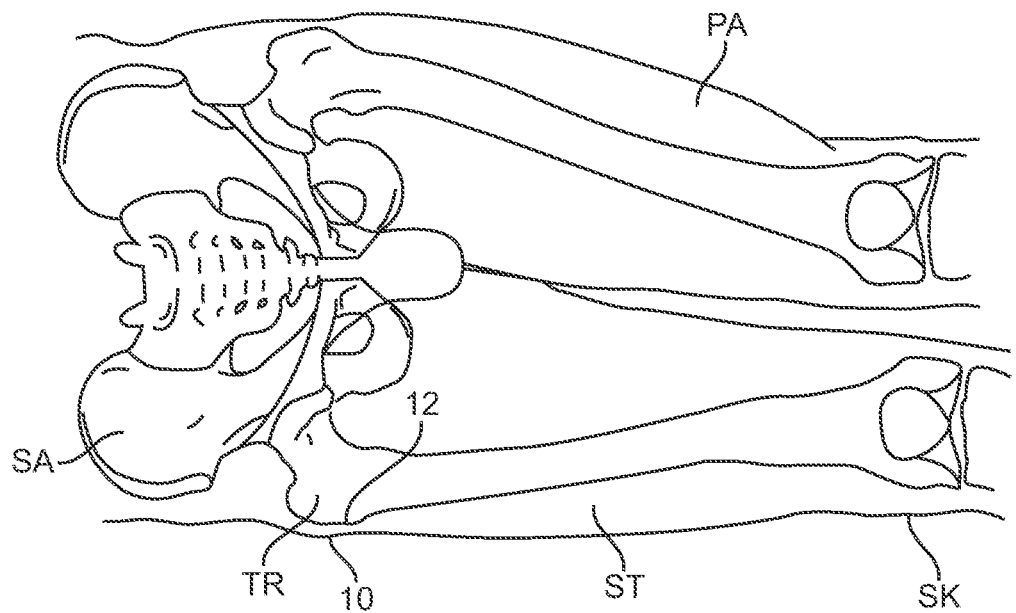
FIG. 1A shows a portion of a patient's body and the resultant induced pressure imparted on portions of the body such as the trochanter.

Generally, in a healthy individual, the presence of muscle mass and soft tissue ST usually functions to distribute and relieve pressure from bony protuberances of the body contacted against the underlying surface. However, when a patient PA is forced to lie on one portion of their body for extended periods of time, areas such as the sacrum SA or trochanter TR may compress a region of the skin SK and tissue 12 between the protuberance and a contact region 10 formed against the underlying surface as shown in FIG. 1A.

Typical pressures generated in the hip area for healthy individuals lying against a surface may range around 4 kPa. However, for older and/or diseased individuals, the contact pressures between regions of bony prominence and the skin is generally higher due to various factors such as muscle atrophy. For instance, increased pressures were found to range around 7.3 kPa for such older individuals. Blood circulation becomes restricted and tissue necrosis typically begins when pressures range above 4.3 kPa leading to the development of pressure ulcers.

Figure 1B:
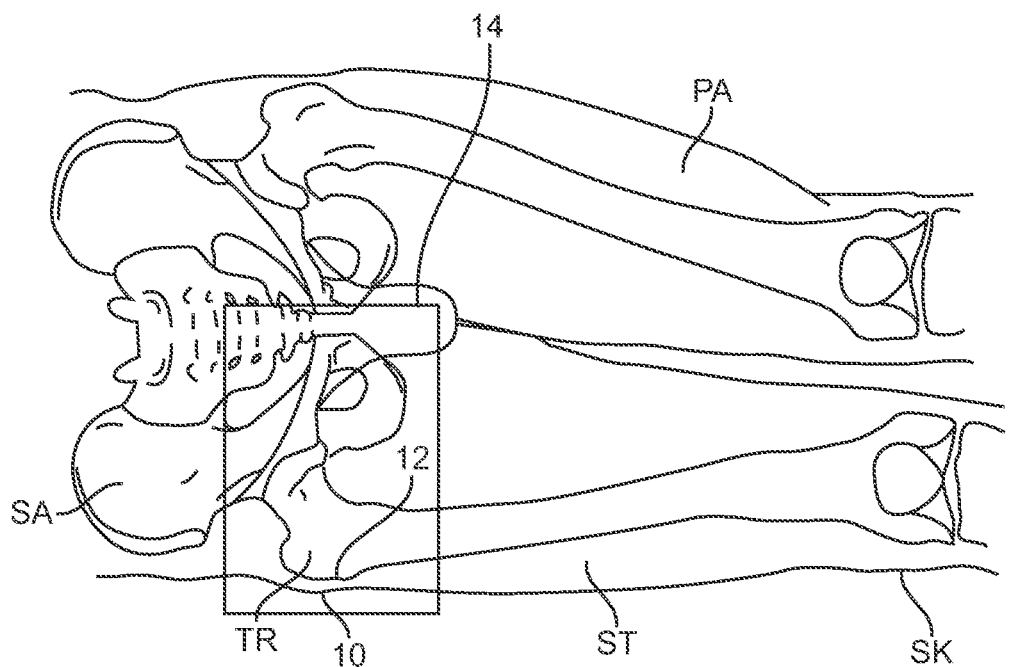
FIG. 1B shows a portion of the patient's body with a portable support assembly worn upon the body, e.g., around the hips, to alleviate pressure.

Generally, a portable support assembly 14 may be worn or used by an individual who may be bed-stricken for an extended period of time to prevent the formation of pressure ulcers. Such a portable support assembly 14 may be worn by the individual around particular regions of the body where pressure ulcers tend to form. e.g., sacrum SA, trochanter TR ischium, as well as any other region of the body where support is desired. The portable support assembly 14 may be formed into an elongated shape to be wrapped entirely around the patient's body, e.g., around the hips or lower back, or a portion of the body, e.g., around the ankles or feet. Thus, although the example shown in FIG. 1B illustrates the assembly 14 placed around the trochanter TR or sacrum SA, other embodiments may include various shapes of the assembly 14 which may be sized for particular body regions and are intended to be within the scope of this disclosure.

Moreover, the support assembly 14 is configured to be portable such that it may be worn directly over or upon the patient's body independently from the underlying bed or cushion. Accordingly, the patient may utilize the support assembly 14 on any underlying bed or platform. Additionally, while the examples described illustrate portable support assemblies, the support assembly may be integrated into a bed, underlying cushion, and/or mattress pad if so desired.

Figure 2:
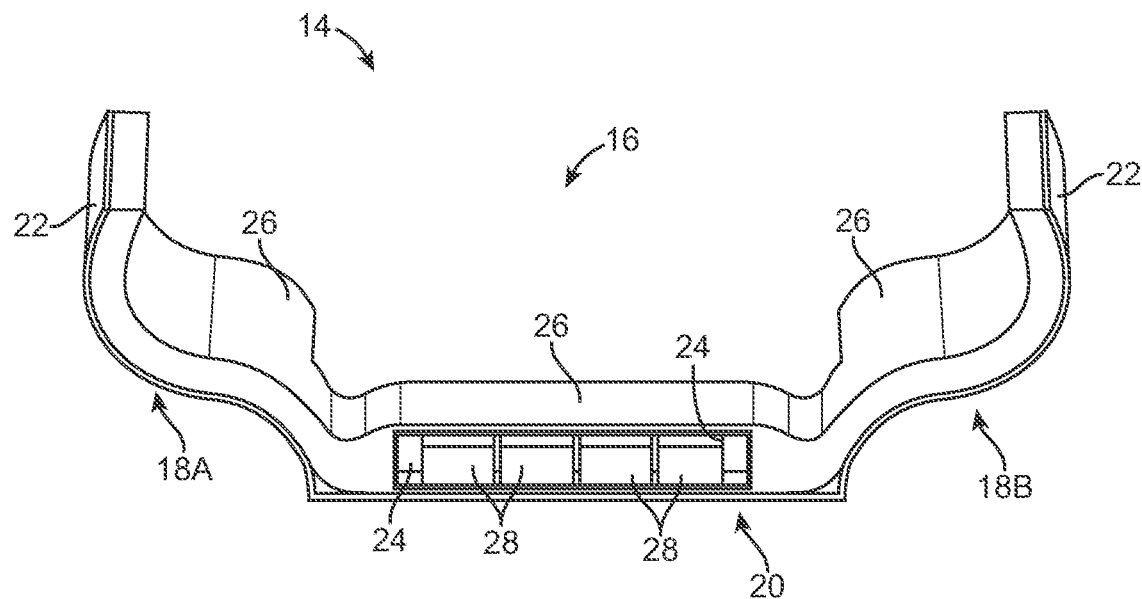
FIG. 2 shows a cross-sectional end view of one variation of a portable support assembly illustrating the various layered fluid pads contained within.

One variation of the portable support assembly 14 is illustrated in the cross-sectional view of FIG. 2, which illustrates a wearable hip-support system. In this variation, the support assembly 14 may generally define a securement area 16 for placement against the region of the body requiring support such as the sacrum SA. The securement area 16 may generally comprise a central portion 20 with first conformable portion 18A and/or second conformable portion 18B extending from either side of the central portion 20. The first and/or second conformable portions 18A, 18B may be flexible enough to allow for the portions 18A, 18B to be wrapped around or about at least a portion of the patient's body such that the assembly 14 may remain secured to the body even when the patient moves about thereby maintaining the central portion 20 against the supported region of the body.

The central portion 20 may provide the greatest amount of localized support to the patient body by utilizing several fluid layers which are contained one within another to receive the localized loading from the protuberance from the patient's body and distribute the localized load onto the surrounding areas and to further control their displacement ad inhibit or prevent the bottoming out of the fluid layers. The central portion 20 may thus contain one or more fluid filled individual pods 28 which may be enclosed entirely within an inner pad 24 which envelopes the one or more pods 28 within a secondary layer of fluid. The inner pad 24 may be localized along the central portion 20. The inner pad 24 may be filled with a fluid (or gas) or optionally be devoid of any fluid, as described in further detail below. Both the one or more pods 28 and inner pad 24 are then enclosed entirely by a tertiary layer of fluid within an outer pad 26 which may extend over the entire assembly 14. Each of the fluid layers may be secured to an outer shell 22 which is relatively stiffer than the fluid layers and may restrict or limit the expansion or movement of the fluid pods 28 and/or pads 24, 26. While the assembly 14 is adjustable to fit a particular patient, the outer pad 26, in particular, may optionally be filled with the fluid to a variable amount to further ensure that the assembly 14 may be fitted or conformed to the anatomy of a particular patient.

Each of the one or more pods 28 may be separated from one another such that no fluid communication occurs between the pods 28 and/or with the inner pad 24. Similarly, the inner pad 24 may be separate from the outer pad 26 such that no fluid communication occurs between the two. In other variations, some fluid communication may occur between the inner pad 24 and outer pad 26 so long as the inner pad 24 constrains and prevents the over-compression of the one or more pods 28 to control their displacement and inhibit their bottoming out.

Each of the pods 28 and/or fluid pads 24, 26 may be filled with an incompressible fluid such as water, salt solution, viscous oil, or some other biocompatible fluid. Yet in other variations, the pods 28 and/or fluid pads 24, 26 may be filled alternatively with a gas such as air, nitrogen, etc. In yet additional variations, the one or more pods 28 and/or fluid pads 24, 26 may be filled with either a fluid or gas or a combination of both depending upon the desired degree of cushioning and force distribution. In some embodiments, the fluid that fills the pods 28 and or fluid pads 24, 26 may be a liquid or flowable semisolid to reduce the amount of leakage relative to that observed with use of a gas.

The one or more fluid pods 28 may each occupy an envelope of e.g., 1 cm×1 cm×0.5 cm to about 3 cm×3 cm×3 cm or even 35 cm×5 cm×5 cm, in an uncompressed state and they may be formed into various shapes, e.g., spherical, cylindrical, cubical, etc. Moreover, each of the pods may be formed from various materials such as polyurethane, silicone, vinyl, nylon, polyethylene vinyl acetate (PEVA), etc. having a thickness ranging from, e.g., 0.1 mm to 5 mm. Although the figure illustrates four pods 28, the number of pods 28 contained within the inner pad 24 may range anywhere from, e.g., 1 to 30 or more (such as 2 to 100), arranged either uniformly or arbitrarily within the inner pad 24. Additionally, while the pods 28 may be constrained within the inner pad 24 such that they freely move relative to one another, the pods 28 may be secured within the inner pad 24 either to one another or to the inner pad 24 itself such that their relative movement is constrained.

In either case, the pods 28 may transfer localized loads from the patient received by a few pods 28 either to adjacent pods through the compression and transfer of pressure to adjacent contacting pods or through transmission via the fluid in the inner pad 24 and/or outer pad 26. The amount of compression of the pods 28 themselves may be controlled by the inner pad 24 which envelopes the pods 28 within a pad localized over the central portion 20. The inner pad 24 may function as a hammocking layer to constrain the amount of displacement experienced by the individual pods 28 and provide an increase in the net force constant relative to the force constant due to compression of the individual pods 28. This increase in net force may be due to pressure applied by inner pad directly on the surfaces of the individual pods 28 and/or due to force applied through the fluid that fills the inner pad 24. Thus, the inner pad 24 may further provide support to the patient's body while also restricting compression of the pods 28. The amount of compression experienced by the individual pods 28 may thus be controlled by the inner pad 24 to range anywhere from, e.g., 0% to 90% (or 10% to 90%), of the uncompressed height of the pods 28. For example, for a pod 28 having an uncompressed height of 3 cm, the compression of the pod 28 may range anywhere from, e.g., 0 cm to 2.7 cm (or 0.3 cm to 2.7 cm).

The inner pad 24 may be sized into various configurations depending upon, e.g., the number of pods 28 or the area of the body to be supported. Moreover, the inner pad 24 may also be made from the same or similar material as the pods 28, e.g., polyurethane, silicone, vinyl, nylon, polyethylene vinyl acetate (PEVA), etc. While the inner pad 24 may be filled with a fluid (or gas or combination of both), as described above, the inner pad 24 may alternatively be devoid of fluid and instead be used to constrain the expansion of the individual pods 28. Thus, inner pad 24 may be optionally vented to allow for any trapped air to vent from between the pods 28 when the pods 28 undergo compression.

While the one or more pods 28 and inner pad 24 may be concentrated particularly around the region of the body to be supported, an additional outer pad 26 may enclose and surround the inner pad 24 which further encloses the one or more pods 28. The outer pad 26 may be similarly filled with a fluid or gas (or combination of both), as described above, and may be enclosed by a layer of material either the same or similar to the material of the inner pad 24 and/or pods 28 and further have a uniform or variable thickness ranging from, e.g., 0.5 nm to 4 cm. The outer pad 26 may further constrict the compression of the inner pad 24 which in turn constricts the compression of the one or more pods 28 while additionally providing cushioning support to the surrounding tissue or body structures. Moreover, the outer pad 26 may further extend over the length of the entire assembly 14 to provide cushioning support to the region of the body upon which the assembly 14 is secured.

Additionally, while the outer pad 26 may have a thickness ranging anywhere from, e.g., 5 mm to 2 cm or more (such as in areas in contact against the sacrum), the inner pad 24, outer pad 26, and/or pods 28 may be filled with a fluid having a density which is relatively higher than the density of a body. For example, the density of the human body is about 1.01 g/cm$^2$ and a salt solution filled within any of the pads 24, 26 and/or pods 28 can have density of e.g., 1.03 to 1.1 g/cm$^2$. By using a highly saturated salt solution used as the fluid, a further cushioning effect may be achieved for providing comfort to the patient when the assembly is in use. The fluid may have a low density of, e.g., 0.3 to 0.9 g/cm$^3$ or 0.5 to 0.7 g/cm$^3$.

Further supporting the assembly is the outer shell 22 which may function as a restricting support to control displacement and inhibit the further compression of the outer pad 26 to prevent the patient's body from bottoming out. The outer shell 22 may be formed on a single side of the assembly 14 such that when the assembly 14 is worn by the patient, the outer shell 22 may be positioned away from the skin of the patient such that the outer pad 26 remains in contact with the patient. The outer shell 22 may be accordingly made to be relatively stiffer than the outer pad 26 yet still be flexible enough for conforming over or around the patient's body. Alternatively, the outer shell 22 may be rigid to provide additional support. Accordingly, the outer shell 22 may be made from materials including plastics such as polypropylene, ABS, PVC, polyethylene, nylon, acrylic, polycarbonate, etc. The outer shell 22 may also be fabricated from other materials such as polymers, carbon fiber, light weight metals, foams, etc. Depending upon the material used, the outside shell 22 can have a thickness ranging from, e.g., 1 mm to 3 cm or more.

When the patient wears or uses the support assembly, the one or more fluid filled pods 28 may thus support the body portion (such as the sacrum SA or trochanter TR) and due to the weight of the patient, the one or more pods 28 may compress against one another by a limited amount. However, the one or more pods 28 may be inhibited from bottoming out due to the surrounding hammocking inner pad 24. The pressure on the body portion may thus be reduced and distributed/transferred to the surrounding fluid present in the inner pad 24. Moreover, the presence of the surrounding outer pad 26 may further transmit and redistribute the induced pressure upwards towards and against the surrounding body portions, such as the thigh area. This decrease in pressure can lead to a reduction in pressure against the localized body region to a value of less than or approximately 4.3 kPa and hence prevent tissue necrosis and reduce the occurrence of pressure ulcers.

In another variation, the one or more pods 28 may be connected directly to the outer shell 22 and contained by the hammocking inner pad layer 24 which prevents the pods 28 from bottoming out, as described above. The outer fluid pad 26 may be laid atop the one or more pods 28 and hammocking inner layer 24. Alternatively, the one or more pods 28 (contained within the hammocking inner layer 24) may come into direct contact against the patient and the outer fluid pad 26 may instead be attached directly to the outer shell 22.

Figure 3:
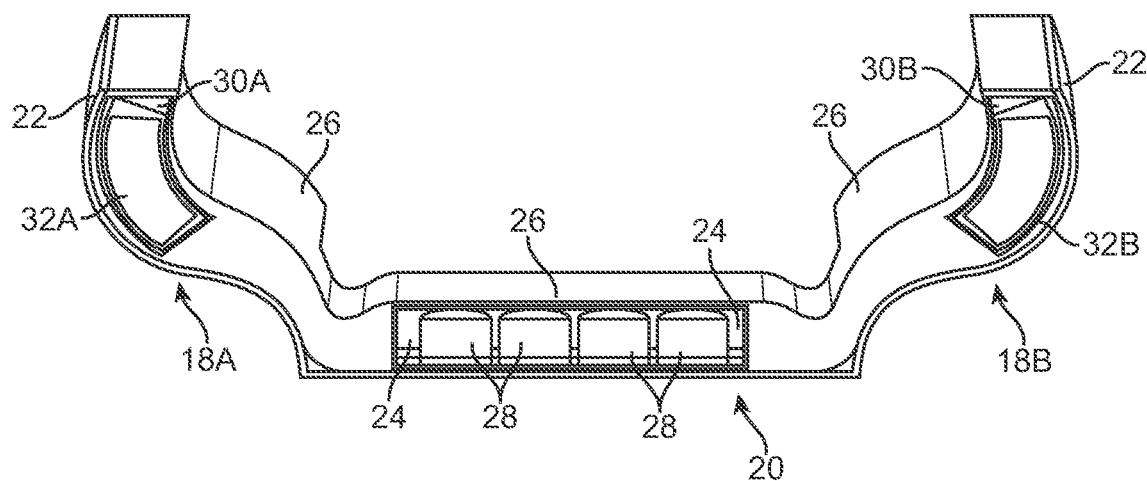
FIG. 3 shows a cross-sectional end view of another variation of the support assembly illustrating additional fluid pads contained within.

In yet another variation, FIG. 3 shows a cross-sectional view of an assembly which is similarly constructed to the variation of FIG. 2 but which may further incorporate additional localized support regions. For instance, in the variation shown, a first fluid inner pad 30A having one or more pods 32A contained within may be integrated along the first conformable portion 18A extending from the central portion 20. Similarly, a second fluid inner pad 30B having one or more pods 32B contained within may be integrated along the second conformable portion 18B extending from the opposite side of the central portion 20. In this variation, the conformable portions 18A, 18B may be wrapped or secured against the hips of the patient such that the corresponding inner pads 30A, 30B are positioned over either or both trochanters TR of the patient while the central portion 20 is positioned over the sacrum SA to provide support around the entire hip and lower back regions of the patient. As described herein, the number and size of the pods 32A, 32B may be varied. The inner layer 24 may be compliant or non-compliant. The inner layer 24 may be compliant on the selected surfaces, such as those contacting the patient, while non-compliant on other surfaces, such as surfaces substantially perpendicular to the surfaces contacting the patient.

Figure 4A:
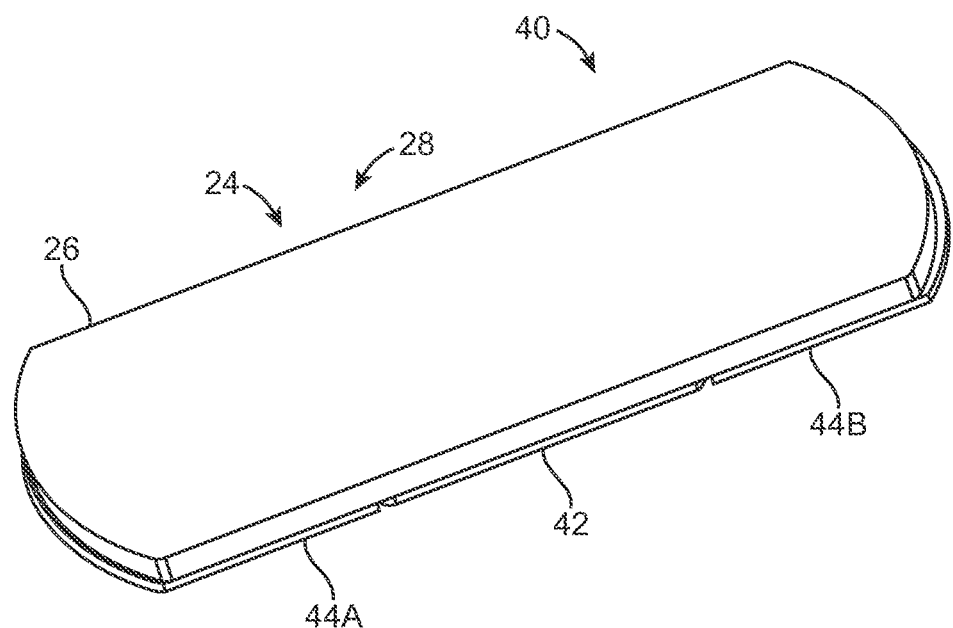
FIGS. 4A and 4B show perspective views of another variation of the support assembly which may be layered upon a hinged platform.
Figure 4B:
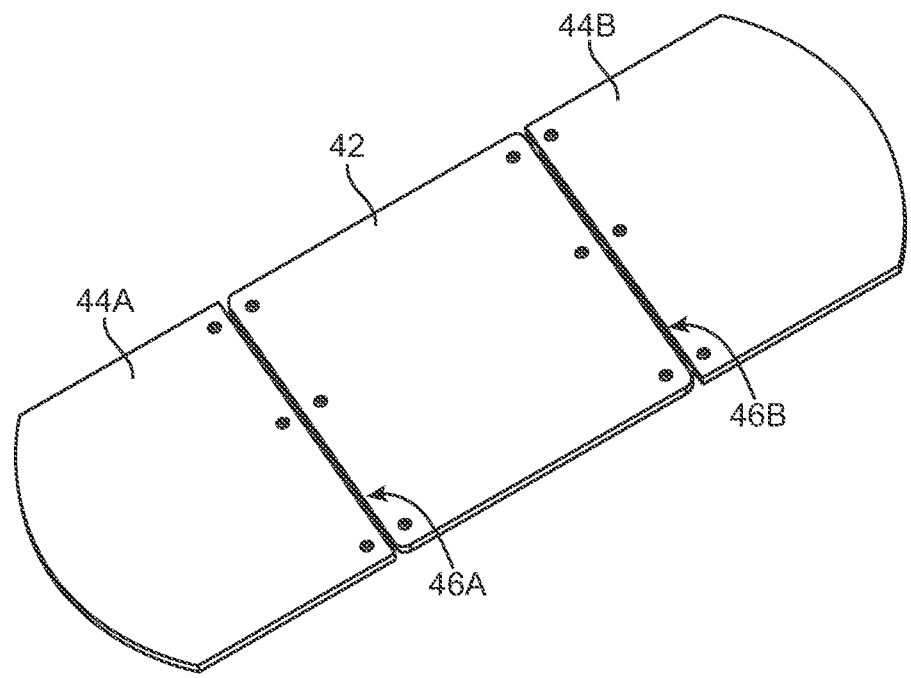

While the support assembly 14 may be sized in various configurations depending upon the region of the body to which the assembly is to be positioned, another example of an assembly configuration is shown in the perspective views of FIGS. 4A and 4B. In this example, the support system may be configured as a hinged fluid pad assembly 40 having a central portion 42 and a first foldable portion 44A and a second foldable portion 44B extending from either side of the central portion 42. The outer shell of the foldable portions 44A, 44B may be coupled via corresponding first hinged region 46A and second hinged region 46B such that the assembly 40 may be laid flat upon a bed or platform. The inner fluid pad 24 and one or more pods 28 may be positioned upon the central portion 42 and/or optionally along the first and/or second foldable portions 44A, 44B as well while the outer pad 26 may extend continuously along the length of the entire assembly 40. In use, the assembly 40 may be laid flat and folded over upon or against the patient's body and secured accordingly.

Other variations of the assembly may incorporate baffles and other mechanisms to optionally create interconnected fluid regions. These regions may allow for reducing the amount of fluid in the entire system and prevent the fluid from pooling in one area.

In yet another variation, open cell foam may be placed between the individual inner and outer fluid layers. This foam layer may be saturated with fluid and allow for the transfer of fluid pressure between the different fluid layers.

Figure 5:
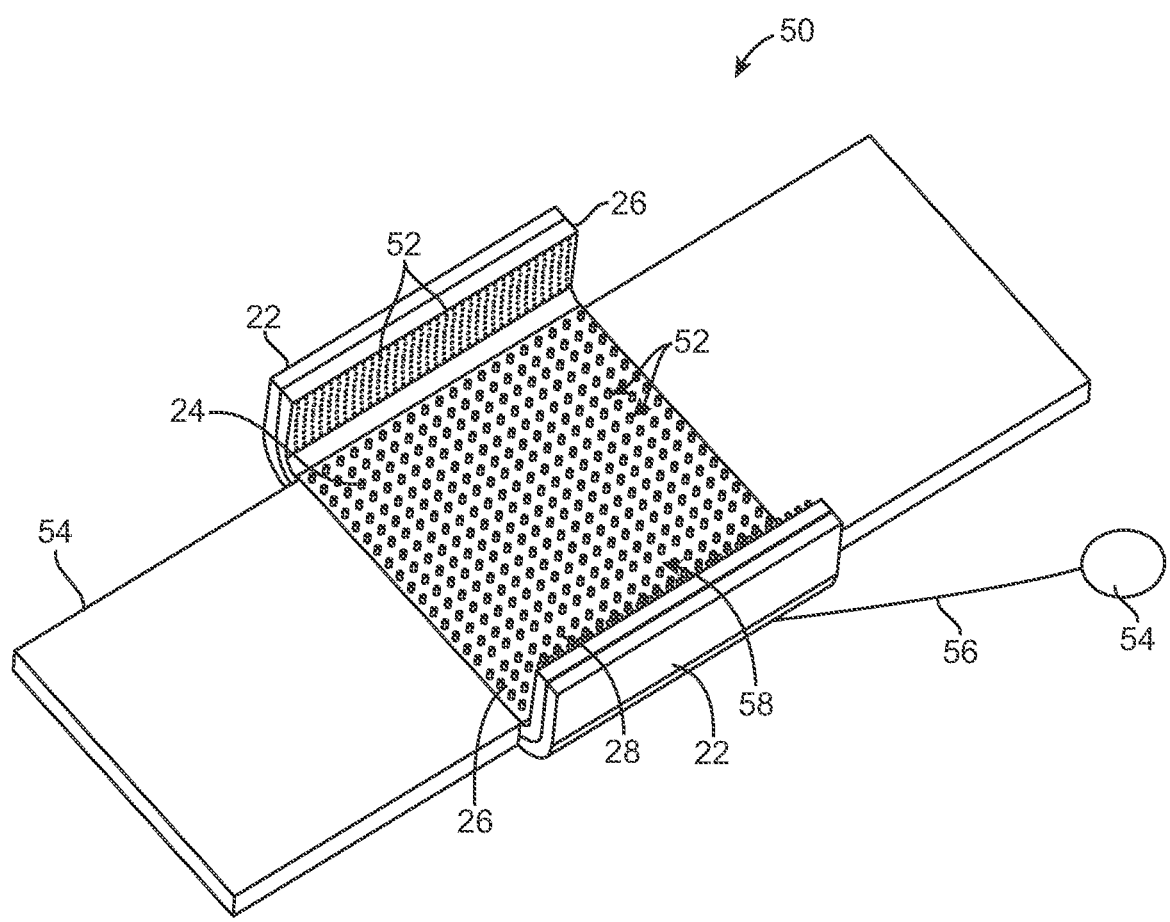
FIG. 5 shows a perspective view of yet another variation of the support assembly incorporating features such as a cooling mechanism and/or a plurality of vibrating elements.

FIG. 5 shows a perspective view of yet another variation in which the support assembly 50 may incorporate a breathable layer covering at least a portion of the outer pad 26. The layer may be porous and can be made from materials such as cotton, etc., such that air may circulate through the pores or openings 52. A pump 54 coupled via a fluid line 56 may be optionally attached to the assembly 50 to pump air through the pores or openings 52.

In yet other variations, one or more vibrating elements 58 may be attached or integrated into the assembly 50, e.g., along the outer layer of the outer pad 26. These vibrating elements 58 may vibrate to impart micro or macro vibrations directly against the contacted skin surface to relieve pressure over the contact area or into the fluid pad itself to indirectly vibrate against the skin surface. The vibrating elements 58 may generate micro-vibrations on the order of about, e.g., 10 to 500 microns, in amplitude with a frequency ranging from about, e.g., 10 Hz to 300 Hz. These vibrations may allow for increased blood circulation and may also help decrease the incidence of pressure ulcers. Moreover, the vibrating elements 58 may be comprised of piezoelectric, nitinol, or any other actuator driven elements.

In other variations, the assembly 50 may be integrated with an optional mattress topper 54 to provide stability to the assembly 50 when positioned against the patient.

Figure 6A:
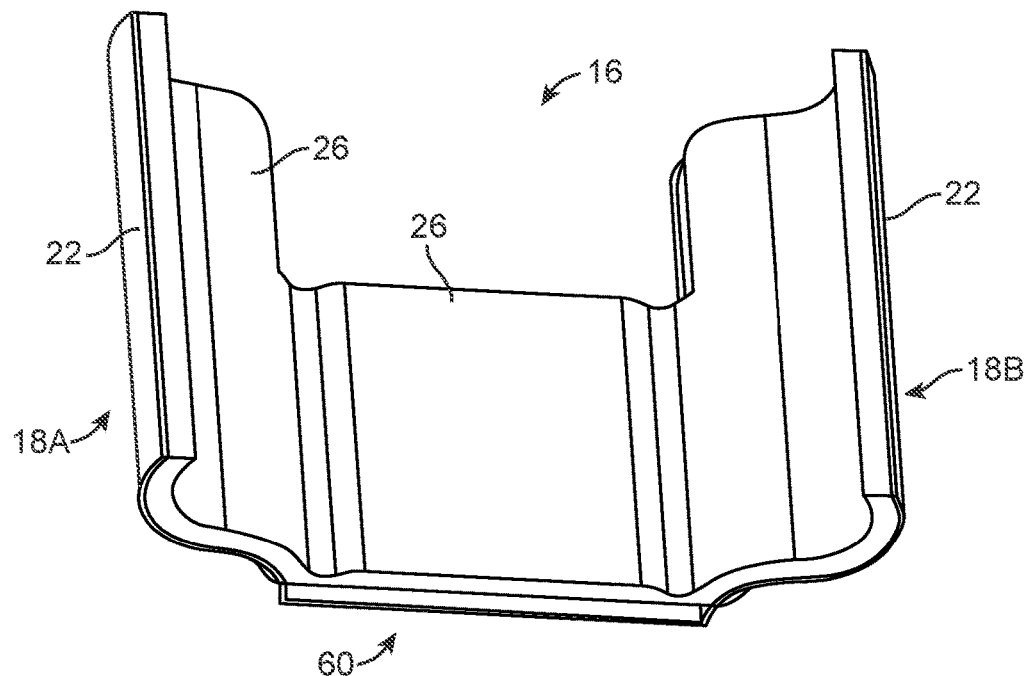
FIGS. 6A and 6B show perspective and side views of another variation of the support assembly which utilizes one or more spring assemblies in combination with the inner and/or outer pad.
Figure 6B:
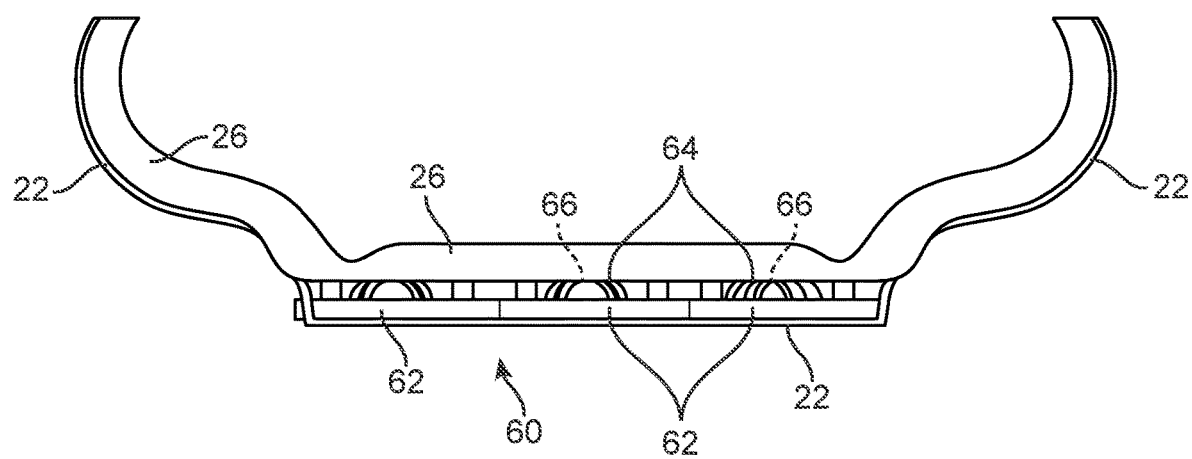

In yet another variation, the support assembly may utilize one or more spring assemblies in combination with the inner pad 24 and/or outer pad 26 rather than using the one or more pods 28. An example is shown in the perspective view of FIG. 6A which shows a variation of the assembly with outer pad 26 positioned atop one or more spring assemblies 60 rather than one or more pods. FIG. 6B shows a partial cross-sectional side view of one or more spring assemblies 60 secured upon the outer shell 22 and the outer pad 26 positioned atop the spring assemblies 60. The number of individual compression assemblies 60 in the array can vary, e.g., from 1 to 25 or more depending upon the desired treatment area. Moreover, each of the individual spring assemblies 60 is designed to be non-bottoming and further designed to reduce the pressure to less than or equal to, e.g., 32 mm of Hg, when a person uses the system.

One variation of a spring assembly may have an individual base 62 for securement to the outer shell 22 and a corresponding top layer 66 for contacting against the outer pad 26 and/or directly against the patient body. Between the top layer 66 and base 62 are one or more biasing members 64, e.g., spring elements. An example is shown in the perspective view of FIG. 7 which illustrates the top layer 66 and base 62 formed in a circular configuration although they may be formed in any number of shapes which are suitable for placement between the shell 22 and outer pad 26. The variation of biasing members 64 shown may comprise superelastic shape memory alloys such as heat-formed Nitinol formed, e.g., into flattened strips of material which are configured into leaf or compression springs, as shown. When a force is applied to the top layer 66, such as by the patient body, the biasing members 64 compress and their height decreases in response to the application of the force causing the top layer 66 to move towards the base 62.

Figure 7:
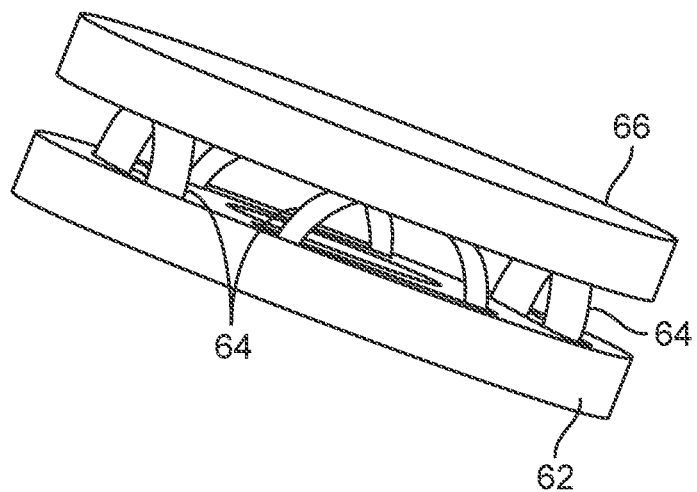
FIG. 7 shows a perspective view of one variation of a spring assembly.

The spring assembly shown in FIG. 7 is illustrated as having four biasing members 64 but the assembly can have one, two, three, or more biasing members 64. The biasing members 64 can also be made from other materials such as stainless steels, plastics, elastomers, and other suitable materials.

Figure 8:
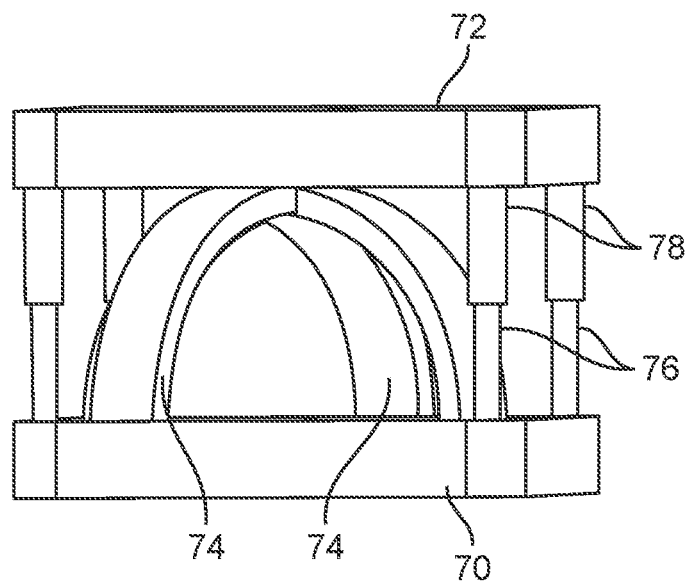
FIG. 8 shows a perspective view of another variation of a spring assembly.

FIG. 8 shows an alternative variation of a spring assembly having a base 70 and a top layer 72 with the biasing members 74 as previously described. The assembly may further have one or more post members 76 extending from the base 70 for translational engagement with one or more corresponding guide members 78 which may be aligned to receive the post members 76. The post members 76 may prevent the top layer 72 from rotating out of alignment with respect to base 70 during use. Moreover, the biasing members 74 may be designed to be a multiple prong anchor or flower design although any of the spring designs described herein may be used.

The individual spring assembly can have a surface area, e.g., from 0.5 to 1.0 $cm^2$ or even up to 200 $cm^2$, and an uncompressed height ranging from e.g., 1 cm to 3 cm. The biasing members 64 can also vary from having a constant force to having compression systems with a single spring constant or multiple spring constants.

Moreover, various other biasing elements such as extension springs, leaf springs, torsion springs, or any formed or shaped design which can accomplish similar functions may be used. Aside from the design, the different kinds of springs and compression pods may be designed to have spring constants either independently or on a system level such that the displacement or travel to support the patient does not result in pressures greater than, e.g., 4.3 kPA or similar pressures, which can cause tissue necrosis and lead to formation of pressure ulcers.

Figure 9A:
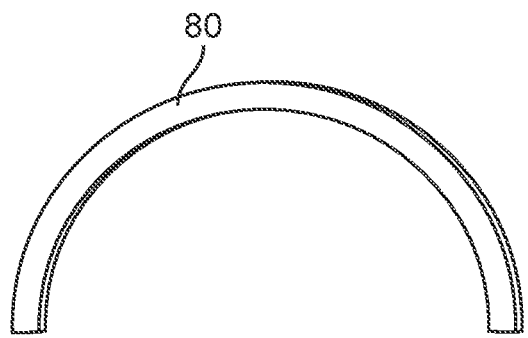
FIGS. 9A to 9D show various spring designs which may be used with any of the spring assemblies.
Figure 9B:
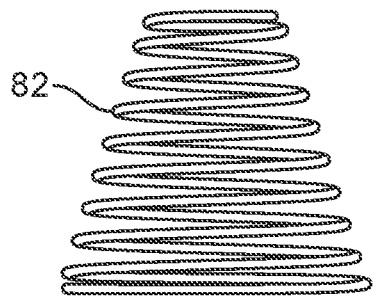
Figure 9C:
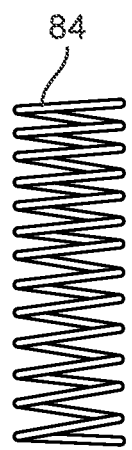
Figure 9D:
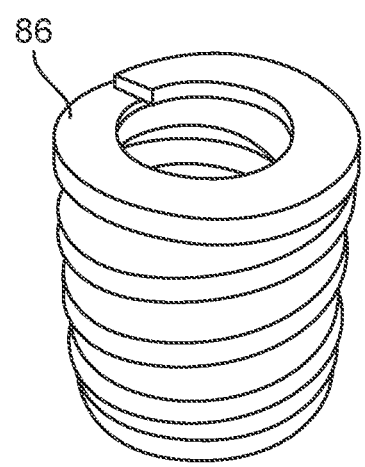

Other examples of various spring designs which may be used with any of the assemblies described herein are shown in FIGS. 9A to 9D. For instance, FIG. 9A shows a side view of a leaf spring 80 while FIGS. 9B and 9C show side views of a conical spring 82 and a cylindrical spring 84, respectively, which may be used as well. FIG. 9D shows a perspective view of an elastomeric spring 86 which may also be used, if so desired.

EXPERIMENTS

Tests using exemplary embodiments of the support assembly described herein have been conducted utilizing an array of individual fluid pods enclosed within an inner enveloping pad. This assembly was then enveloped within an outer fluid pad where both the fluid pods and outer pads were filled with water. The assembly was positioned near a simulated sacrum region and a similar arrangement was positioned near a simulated trocanter region.

An artificial male hip model was used to which a 0 to 20 lb FLEXIFORCE® (Tekscan, Inc., MA) sensor was attached to the sacrum region of the hip model. The FLEXIFORCE® sensor was used to sense contact force/pressure and an 8 lb load (ball) was used as the simulated load of a patient.

A first test had the hip model placed on a simulated mattress having a foam pillow with a thickness of about 1 cm. The hip model was then loaded three times with the 8 lb load and a corresponding force reading was recorded. A second test was then conducted where the hip model was placed on the support assembly pad and was then loaded with the 8 lb load. The hip model was then loaded again three times with the 8 lb load and a corresponding force reading was recorded. The tabulated results are shown in the following Table 1:

TABLE 1

Force measurements results from simulated loading.

| Test No | Force in N (simulated mattress) | Force in N (support assembly pad) | Force/Pressure (decrease by support assembly pad) |
|---|---|---|---|
| 1 | 7.70 | 4.29 | 44% |
| 2 | 6.33 | 3.42 | 46% |
| 3 | 5.65 | 3.42 | 39% |

Accordingly, use of the support assembly pad yielded an average reduction of 43% in measured pressure as experienced by the sacrum.

In another test, another exemplary embodiment of the support assembly (such as the variation shown in FIG. 15A) was tested on a mannequin positioned within the support assembly. The mannequin was further weighed down to increase the amount of weight placed against the support assembly. A measurement of the weighted mannequin was also observed upon a standard mattress without the support assembly for comparison purposes. Pressure sensors were used to record the resulting peak pressure measurements upon the mattress and upon the support assembly as well. Additionally, the overall area of contact between the mannequin and the mattress and between the support assembly was also recorded via a pressure map.

The results were recorded and the change in pressure (as well as contact sensing area) between the mattress and the support assembly were tabulated, as shown in the following Table 2:

TABLE 2

Pressure measurement results from simulated loading upon mannequin.

| Test | Peak Pressure (mmHg) | Sensing Area (in²) |
|---|---|---|
| Mattress | >200 | 41.81 |
| Support Assembly | 63.47 | 135.59 |
| Change | >−68% | 224% |

As observed, the recorded peak pressure values upon the mannequin when placed upon the mattress and compared to when placed upon the support assembly resulted in a pressure reduction of over 68% with an increase in the supporting area of 224%.

The test was then reproduced upon a human subject and the same measurements were taken, as shown in the following Table 3:

TABLE 3

Pressure measurement results from simulated loading upon human subject.

| Test | Peak Pressure (mmHg) | Sensing Area (in²) |
|---|---|---|
| Mattress | 101.15 | 181.92 |
| Support Assembly | 63.77 | 249.35 |
| Change | −37% | 37% |

As observed, the recorded peak pressure values upon the human subject when placed upon the mattress and compared to when placed upon the support assembly likewise resulted in a pressure reduction of over 37% with an increase in the supporting area of 37%.

Temperature Control

Additionally and/or alternatively, any of the variations described herein may also incorporate the use of temperature modulation and control to further help prevent the formation of pressure ulcers. For example, the support assembly pad may be controlled to have a temperature which is lower than body temperature to help prevent the formation of pressure ulcers while having an assembly pad controlled to have a temperature which is higher than body temperature can be used to treat pressure ulcers which have already formed upon the body. For example, the assembly pad can be configured to control the contacted skin/tissue temperature to within ±10° C. of body temperature.

Figure 10:
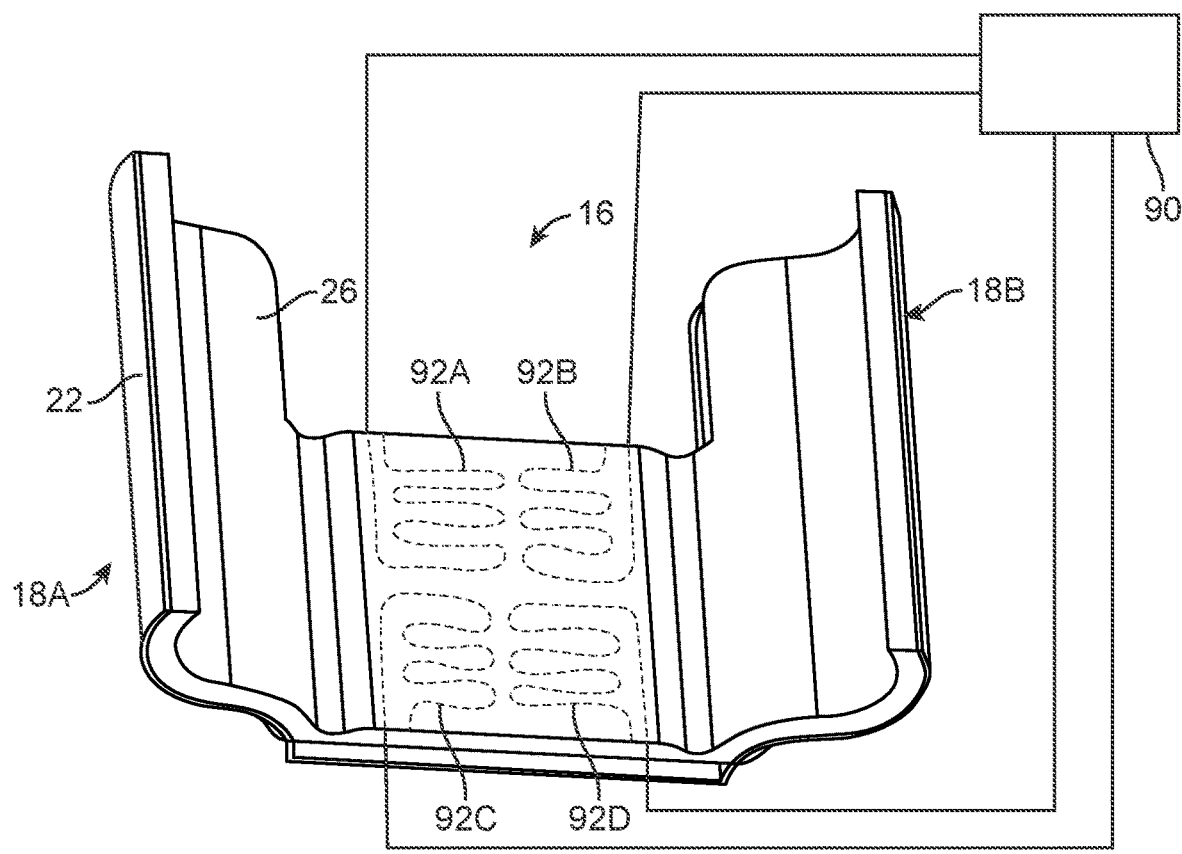
FIG. 10 shows a perspective view of another variation of the support pad assembly having one or more temperature control regions.
Figure 11:
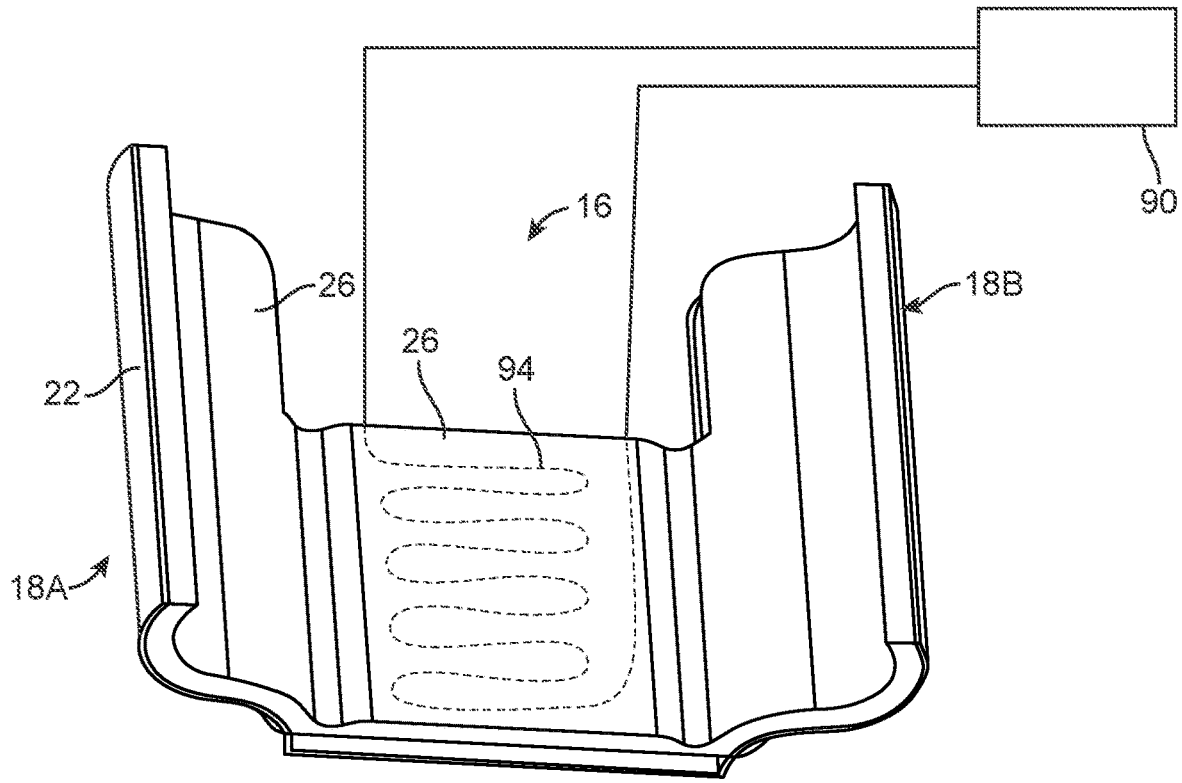
FIG. 11 shows a perspective view of another variation of the support pad assembly having a single temperature control region.

In addition to unidirectional temperature control (either heating or cooling) bidirectional temperature control can be achieved (selectively or alternatively heating and/or cooling). This allows the same assembly pad to be used for prevention and treatment of pressure ulcers. Temperature control can be achieved using any of several various methods and mechanisms. One example is shown in the perspective view of FIG. 10 which illustrates an assembly pad having several individual temperature regions 92A, 92B, 92C, 92D which may be controlled individually or simultaneously to heat or cool specified regions of the pad assembly. Each of the temperature regions may be in electrical communication with a controller 90, e.g., processor, which may be integrated with the pad assembly or arranged as a separate mechanism. FIG. 11 shows another variation where single temperature region 94 may be integrated over the pad assembly to heat or cool the entire pad assembly in contact with the patient.

The unidirectional or bidirectional temperature control may utilize any number of temperature altering mechanisms.

For example, thermoelectric cooling and heating elements (e.g., Peltier junctions) may be used or resistive heating and cooling elements may be used. Alternatively, inductive heating and cooling elements may also be used. Additionally and/or alternatively, chemically cooling and/or heating reacting materials (e.g., exothermic and/or endothermic) may be used as the fluid filling the one or more pods and/or pads. In yet another alternative, a cooling or heating fluid may be pumped in a circulating manner with an externally located cooling and/or heating mechanisms in fluid communication with a pumping mechanism.

Figure 12:
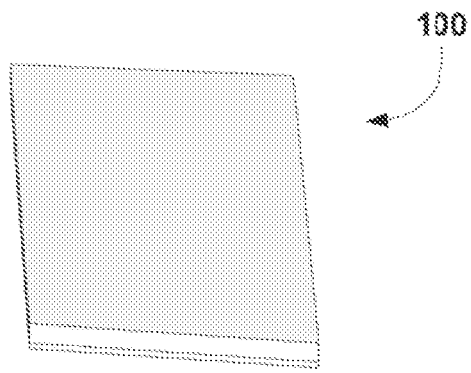
FIG. 12 shows a perspective view of another variation of a support pad configured for alternative uses such as with a wheelchair.
Figure 13:
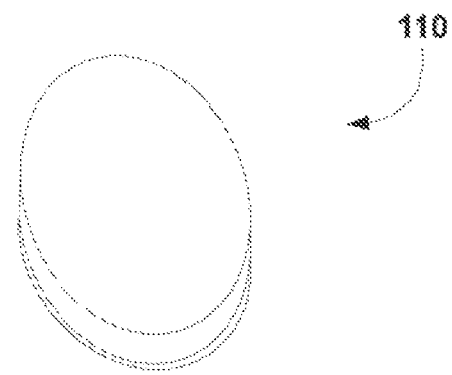
FIG. 13 shows a perspective view of yet another variation of a support pad configured for other regions of the body such as an elbow.

In yet other variations, the pad assembly may be designed for alternative uses. For example, the pad may be configured for use by a patient sitting in a wheelchair, standard chair, or other sitting, standing or sleeping devices or platforms. An example of a simplified pad assembly 100 is shown in the perspective view of FIG. 12. Alternatively, a pad assembly 110 shown in FIG. 13 may be configured for resting, e.g., during surgery, beneath an extremity such as an elbow or any other portion of the body which may come into contact against a hard surface for an extended period of time. The configured pad 110 may cushion, e.g., the ulnar nerve and may include a flat pad with a single fluid pod, for instance.

Figure 14:
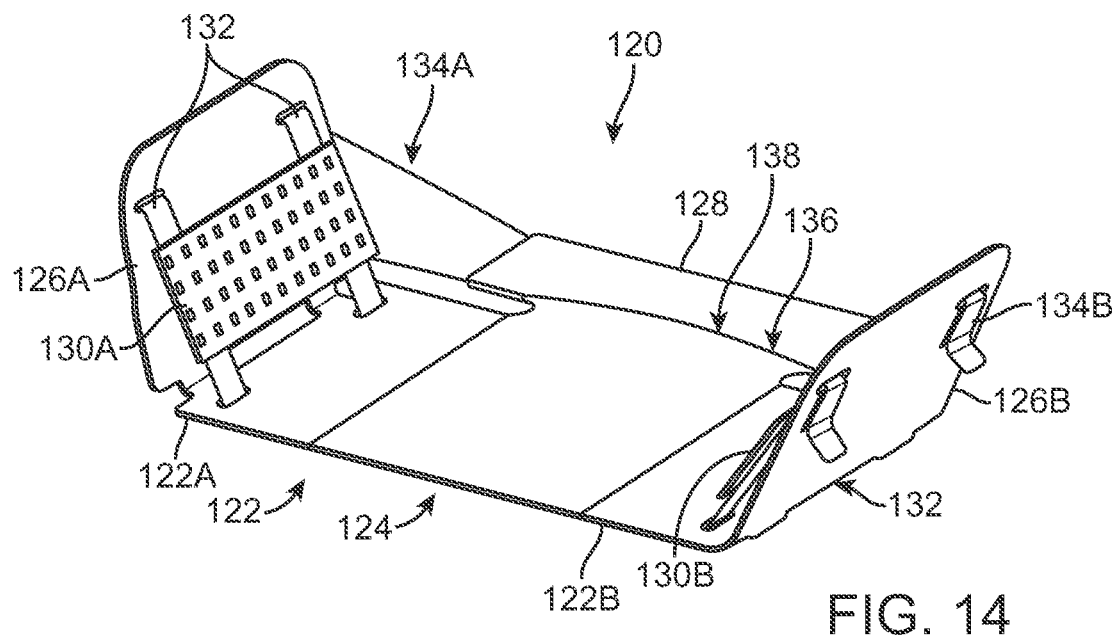
FIG. 14 shows a perspective view of another variation of an outer shell assembly which may incorporate fabric portions and an angled back support.

Yet another alternative of the pad assembly is shown in the perspective view of FIG. 14. In this variation, a support assembly 120 which is designed to confine and conform a fluid bladder to the anatomical features of the patient body (such as hip region, sacrum region etc.) is shown. The support assembly 120 may generally comprise a central support 122 having a first central portion 122A and a second central portion 122B coupled to one another via a fabric portion 124. An additional first support portion 126A and a corresponding second support portion 126B on an opposite side may each be angularly coupled to a respective first and second central portion 122A, 122B. A separate back support portion 128 may also be coupled to the central support 122, e.g., either to the central portions 122A, 122B and/or fabric portion 124. Additionally, optional connecting conformable portions 134A, 134B may also be coupled to one or both sides of the back support portion 128 to respective support portions 126A, 126B.

The central portions 122A, 122B as well as support portions 126A, 126B and back support portion 128 may be comprised of a conformable material (e.g., malleable metal such as aluminum or plastics, foams, or any other bendable material) which is relative stiffer than the fabric portion 124 and inner or outer pads. The supporting portions may provide adequate support to a patient when the assembly 120 is placed, e.g., upon a mattress or platform, while enabling the assembly 120 to bend or flex into placement against the patient body when the patient lies upon the assembly 120. The support portions 126A, 126B may incorporate a corresponding first conformable portion 130A and second conformable portion 130B fabricated from a stretchable or distendible material such as a mesh or fabric which is supported by one or more adjustable straps 132 (e.g., straps with hook-and-loop fastening portions) coupling the conformable portions 130A, 130B to their respective support portions 126A, 126B. The flexibility of the conformable portions 130A, 130B may enable the shell assembly to shape or conform more closely to the patient body and may also provide for enhanced comfort.

Because the positioning of the conformable portions 130A, 130B against the patient body may be adjusted, a correlation may be formed between the amount of squeezing or tightening of the assembly 120 upon the patient body and the amount of pressure provided beneath the patient body.

For example, if the conformable portions 130A, 130B are squeezed against the patient body a higher pressure can be generated resulting in tightness against the body. This tightness is a variable which can be calculated based on various factors such as the patient's weight, height, etc. Additionally, the pressure can also be correlated to the fluid pressure inside of the inner and/or outer pads.

The back support portion 128 may be coupled via a flexible hinge portion 136 which allows the back support portion 128 to be flexed or angled relative to the central support 122 which may allow the assembly to remain attached securely to the patient as they sit up or lie down. The adjustable straps 132 may also provide stability to the assembly and may also prevent or inhibit the support portions 126A, 126B from falling from the patient body.

Figure 15A:
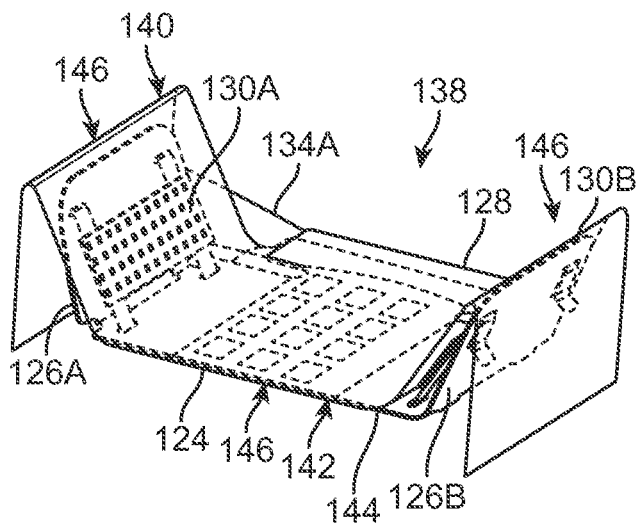
FIGS. 15A and 15B show perspective views of the outer shell assembly having a bladder assembly positioned upon the shell.
Figure 15B:
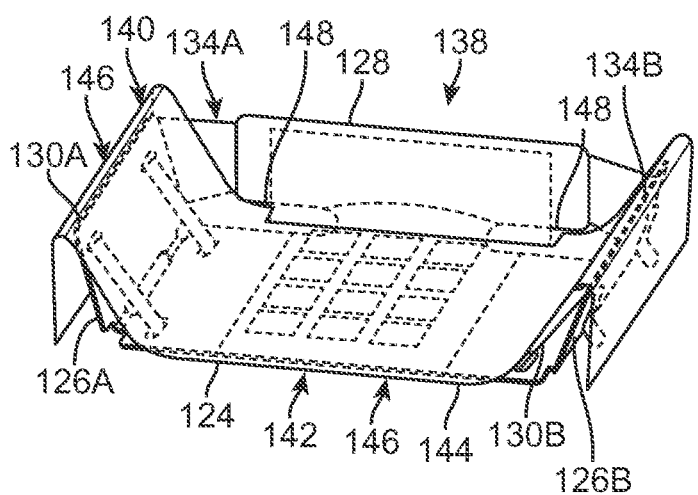

FIGS. 15A and 15B show perspective views of the assembly 120 having a bladder assembly 140 positioned upon the assembly 120 for supporting the patient body along the securement area 138, as described herein. The bladder assembly 140 may comprise the fluid assembly described above generally having an inner pad 142 surrounding the one or more pods 146 and an outer pad 144 which may either encompass the inner pad 142 and pods 146 or which may be laid upon the inner pad 142 and/or pods 146. Moreover, the pods 146 may be positioned along the central portion 122 and/or along one or both conformable portions 130A, 130B. Moreover, bladder assembly 140 may also incorporate one or more relief areas 148 which allow a portion of the bladder assembly 140 to bend or flex along with back support portion 128 when angled relative to the central portion 122.

Another variation of the outer shell support assembly is shown in the perspective view of FIG. 16. The assembly shown may be similarly be used with any of the fluid pad assemblies described herein (not shown for clarity purposes). In this variation, a central portion 122 may similarly be coupled to a back support portion 128 and support portions 126A, 126B. However, the support portions 126A, 126B may be further attached to the central portion 122 via one or more adjustable cords 150A, 150B, 150C, 150D (e.g., bungee cords). The flexible cords may help to maintain a position of support portions 126A, 126B relative to central portion 122, particularly when a patient is lying within or upon the shell assembly and pushing outwardly against the shell. The cords may be attached via attachment points 156 (e.g., along central portion 122) and extend over or through the support portions 126A, 126B through corresponding guide 152 and may further be removably coupled to the assembly via an adjustable mechanism 154 which allows for tension adjustment to cords to correspondingly adjust the amount of force or pressure of the support portions 126A, 126B against the patient's body.

FIGS. 17A to 17C show front and perspective views of yet another variation of the supporting shell assembly (the bladder assembly has been omitted for clarity). This variation may similarly include an outer shell assembly having a central portion 122 with respective support portions 126A, 126B angled relative to the central portion 122. However, this variation may incorporate columns 162 pivotably attached 164 to a platform 160 and extending into connection with one or more openings 166 within respective support portions 126A, 126B. The columns 162 may be pivoted via attachment 164 at a first end and into the one or more openings or receiving channels 166 at a second end to adjust an angle of respective support portions 126A, 12611 relative to the central portion 122.

Alternatively, the columns 162 themselves may be adjustable in their height to vary the angle of the support portions 126A, 126B relative to the central portion 122. For example, the columns 162 may be adjustably telescoping to vary their height or the columns 162 may be simply interchangeable between columns of different heights. Moreover, the outer shell assembly shown may incorporate any of the other features described herein in any number of combinations. For instance, the central portion 122 may incorporate a meshed portion and/or a back support portion as well as any number of different combinations of the bladder assembly having the one or more pods positioned variously.

FIG. 18 shows a perspective view of yet another variation where the central portion 122 may incorporate respective composite assemblies 170A, 170B which are adjustably configurable. The composite assembly may generally include a number of individual support elements 172 (e.g. plastic, metal, foam, etc.) which are connected to one another along respective longitudinal axes 176, 178 in an alternating pattern. A tensioning member 174 such as a wire, screw, etc., may be passed through each end of the support elements 172 along the longitudinal axes 176, 178 with a tightening member 180 coupled at the ends of the tensioning member 174. Loosening of the tightening member 180 may allow for the rotation of the individual support elements 172 with respect to one another such that the composite assemblies 170A, 170B may be conformed desirably to the patient's body to closely follow the anatomy. Once a desirable configuration is conformed, the tightening member 180 may be tightened to force or urge the support elements 172 against one another such that the composite assemblies 170A, 170B maintain their configurations.

FIGS. 19A to 19C show perspective and side views of yet another outer shell assembly which incorporates a central support portion 190 with respective first and second support portions 192A, 192B. The support portions 192A, 192B may generally comprise first and second angled supports 194A, 194B which are adjustably secured to respective first and second adjustable supports 196A, 196B which may be rotatable about first and second pivots 200A, 200B. The adjustable supports 196A, 196B may each support respective first and second conformable portions 198A, 198B which provide a surface for supporting the bladder assembly against the patient. Moreover, the adjustable supports 196A, 196B may be pivoted relative to the angled supports 194A, 194B to place the conformable portions 198A, 198B into contact with the patient's body. Once suitably positioned, the angled supports 194A, 194B and adjustable supports 196A 196B may be locked in their configuration via securement pins 202A, 202B through any number of adjustment openings 204A, 204B.

Figure 20A:
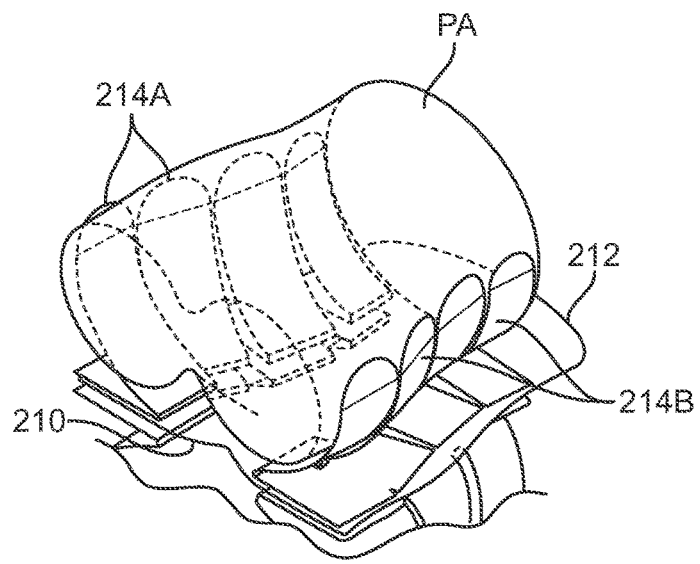
FIGS. 20A and 20B show perspective and side views of another variation where the conforming supports may extend in a curved or arcuate manner from the central support portion.
Figure 20B:
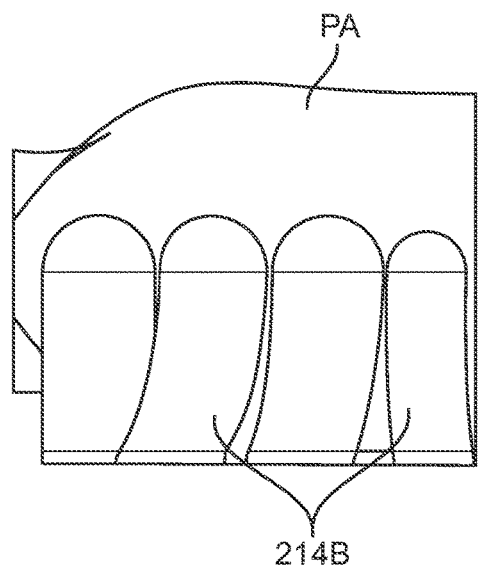

In yet another variation of the outer shell assembly, FIGS. 20A and 20B show perspective and side views of a variation where a central support portion 210 and optional back support portion 212 may include a number of conforming supports 214A, 214B which may extend in a curved or arcuate manner from the central support portion 210 in a shaped shell configuration. The conforming supports 214A, 214B may be shaped to conform more closely to the patient body PA while providing a stiff supporting platform for positioning the bladder assembly against the patient body PA. Moreover, the conforming supports 214A, 214B may be extend in strips or members which are shaped, e.g., like flower petals, and the supports may be secured in place using any number of securement mechanisms, e.g., friction hinge mechanisms, electromechanical locking systems, hydraulic locking systems, magnetic locking systems, electro or magneto-rheological locking systems, etc.

Figure 21A:
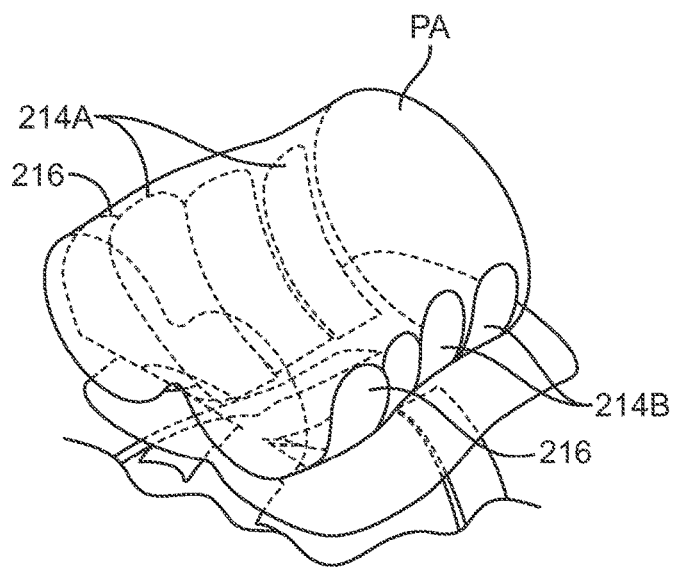
FIGS. 21A and 21B show perspective and side views of another variation where the curved or arcuate conforming supports may overlap one another.
Figure 21B:
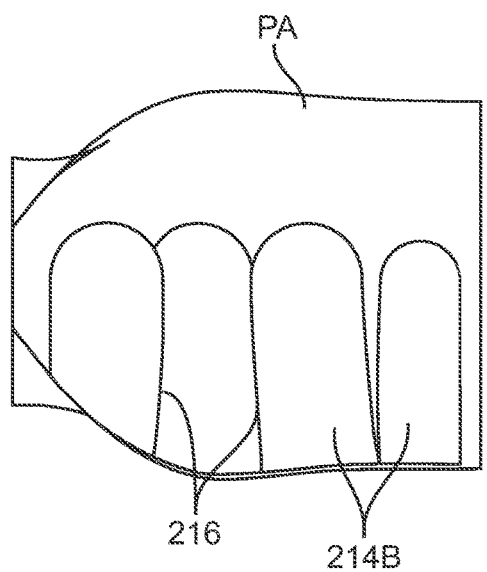

FIGS. 21A and 21B show perspective and side views of another variation similar to the embodiment of FIGS. 20A and 20B. In this variation, one or more of the conforming supports 214A, 214B which are adjacent to one another may define overlapping regions 216 to provide a more contiguous platform.

Figure 22:
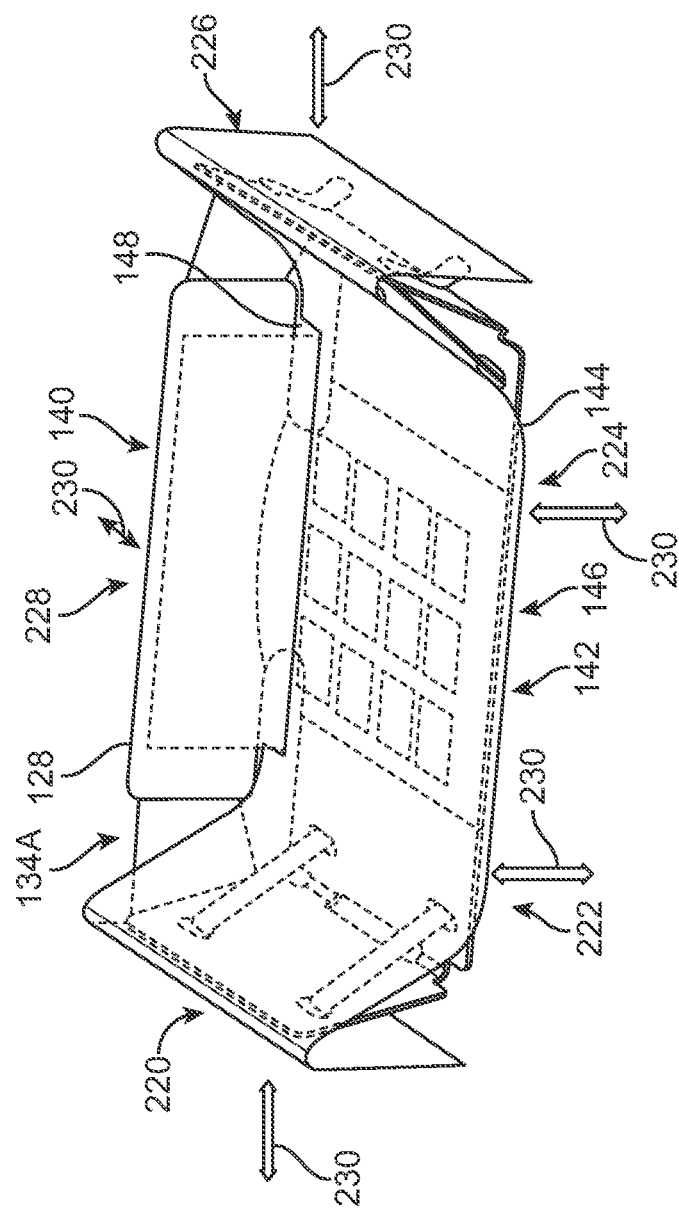
FIG. 22 shows a perspective view of an outer shell variation which may incorporate one or more zones throughout various regions of the shell which may selectively or simultaneously squeeze, vibrate, or otherwise actuate.

Although various outer shell assemblies are disclosed, various features between the different embodiments are intended to be utilized in any number of combinations as desired and as practicable. For example, the variation shown in FIG. 20A may incorporate any number of the support adjustment mechanisms such as columns, rotatable members, etc., in combination for adjusting the supports. Likewise, the features of the outer shell assembly shown in FIG. 22 may be used in combination with any of the outer shell assemblies or pad assemblies described herein. The outer shell assembly may incorporate one or more zones 220, 222, 224, 226, 228 throughout various regions of the shell which may selectively or simultaneously squeeze, vibrate, or otherwise actuate, e.g., in the direction of actuation, vibration, or pulsation 230. These selective zones may vibrate at a selected frequency and/or amplitude and may be actuated at fixed intervals or times.

This actuation 230 can be automated based on a fixed interval/amplitude schedule or can be part of a closed loop system where depending on feedback from certain sensors (e.g., pressure, force, humidity, temperature, etc.) the outer shell can selectively be squeezed or vibrated by a certain amount to ensure that the sensor reading reach a predetermined levels. Moreover, each of the zones can be programmed to vibrate or squeeze in or out selectively or in some combination with each other. These zones may be actuated to squeeze against the patient body just enough to allow for pushing some of the fluid contained within the pad and/or pods, for example, below the sacrum and create a thin layer of fluid below the sacrum.

Moreover, the outer shell may be sized to fit, e.g., more than 95% of a target population, or the outer shell can be designed to be a one-size-fit-all or can be made in two or more different sizes to fit most of the patient population. This sizing can be applied to any of the various outer shell and pad assemblies described herein.

Figure 23A:
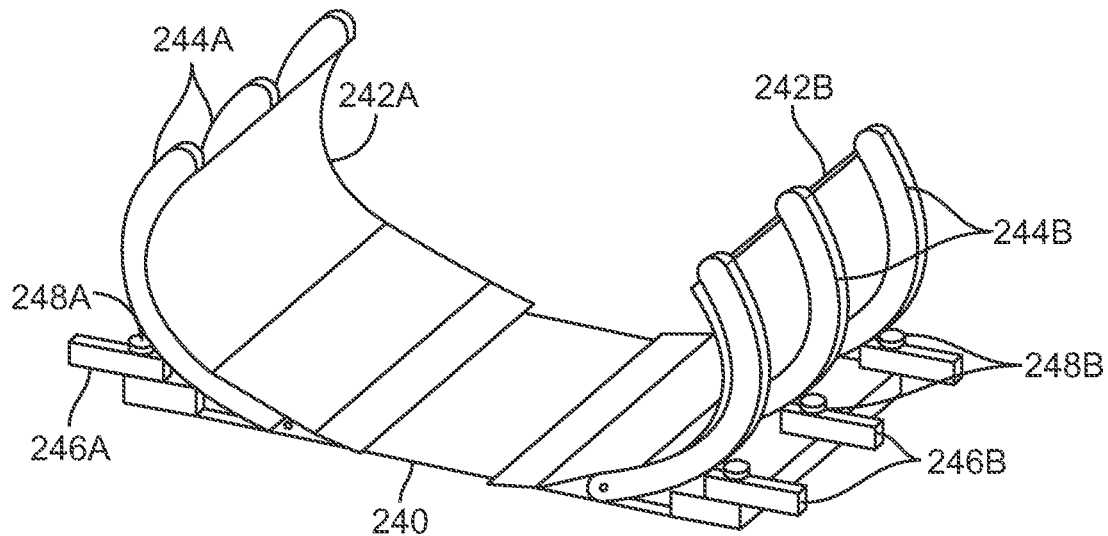
FIGS. 23A and 23B show perspective views of yet another outer shell assembly which has a central support portion with articulating and adjustable support portions.
Figure 23B:
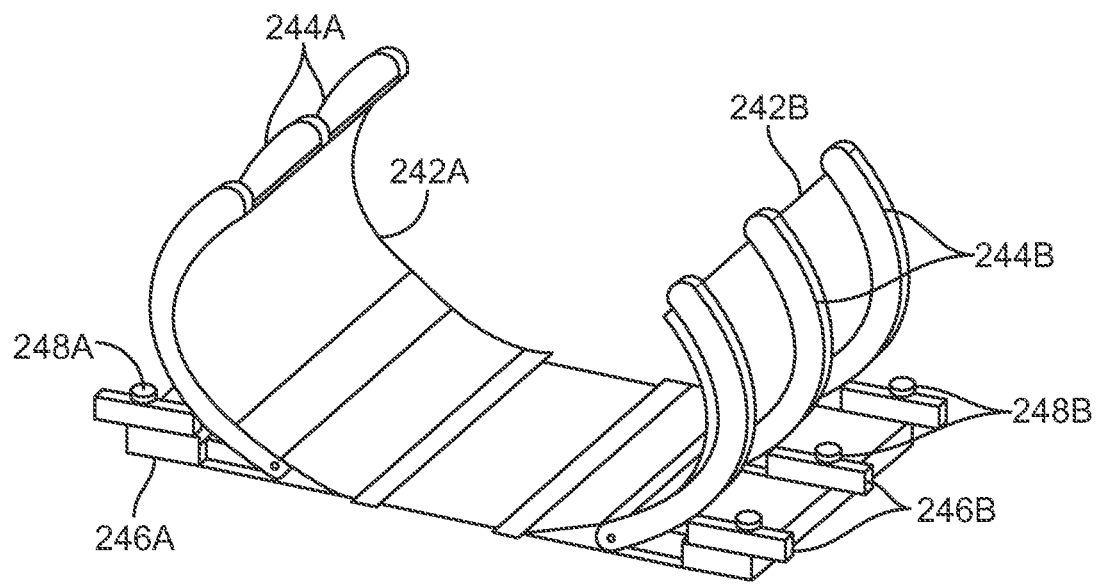

FIGS. 23A and 23B show perspective views of yet another outer shell assembly which has a central support portion 240 with articulating and adjustable support portions. The first and second conforming supports 242A, 242B may be anchored to the central support portion 240 and extend in a curved or arcuate shape for conforming more closely against the patient's body. The supports 242A, 242B may each integrate one or more support members 244A, 244B which are adjacent to respective sliding supports 246A, 246B which may be tuned to push in or out relative to the central support portion 240 to adjust a rotation or bend radius of each support 244A, 244B independently of one another or simultaneously with each support 244A, 244B. Each of the sliding supports 246A, 246B may be mounted on independent blocks which may be wedged independent to adjust a location of the supports 244A, 244B. Additionally, the sliding supports 246A, 246B may incorporate respective adjustable locks 248A, 248B to secure a position of the support to maintain a configuration of the conforming supports 242A, 242B.

As illustrated in FIG. 23A the sliding supports 246A, 246B may be extended to position the conforming supports 242A, 242B in an opened configuration, e.g., for receiving a patient body. Once the patient has laid down within the assembly, the sliding supports 246A, 246B may be urged inward to place the conforming supports 242A, 242B against the patient body, as shown in FIG. 23B.

Figure 24A:
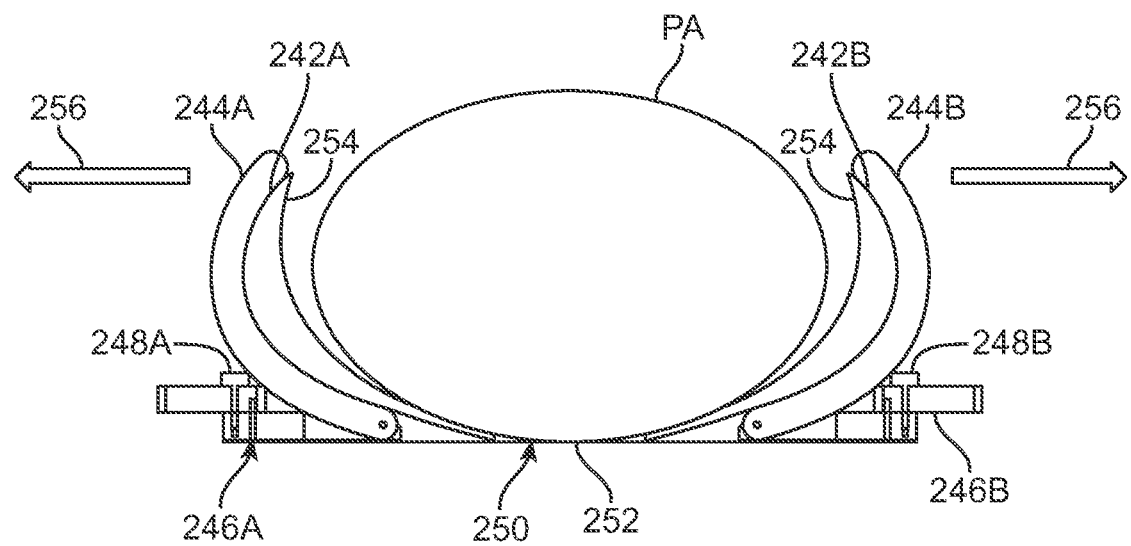
FIGS. 24A and 24B show end views of the conforming supports when urged against the patient body.
Figure 24B:
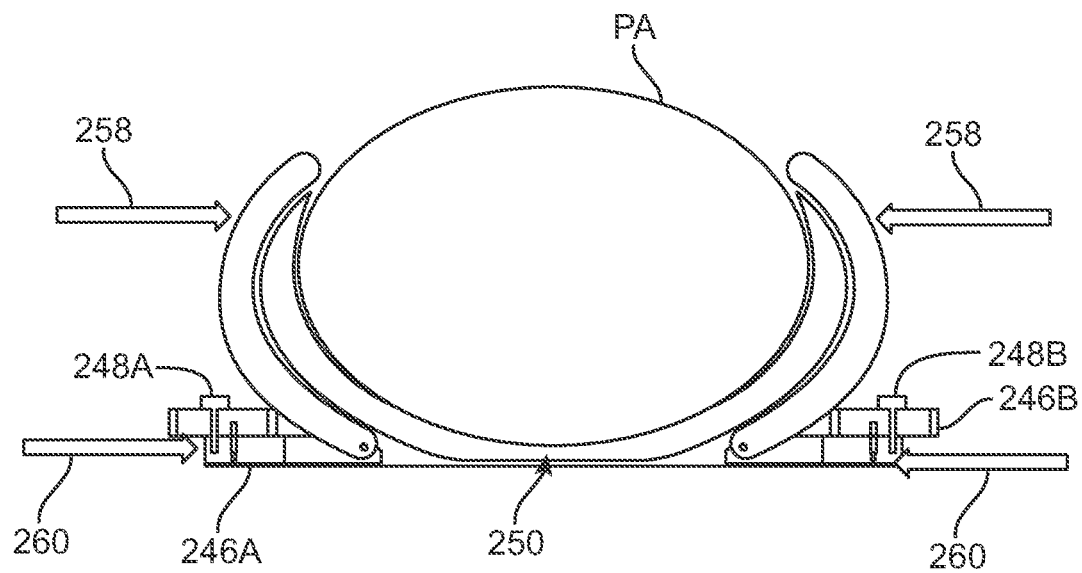

FIGS. 24A and 24B show end views of the conforming supports 242A, 242B when urged against the patient body PA. As previously described, any of the pad assemblies described herein may be used with this outer shell variation. FIG. 24A illustrates how the bladder assembly may bottom out when a patient lies upon the outer pad 250 and is unsupported by the conforming supports 242A, 242B, as shown by the outward direction of support movement 256. As illustrated, the patient body PA may compress the central portion of the pad resulting in a bottomed-out section 252 where the fluid within the pad form bulging sections 254 along the sides when displaced. Yet when the conforming supports 242A, 242B are held or maintained against the patient body PA, as indicated by the direction of support movement 258 and locked in place by the sliding supports 246A, 246B, as indicated by the direction of movement 260, the fluid within the pad 250 along the previously bulging sections 254 may be "squeezed" or redistributed to flow beneath the patient body PA, as shown in FIG. 24B, to eliminate bottom-out section 252 and bulging sections 254.

Figure 24C:
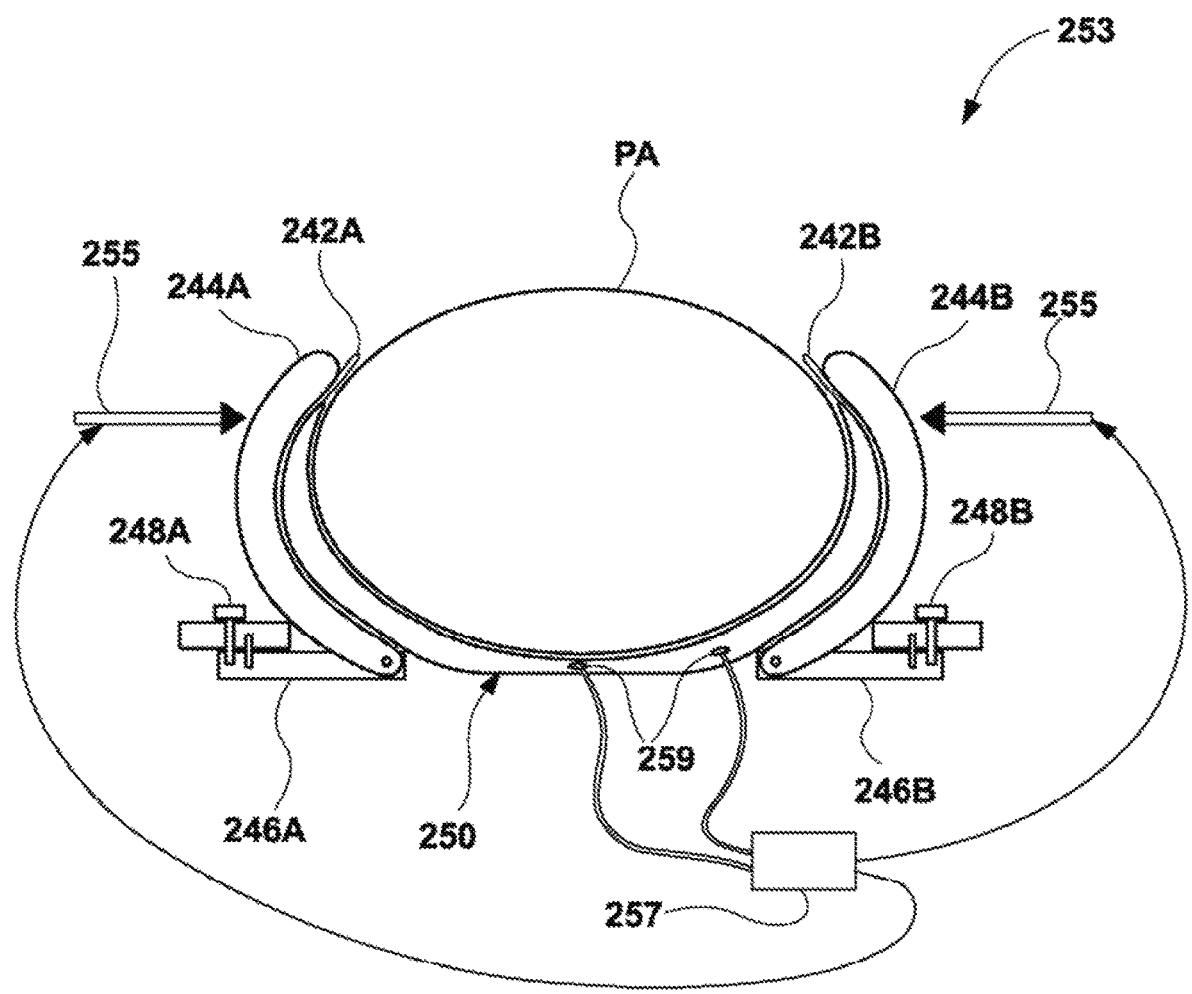
FIG. 24C also shows a feedback loop that may automatically adjust one or both of the conforming supports.

As shown in FIG. 24C one or more pressure sensors 259 may be disposed to detect bottoming out of the pad(s) and/or pods. If one area is bottoming out, then the pressure difference between the two sensors would be higher. The one or more pressure sensors 259 may be in contact with the pad(s) and/or pods. One algorithm that can be used to detect bottoming out is to calculate the difference between two pressure sensors in contact with the fluid inside the bladder assembly, one of these pressure sensors can be located in a region that is expected to bottom out and the other pressure sensor can be located in a region that is not expected to bottom out. If neither area surrounding the pressure sensor is bottoming out, the pressure difference between the two sensors will be small due to the ability of the fluid to equalize pressure within the bladder assembly. The one or more pressure sensors 259 can be used in a feedback loop with a controller 257 that controls an automated applied force 255 to squeeze the conforming supports 242A, 242B such that the patient body PA does not bottom out the pad(s) and/or pods when the patient sits or lies on the automated cushion assembly 253.

The redistribution of fluid within the pad 250 may help to reduce any pressure that may result below any bony prominences of the patient body. As the conforming supports 242A, 242B may be rotated or turned to conform more closely to the patient body PA, the fluid distribution may be improved to further reduce pressure beneath the patient.

Figure 25:
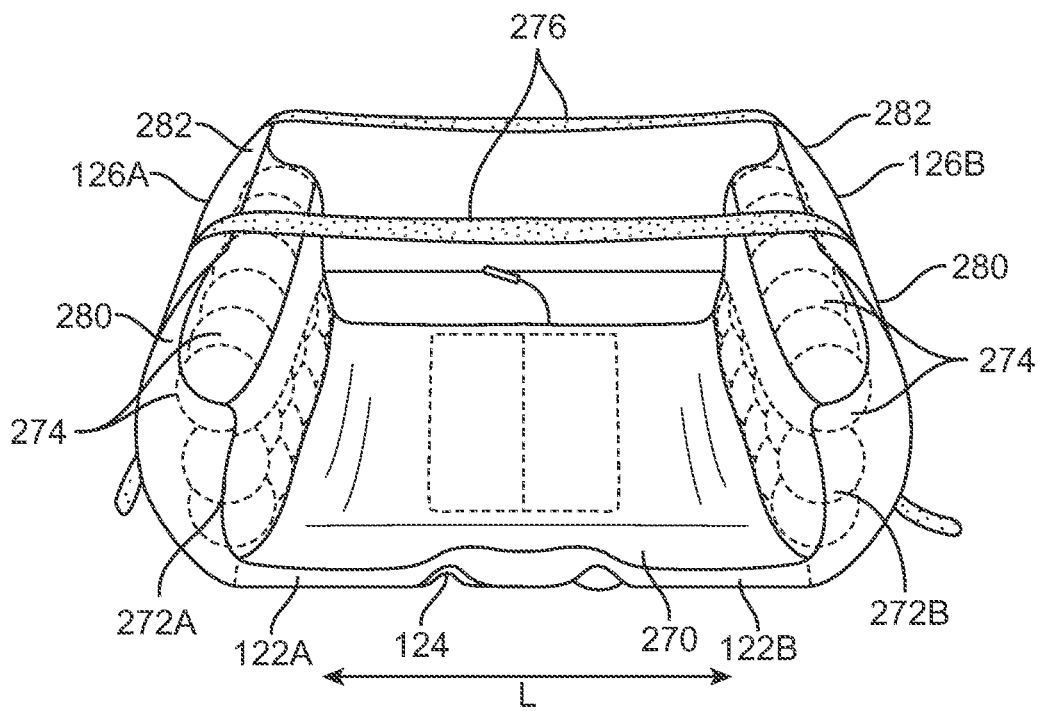
FIG. 25 shows a perspective end view of another outer shell assembly having support portions pivotably attached to respective central portions.

In yet another variation, FIG. 25 shows a perspective end view of another outer shell assembly having support portions 126A, 126B pivotably attached to respective central portions 122A, 122B which may have a fabric portion 124 attached between. This variation may be configured such that the support portions 126A, 126B are arranged to be tangential relative to the patient body placed between. The central portions 122A, 122B and fabric portion 124 may remain flattened beneath the patient's body while the support portions 126A, 126B may extend tangentially and conform to the patient's body. The support portions 126A, 126B may further have a retaining lip or portion 282 pivotably attached via a respective hinge or pivot 280 which are able to be further angled relative to the patient's body, e.g., bent towards the patient's thigh on upon the thigh, to further squeeze or urge fluid within the bladder assembly 270 beneath the patient body and to further prevent fluid from bulging along the sides of the bladder assembly 270.

Alternatively, the retaining lip or portion 282 may omit any hinge or pivot and may simply comprise a flexible extension of the support portions 126A, 126B. Thus, the outer shell assembly and bladder assembly may be designed to mimic the natural shape of the patient's hip region.

To further secure the outer shell assembly to the patient body, one or more adjustable straps 276 may be extend around the open portion of the shell assembly and also around the patient body to ensure that the assembly and retaining lip or portions 282 remain closely conformed and secured to the body.

The variation of the bladder assembly 270 shown placed upon the outer shell assembly may incorporate the inner pad and one or more pods throughout the entire bladder assembly, e.g., along the central portion as well as along the sides. Although, in the variation shown, the inner pads 272A, 272B may be positioned within or beneath or above the assembly 270 along the support portions 126A, 126B. The inner pads 272A, 272B may also contain one or more of the pods 274 within such that the pods 274 are in contact with one another to allow for the transmission of fluid pressure between the pods 274 while remaining contained (or restrained) within their respective inner pads 272A, 272B. The one or more pods 274 may line support portions 126A, 126B and perform the function of achieving conformity with the patient body as well as redirect the fluid below the load bearing region of the patient.

Figure 26:
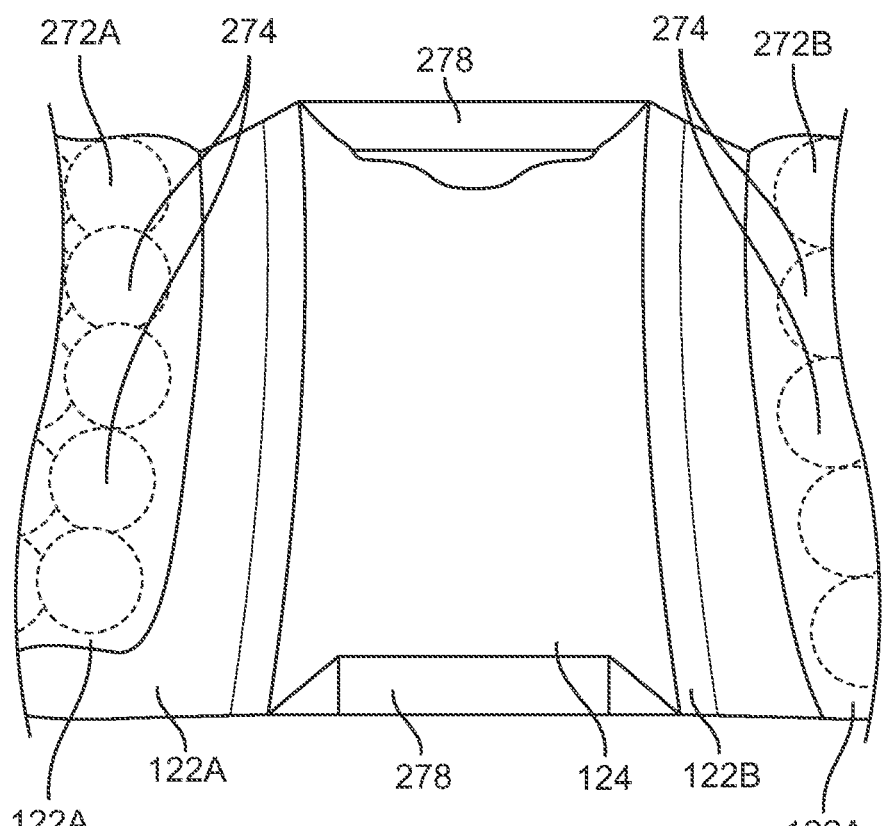
FIG. 26 shows a detail top view of the outer shell assembly having one or more adjustment straps or rails.

While the central portions 122A, 122B may have fabric portion 124 attached between, the two portions 122A, 122B may also be connected by one or more adjustment straps or rails 278 which may limit the movement between two portions 122A, 122B, as shown in the detail top view of FIG. 26 (with part of the bladder assembly 270 removed for clarity). Additionally, the straps or rails 278 may be adjustable to size the distance L between the supports 122A, 122B to more closely conform the shell assembly to the patient body. The distance L may be readjusted to the patient body, e.g., by using a sizing tool, or adjusted after the patient lies down upon the bladder and outer shell assembly using, e.g., a winch type mechanism or any other adjustment mechanism.

Figure 27A:
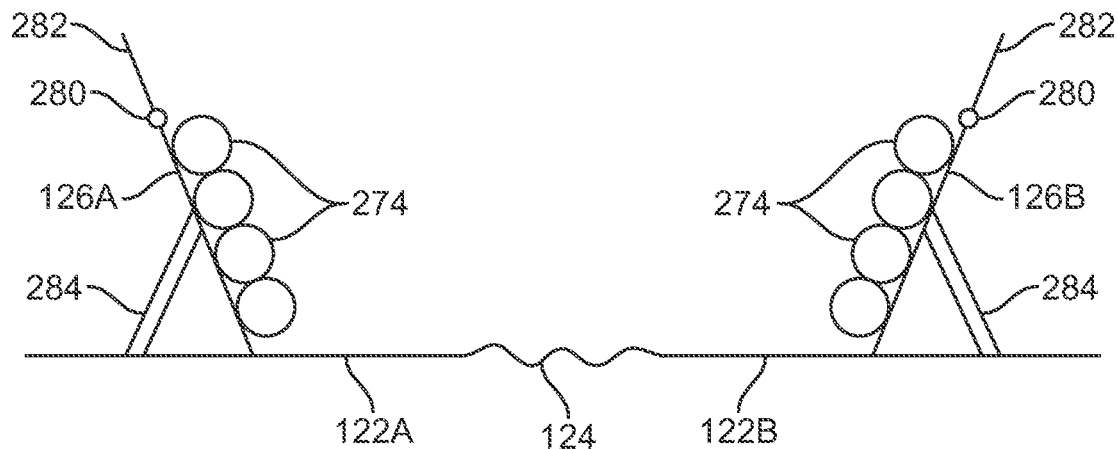
FIGS. 27A and 27B show schematic end views of the outer shell assembly to illustrate how the support portions and retaining lip or portions may be wrapped or placed about a patient's body.
Figure 27B:
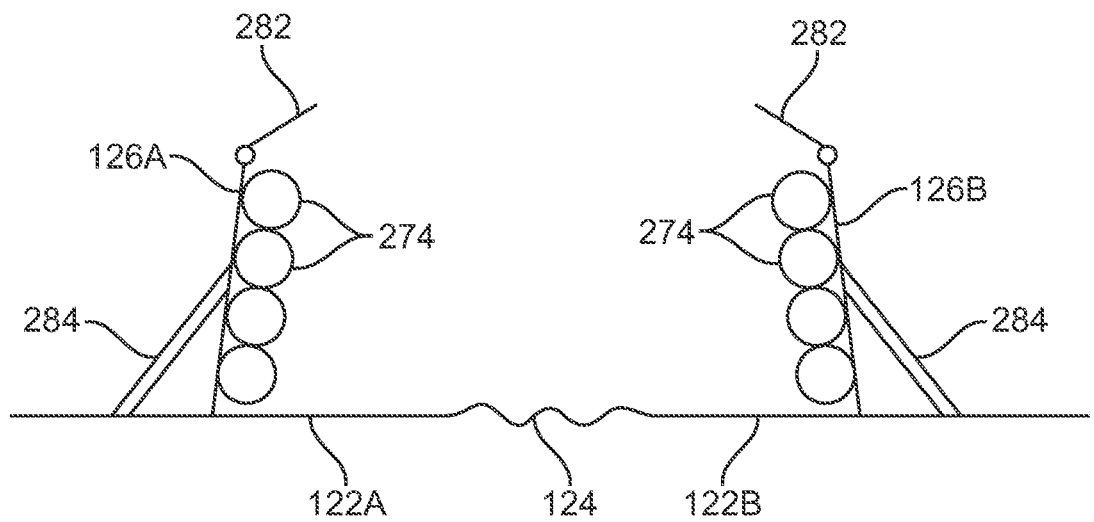

FIGS. 27A and 27B show schematic end views of the outer shell assembly to illustrate how the support portions 126A, 126B and retaining lip or portions 282 may be wrapped or placed about a patient's body. As shown in FIG. 27A, the support portions 126A, 126B may be seen in an open configuration (while optionally supported by supports 284) for receiving a patient body. The one or more pods 274 are shown placed along the support portions 126A, 126B only although they may be placed along the central portion directly beneath the patient's body as well. The inner pads and remaining bladder assembly (such as the outer pad) are not shown only for clarity. Once the patient has been positioned within the assembly, the support portions 126A, 126B may be placed into contact against the sides of the patient's body such that one or more pods 274 are placed into supporting contact as well, as shown in FIG. 27B. The retaining lip or portions 282 may be conformed, bent, or pivoted about their respective hinges (if hinges are used since they may be omitted entirely) such that the portions 282 are further wrapped around the patient's body, such as around their hips or thighs, to further conform against the body as well as to further prevent the fluid pressure or movement of the pods 274 from extending or bulging above the patient's body. The entire assembly may be maintained in position and secured to the patient's body optionally by the use of the one or more adjustable straps 276 described above although the use of straps may be omitted entirely.

The retaining lip or portions 282 may be configured into various geometries as well. For instance, rather than being flattened segments, the portions 282 may be configured into curved sections where the one or more pods 274 and/or bladder assembly terminate within the curved ends. Moreover, the retaining lip or portions 282 may further incorporate a compression mechanism (such as screw-driven mechanisms, clamps, secondary fluid bladders, etc.) to further increase the compression of the portions 282 upon the pods 274 and/or bladder assembly.

The pressure of fluid within the bladder assembly can be an indicator of the optimal "squeeze" or compression of the support portions 126A, 126B on the patient's body. For instance, based on experimental testing, an optimal pressure range may be determined for each person based on his/her height and weight. If the fluid pressure is too low, this can be an indication of insufficient compression by the support portions 126A, 126B (or insufficient tension in the adjustable straps 276 if the straps are used to squeeze the support portions 126A, 126B upon the patient). Insufficient pressure within the bladder assembly can potentially lead to minimal fluid below the patient leading to bottoming out of the bladder assembly beneath the patient and thus causing localized regions of high pressure. On the other hand, if the fluid pressure within the bladder assembly is too high, this can be an indication of excessive compression of the support portions 126A, 126B upon the patient. Over pressurization can lead to higher pressure readings on the areas where the outer shell assembly is squeezed upon the patient and/or higher pressures on the load bearing region of the body because the downward force on the body is increased. An optimal tension or pressure algorithm can thus be developed for an individual based upon advice of the healthcare provider on the optimal setting.

Such an algorithm can be derived based on a number of parameters but in one example, the following parameters may be taken into account. For example, weight of the patient; height of the patient; width of the patient's hip; gender; estimated sacrum weight; and optimal fluid pressure for the sacrum weight (provided by graphs, lookup tables, or other methods).

Moreover, the pressure of the fluid within the bladder assembly can be measured in different ways as well. For instance, fluid pressure can be determined using, e.g., a pressure gauge which can be removed or attached to the person, a turkey-popper type indicator, any other similar pressure gauges, etc. The internal bladder pressure is simply one indicator which may be used to monitor pressure. Other indicators which may also be used in the alternative or in addition to the internal bladder pressure may optionally utilize measurement of e.g., strap tension, squeeze force/pressure along the support portions (e.g., by attaching pressure/force sensors), as well as other mechanisms.

Figure 28:
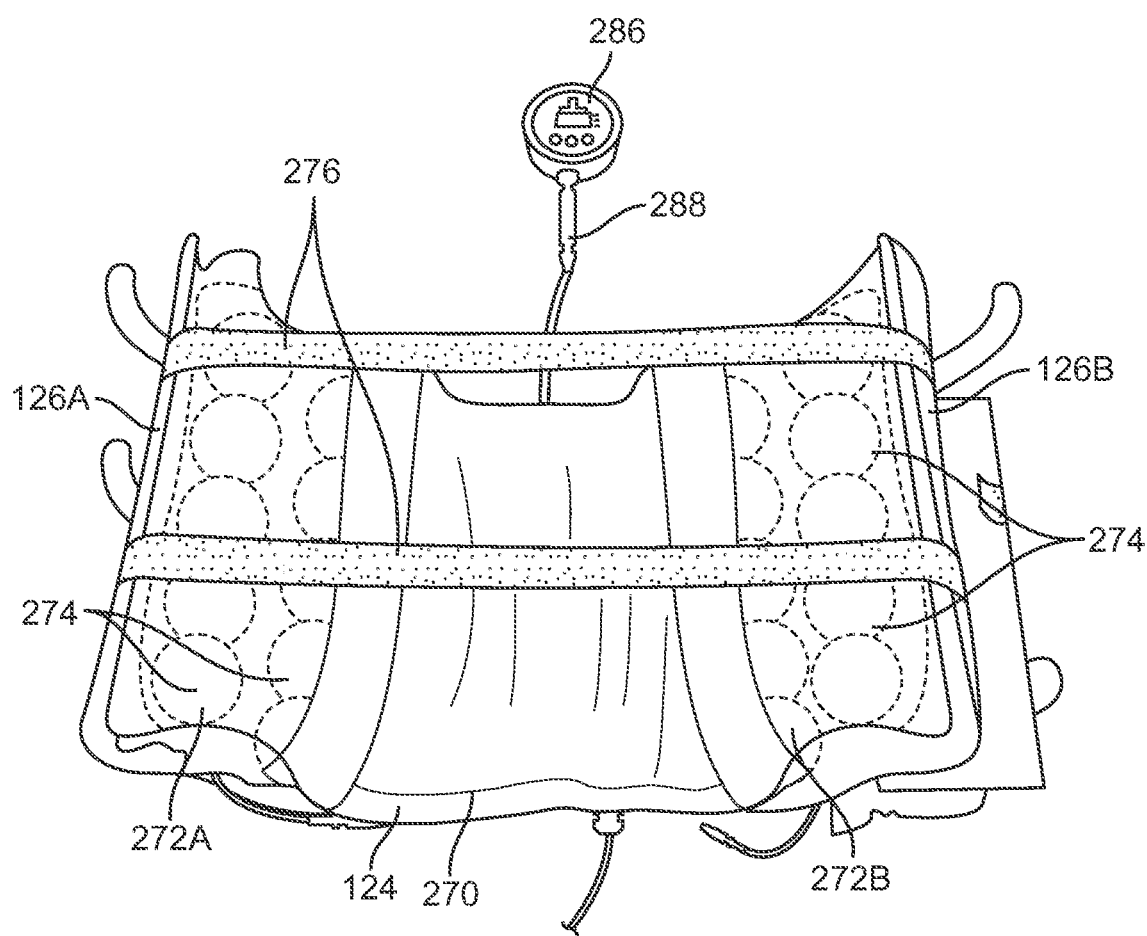
FIG. 28 shows a perspective view of another variation of an outer shell assembly having a bladder assembly incorporating a pressure gauge.

One variation is shown in perspective view of FIG. 28 which illustrates an outer shell assembly having a bladder assembly with a pressure gauge 286 fluidly coupled by a fluid line 288 for determining the pressure of the fluid, for instance, before and/or after the assembly is secured to a patient.

Hence, securing the outer shell assembly to a patient body may be accomplished in number of different ways. One example may include the following steps: (1) the nurse or health care provider may size the patient and notes the weight and height of the patient; (2) the nurse or health care provider may set the distance between the central portions 122A, 122B; (3) the nurse or health care provider may slide the assembly beneath the patient body; (4) the nurse or health care provider may then initially adjust the support portions 126A, 126B against the patient's body while monitoring the pressure indicator until an optimal fluid pressure is reached for the patient based on their parameters such as their height and weight; and (5) the nurse or health care provider may then readjust the outer shell assembly, bladder assembly, or fluid pressure, etc. based on patient comfort and feedback, if provided.

Figure 29:
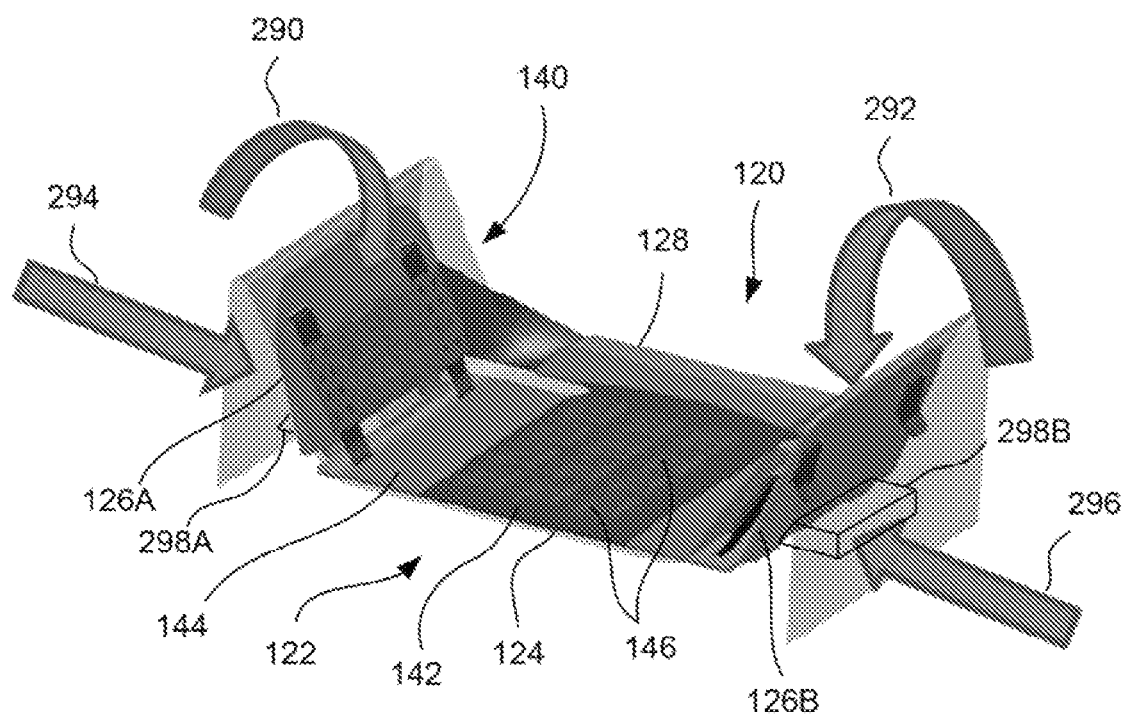
FIG. 29 shows a perspective view of the outer shell assembly and bladder assembly illustrating how the different regions or portions of the outer shell assembly may be adjusted relative to the patient body.

In adjusting the outer shell assembly relative to the patient body, the system may be automatically operable to adjust one or more regions or segments of the assembly in either a completely automated or semi-automated manner. FIG. 29 shows how the different regions or portions of the outer shell assembly may be adjusted to minimize the pressure placed upon or imparted upon the patient body. One or more regions of the outer shell assembly and/or bladder assembly may incorporate any number of pressure indicators which are in communication with a controller. The controller may actively monitor these various regions of pressure and accordingly adjust the assembly to minimize or maintain the pressure imparted upon the patient body. e.g., below a predetermined threshold.

The adjustments to the assembly may be done automatically or semi-automatically when a nurse or care provider adjusts or places the assembly upon the patient. The system may accordingly adjust the device automatically relative to the patient body or it may provide feedback to the nurse or care provider to make the adjustments.

In adjusting the outer shell assembly 120 and/or bladder assembly 140, the various regions of the assembly 120 may be adjusted, e.g., support portions 126A, 126B; conformable portions 130A, 130B back support portion 128; etc., relative to the central portion 122 as indicated by the direction of movement/rotation 290, 292 and/or direction of movement/actuation 294, 296. These adjustments may be accomplished using any of the various adjustment features described herein.

In the case of a semi-automated system, the one or more regions of the assembly 120 may be adjusted by the nurse or care provider. Additionally and/or alternatively, in the case of a frilly automated system, one or more actuators 298A, 298B (e.g., motors, pneumatic or hydraulic actuators, etc.) coupled to the various regions may be used to make the appropriate adjustments.

In monitoring the various regions of pressure over the patient body, any of the pressure indicators described herein may be used. Additionally and/or alternatively, various other pressure or force sensors (e.g., resistive or capacitive type sensors) may be placed in particular regions of the patient body such as those areas of bony prominences such as the sacrum and trochanter. Optionally, any number of sensors may be positioned in a matrix over the entire surface of the outer shell assembly or bladder assembly or a separate pressure indicator. In any of these variations, the one or more sensors may be placed in communication with a controller which can be programmed with a preset pressure profile.

Figure 30:
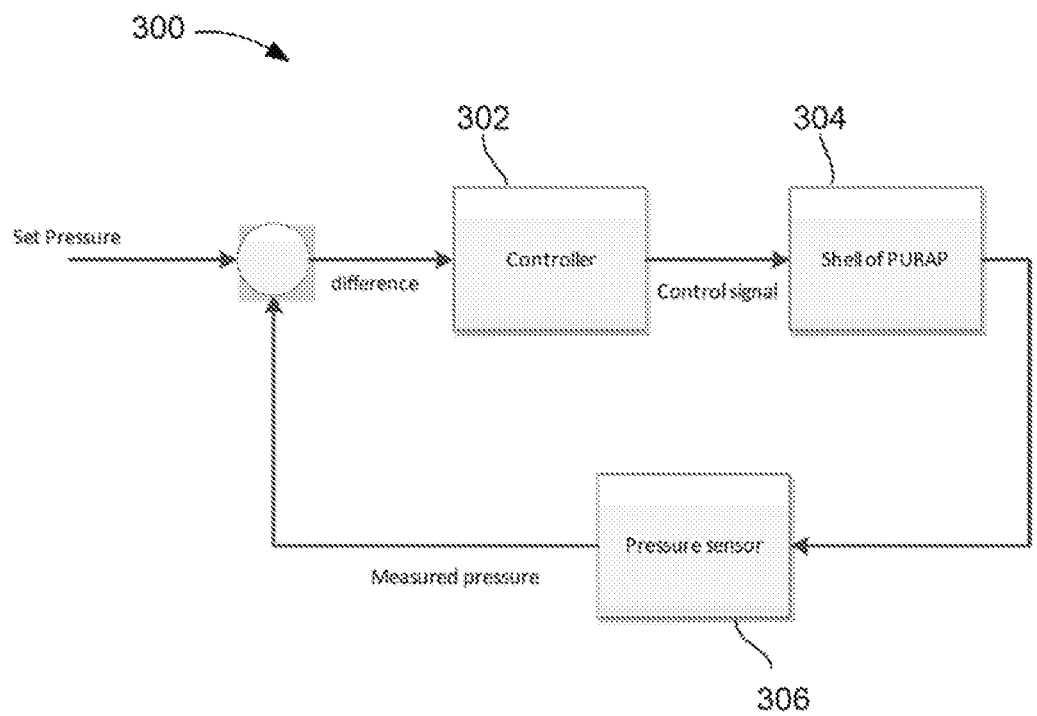
FIG. 30 shows an example of a feedback loop which may be implemented upon the system.

An example of a feedback loop 300 which can be used with the system is shown in FIG. 30. A preset pressure level may be initially programmed into the controller 302 which may monitor and calculate any differences in the monitored pressure levels via any embodiment of the pressure sensor 306 in contact or communication with any region of the patient body. The measured pressure by the pressure sensors 306 may be compared by the controller 302 to determine whether the particular measured pressure is beyond the set pressure level. If not, then the controller 302 may simply maintain a position of the assembly relative to the patient body; however, if a calculated difference is beyond the set pressure level, then the controller 302 may send a control signal to the relative actuator to adjust the relevant portion of the outer shell 304 until the measured pressure levels fall within the predetermined limits. Alternatively, the controller 302 may provide an indication, alert, and/or message displayed to the nurse or care provider to adjust a particular portion of the outer shell 304 until the monitored pressure falls within the predetermined limits.

In this and other variations, various types of pressure sensors may be used (e.g., (resistive, capacitive, piezo-based, hydraulic, etc.). Alternatively, force sensors may also be utilized, e.g., FlexiForce® Sensors (Tekscan, Inc., Boston, Mass.). In other variation, other types of sensors may also be utilized, e.g., skin oxygen sensors or skin perfusion indicators, temperature sensors, humidity sensors, heart rate sensors, breathing sensors, accelerometers, gyroscopes, etc.

Figure 31A:
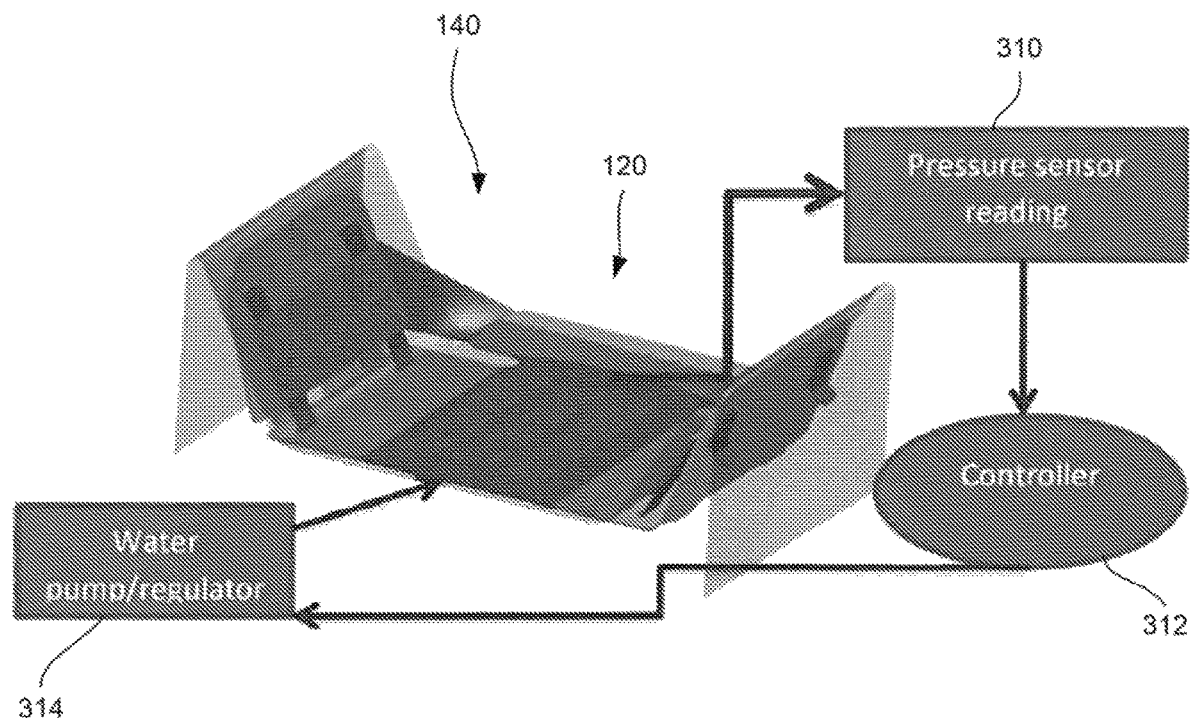
FIGS. 31A and 31B schematically show variations for implementing feedback loops into the system.

FIG. 31A schematically illustrates one variation for implementing a feedback loop to the outer shell assembly 120 and/or bladder assembly 140. As previously described, one or more pressure sensors may be positioned within the bladder assembly 140 or in communication with the bladder assembly 140 to provide one or more pressure sensor readings 310 at one or more corresponding positions over the bladder assembly 140. These readings 310 may be transmitted to the controller 312 which may be optionally programmed to compare the measured readings 310 relative to a preprogrammed value. If the controller 312 detects a drop in the pressure beyond the preset limits, the controller 312 may send a signal to one or more pumps or regulators 314 in communication with the bladder assembly 140 (e.g., in communication with either the inner pad 142, outer pad 144, or the one or more pods 146, individually or collectively) to increase or decrease a volume of fluid within any one or all of the components of the bladder assembly 140 or particular regions or portions of the bladder assembly 140.

Figure 31B:
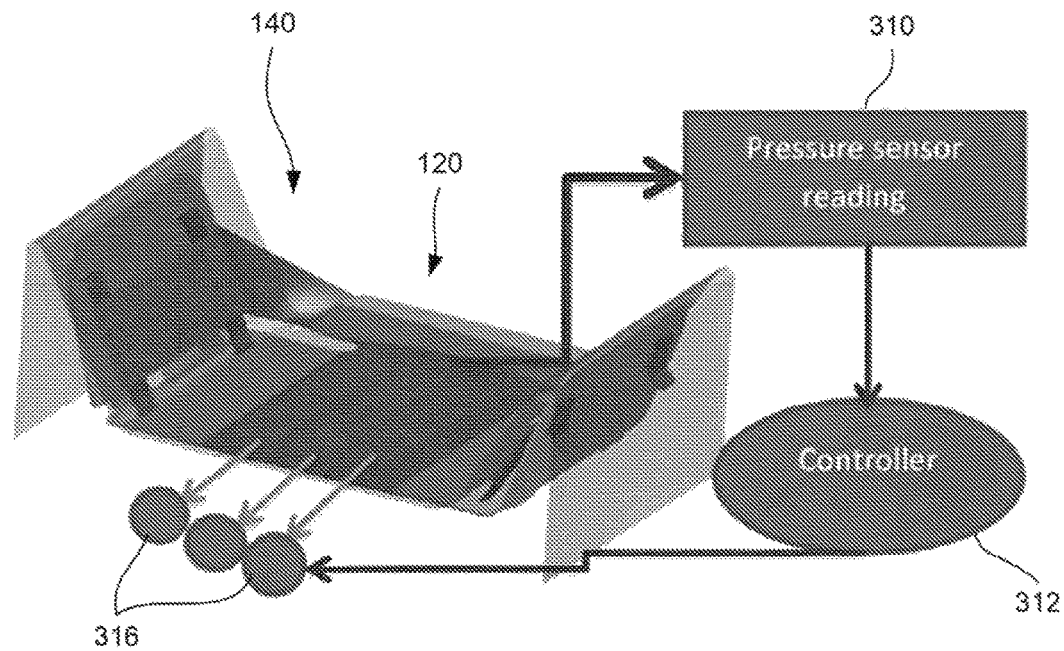

Additionally and/or alternatively, the pump or regulator 314 can instead selectively direct fluid within the bladder assembly 140 to areas of sensed high pressures from areas of sensed low pressures. This selective and directional fluid flow can be accomplished by any number of mechanisms. For instance, another variation is schematically illustrated in FIG. 31B which shows how the controller 312 may be in communication with one or more individual fluid pods 316 (e.g., positioned along the central portion beneath the patient body) which may each be selectively inflated or deflated by adding or removing fluids such as air or water. The relative inflation and deflation of the one or more pods 316 may be used to control the amount of fluid present in the portion of the main bladder above the pods 316.

Figure 32A:
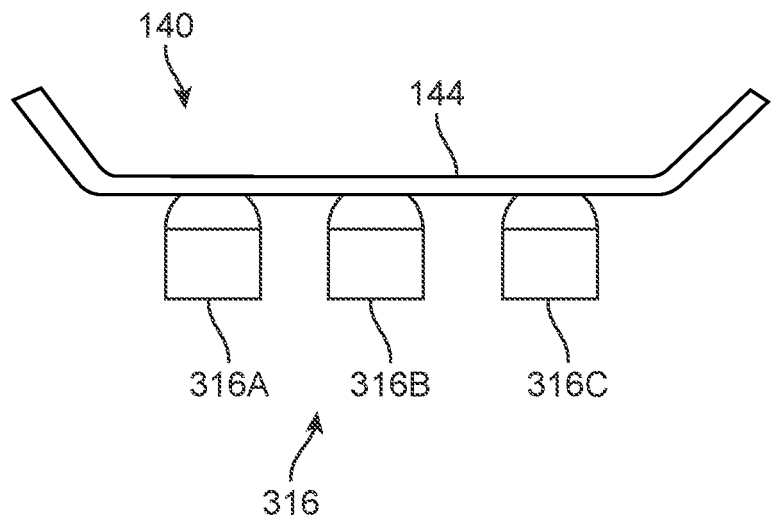
FIGS. 32A and 32B show exemplary side views illustrating how individual fluid pods may be selectively inflated and/or deflated to direct fluid through the fluid pad.
Figure 32B:
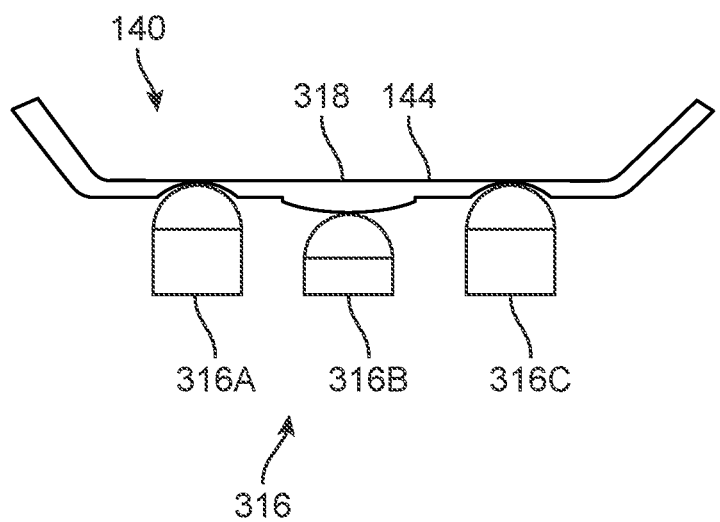

FIGS. 32A and 32B show exemplary side views of how the individual fluid pods 316A, 316B, 316C may be initially inflated at the same pressure such that the outer pad 144 above is maintained at a uniform level for supporting the patient body (the inner pad is omitted for clarity although the inner pad may be omitted entirely in this variation). As the controller 312 detects a region 318 of high pressure exerted upon the bladder assembly 140 by the patient body, the fluid pod 316B directly below that high pressure region may be deflated while the surrounding pods 316A, 316C adjacent to pod 316B may inflated to direct the fluid within the pad 144 towards the high pressure region to provide additional support to the patient body. While one example is illustrated for directing the fluid beneath regions of the patient body, alternative mechanisms may also be used in other variations.

Figure 33:
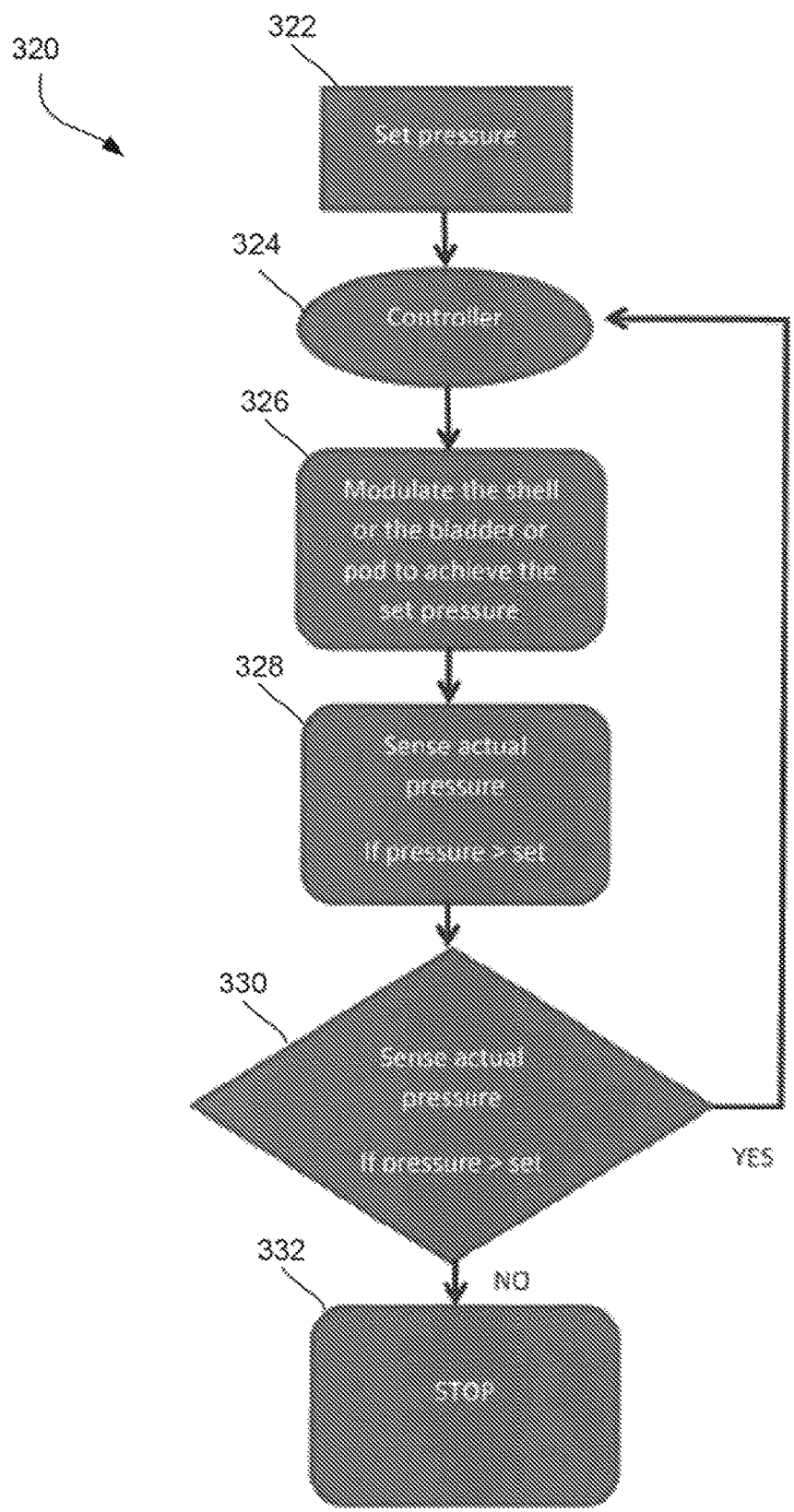
FIG. 33 shows an algorithm for a self-adjusting system which can be implemented to any of the shell assemblies, bladder assemblies, or pods.

A typical algorithm 320 for a self-adjusting system which may be implemented to any of the shell assemblies described herein is illustrated in FIG. 33. The algorithm can use feedback from the pressure sensors or force sensors embedded throughout the assembly or the algorithm can take feedback from other parameters such as temperature, humidity, heart rate or breathing rate of the patient.

Generally, the pressure limits may initially set 322 and programmed in the controller 324. The outer shell assembly 120 or bladder assembly 140 (or pods 316 as previously described) may be modulated or adjusted to initially achieve the set pressure levels 326 when the outer shell assembly 120 is first conformed to the patient body. Once the assembly 120 has been secured to the patient, the actual pressure from the patient upon the assembly may be sensed and monitored 328. If the pressure in one or more areas of the assembly is detected by the sensors as being higher than the set pressure level 330, then the controller 324 (in communication with the sensors) may send a signal to the one or more pumps or regulators 314 adjust the pressure levels against the patient body by adjusting the outer shell assembly 120, bladder assembly 140, or pods 316 individually or collectively. Otherwise, if the monitored pressure levels remain below the set pressure level, then no adjustments may be needed 332 unless or until the sensed pressure levels rise above the preset pressure levels.

Figure 34:
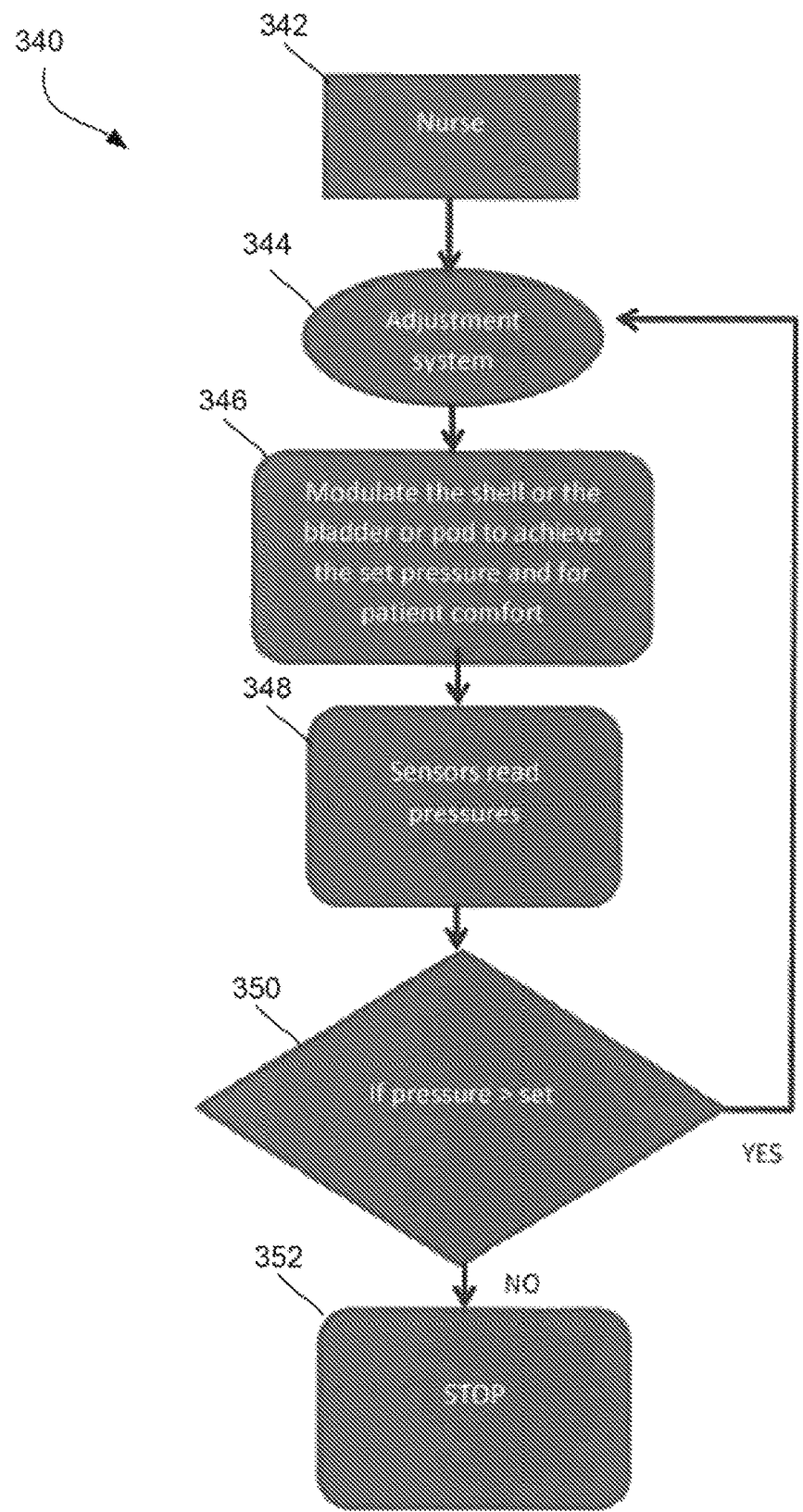
FIG. 34 shows another algorithm for a semi-automatic adjustable system.

In an alternative variation, FIG. 34 illustrates another algorithm 340 in which the outer shell assembly 120, bladder assembly 140, or pods 316 are adjustable semi-automatically, e.g., by a nurse or caretaker. Here, the nurse or caretaker 342 may set an initial pressure level 344 and modulate or adjust the outer shell assembly 120, bladder assembly 140, or pods 316 against the patient body based in part on patient comfort 346. Once the device is suitably secured to the patient, the pressure sensors may monitor or sense the actual pressures imparted by the patient against the device 348. If the sensed pressure is determined to be greater than the level set by the nurse or caretaker 350, the outer shell assembly 120, bladder assembly 140, or pods 316 (individually or collectively) may automatically adjust as described above. Otherwise, an alert, indication, or message may be displayed visually and/or audibly to the nurse to caretaker that the outer shell assembly 120, bladder assembly 140, or pods 316 should be adjusted to bring the sensed pressure levels below the preset values. If the nurse or caretaker does adjust any one or all of the components, then the sensed or detected pressure values may be monitored and displayed or indicated accordingly until the pressure levels fall below their preset levels, in which case any further adjustments may be stopped 352.

In any of the variations described herein, the system can be pre-programmed to alternate pressures by adjusting the stiffness of the bladder assembly 140 by the inflation and/or deflation of different pods as individual elements or collectively as a group. Alternatively, different regions of the outer shell assembly 120 and/or bladder assembly 140 can be divided into different zones in which the pressure can be alternated independently, as previously described. In yet other variations, the fluid within the bladder assembly 140 may be continuously circulated at a predetermined rate to cause turbulence in the fluid. This turbulence leads to lower pressures. In another variation, small silicone or glass beads can be filled inside of the bladder assembly 140 and the fluid can be circulated continuously which causes the beads to float or move leading to lower pressures in the target anatomy.

In yet other variations, particular regions of system (e.g., outer shell assembly 120, bladder assembly 140, or pods 316) may be programmed by the controller to alternate the set pressure level to provide pressure relief against the patient body. For instance, certain zones may be alternated below a set pressure (e.g., 30 mmHg, 20 mmHg, 10 mmHg, etc.) for predetermined periods of time. The controller can take inputs relating to the patient's biometric information such as the height, weight and other parameters and the predetermined time intervals also can be determined to be a function of the rate of perfusion. This alternating feature may be implemented in any of the variations of the system described herein.

In yet other variations, the system may be programmed to simulate a rocking motion or other periodic motion upon the patient body. The periodic rocking or movement may be imparted upon the patient body to allow for pressure reduction and better perfusion rates along the contacted regions of the body. Moreover, this rocking motion can be achieved, e.g., by movement of the rails, supports, etc., or by vibration of particular regions of system (e.g., outer shell assembly 120, bladder assembly 140, or pods 316), as also described above. The vibrating or rocking feature may be actuated based on a number of different criteria. For instance, it may be initiated by a controller periodically based on a set time interval or it may manually initiated by the caretaker or directly by the patient. Alternatively, the controller may be programmed to initiate the motion based on external feedback such as patient inactivity over a particular time period, camera feedback, etc. Additionally, such a feature may also be implemented in any of the variations of the system described herein.

In yet other variations, the sensor may be configured as an indicator for detecting whether any region of the bladder assembly 140 and/or pods 316 are bottoming-out. Hence, one or more of the sensors can be configured to give an indication or feedback on whether any of the bladder assemblies and/or pods have compressed and completely displaced the fluid beneath the patient body which may lead to high pressures. Sensing of bottoming-out can be done, for example, by calculating the difference in pressure readings from pressure sensors that measure the pressure inside the bladder assembly 140 and/or pods 316 when they are not bottoming out, but which would measure patient contact pressure when the patient did bottom out.

Figure 35:
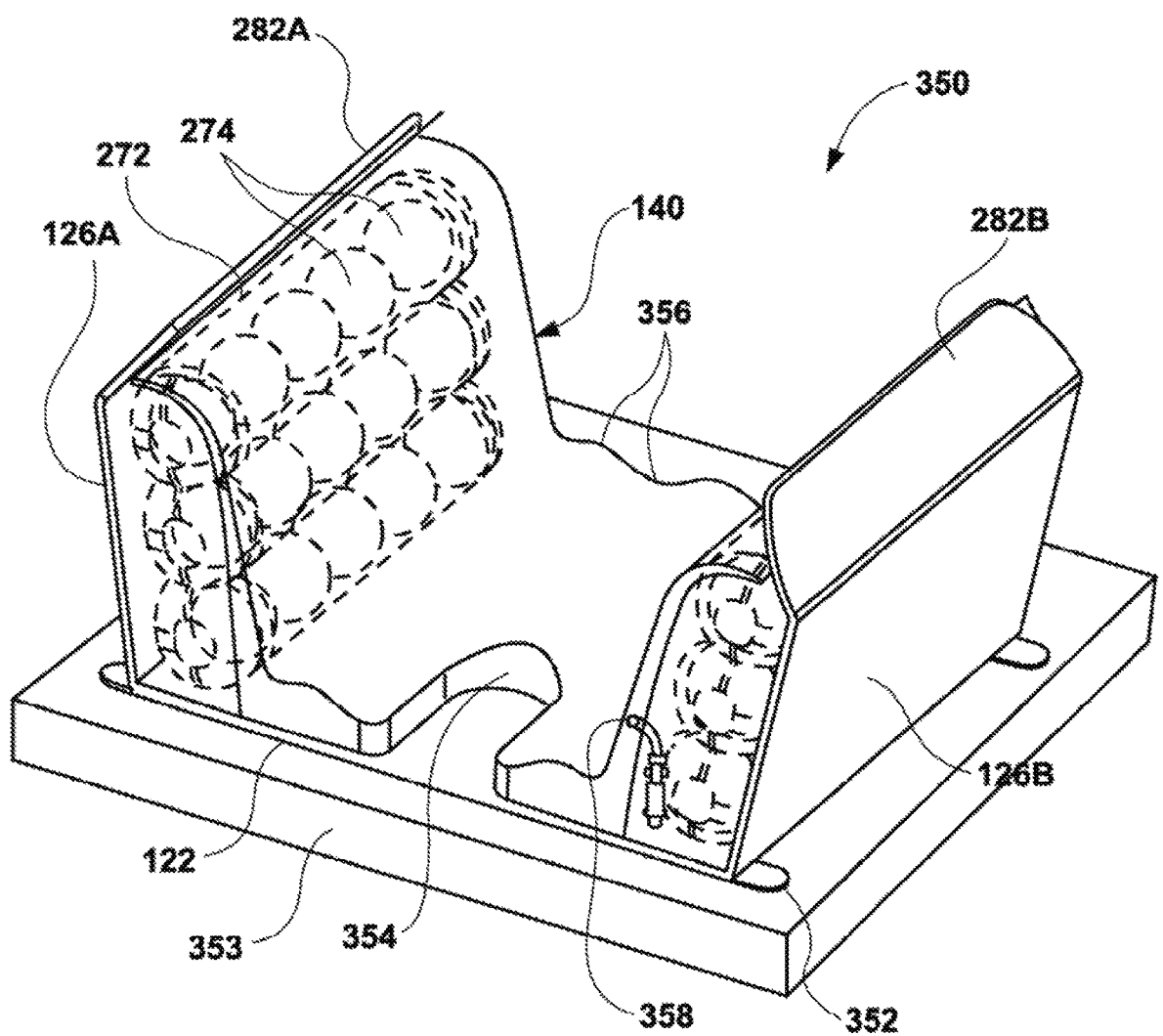
FIG. 35 shows a perspective view of a wheelchair cushion assembly.

FIG. 35 illustrates a wheelchair cushion assembly 350 according to the invention. The wheelchair cushion assembly 350 includes one or more central support sections 122A, 122B, support sections 126A, 126B, bladder assembly 140, retaining lip or portions 282A, 282B, inner pads 272, a plurality of pods 274, and retaining lips or portions 282A, 282B. These components of the wheelchair cushion assembly 350 function in a similar manner to the corresponding components in other embodiments described in this application. The wheelchair cushion assembly 350 further comprises attachment plates or straps 352 that secure the central support section to a wheelchair (not shown). The wheelchair design can also include a lower cushioning layer 353. The lower cushioning layer 353 can have a thickness of 1 to 15 cm and can comprise compressible material such as foam, gels, or oils. The lower cushioning layer 353 may comprise a plurality of springs. The bladder assembly 140 comprises ergonomic contouring 354 and 356 that better shape the cushion to the patient. Ergonomic contouring may be a recessed 356 or cutout 354 portion of the bladder that helps to improve the stability of the patient while maintaining or improving the distribution of pressure on the patient. The wheelchair cushion assembly 350 further comprises a fill port 358 that can be connected to a pump to manually or automatically adjust the pressure of fluid within the bladder assembly 140 and/or within the inner pads 272, independently or in combination.

Stability and pressure are two important aspects of a wheelchair seat cushion assembly. The plurality of pods 274 provide stability for those patients who are lighter than average while still providing some cushioning. For those patients who are heavier than average, the plurality of pods 274 provides cushion and the compliant inner pads 272 are configured to provide a larger spring constant when the extension of the pods exceeds a certain threshold. Additionally, as the plurality of pods 274 are compressed and expanded, the fluid in the sealed bladder assembly 140 can be configured such that the liquid is forced to migrate to the areas without pods which increases the relative pressure on the portions of the patient's anatomy not cushioned directly by the plurality of pods 274. The inner pads 272 can be attached to the bladder assembly 140 or attached to each other within the bladder assembly 140 to provide additional stability to the patient when seated on the wheelchair cushion assembly 350.

Figure 36A:
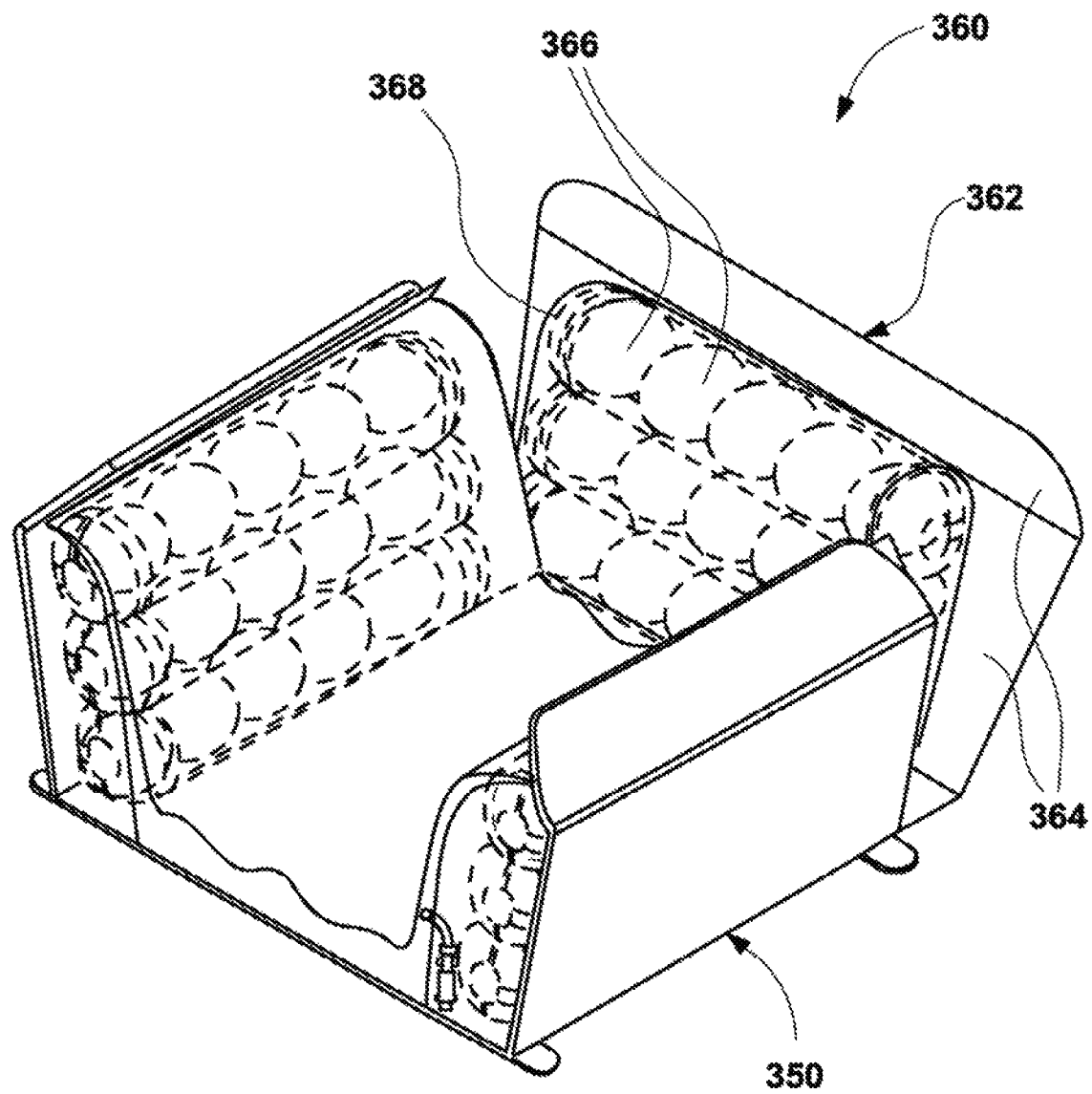
FIG. 36A shows a perspective view of a wheelchair cushion assembly with a cushioning back support.

FIG. 36A shows an enhancement of the wheelchair cushion assembly 350. In this embodiment, a back support 362 is attached to (or deposed adjacent to) the wheelchair cushion assembly 350 to form a wheelchair cushion assembly with back support 360 that provides improved pressure distribution for the patient's seat and back regions relative to the wheelchair cushion assembly 350. The back support 362 may comprise back support portions 364, a plurality of back pods 366, and inner back pads 368. The addition of the back support 362 allows additional pressure distribution within the bladder assembly 140 as additional pressure from the seat area is redistributed to the back portion of the assembly 360.

Figure 36B:
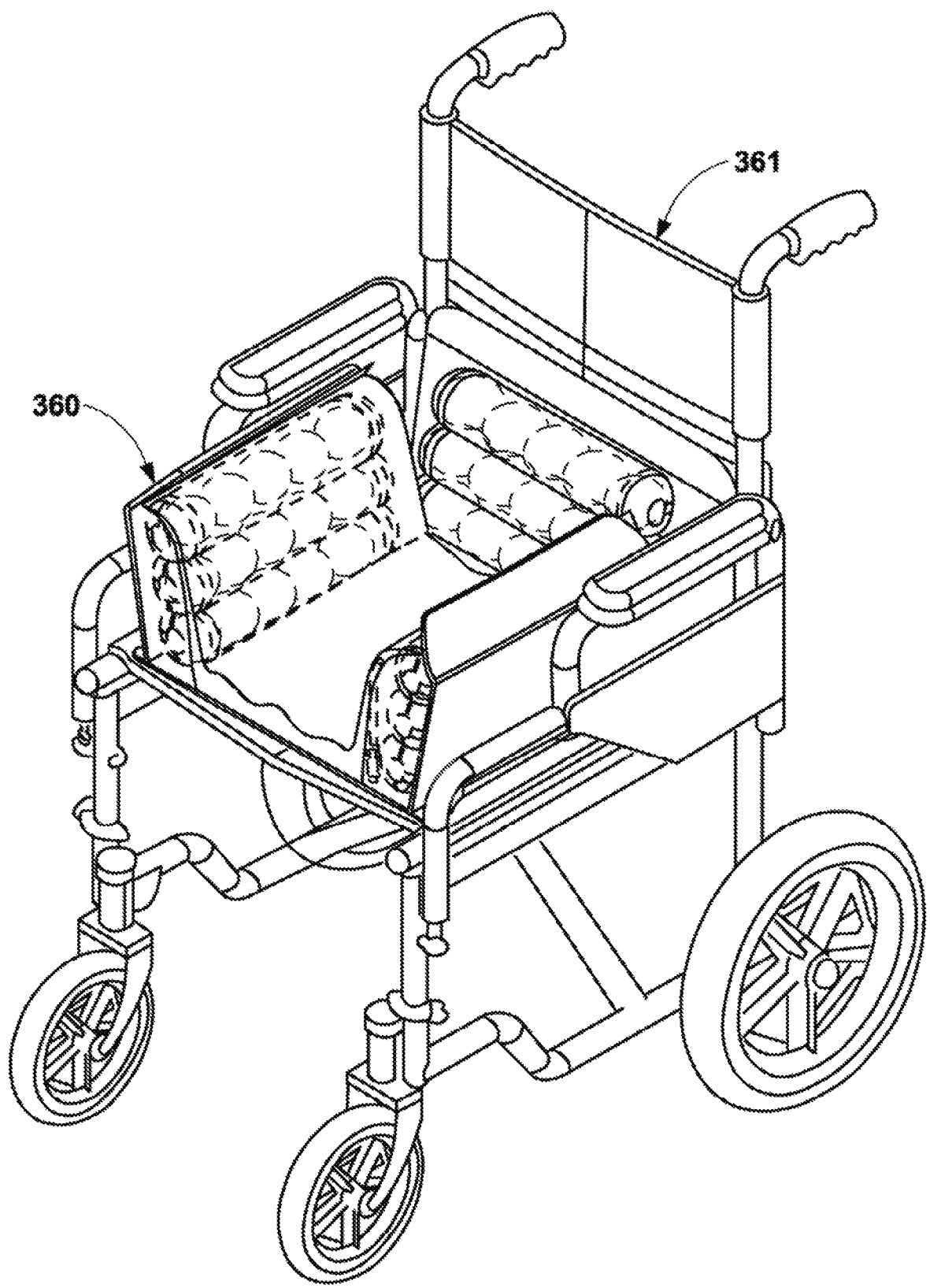
FIG. 36B shows a perspective view of this assembly disposed upon a wheelchair.

As shown in FIG. 36B, the wheelchair cushion assembly 350 or wheelchair cushion assembly with back support 360 can be disposed onto a wheelchair 361. The assembly 350 or 360 can be resting on the wheelchair 361 or firmly attached via screws, bolts, straps, or other attachment means that attach, permanently or temporarily, the wheelchair 361 to the attachment plates or straps 352 (as shown in FIG. 35).

Adjustable support assemblies according to the invention can be integrated into a mattress or can be an accessory to a standard mattress. FIGS. 37, 38, 39A, and 39B show examples of such embodiments. Adjustable support assemblies may sit on top of the mattress or sit in a recess of the mattress that is specifically designed for the support structure. A plurality of support regions may be positioned to provide independently adjustable support for two or more of the following regions of the body a person who would lie upon the mattress with support structure disposed upon it, e.g., pelvic region, ischium region, head, feet, heels, torso, shoulders, and/or elbow, etc.

Figure 37:
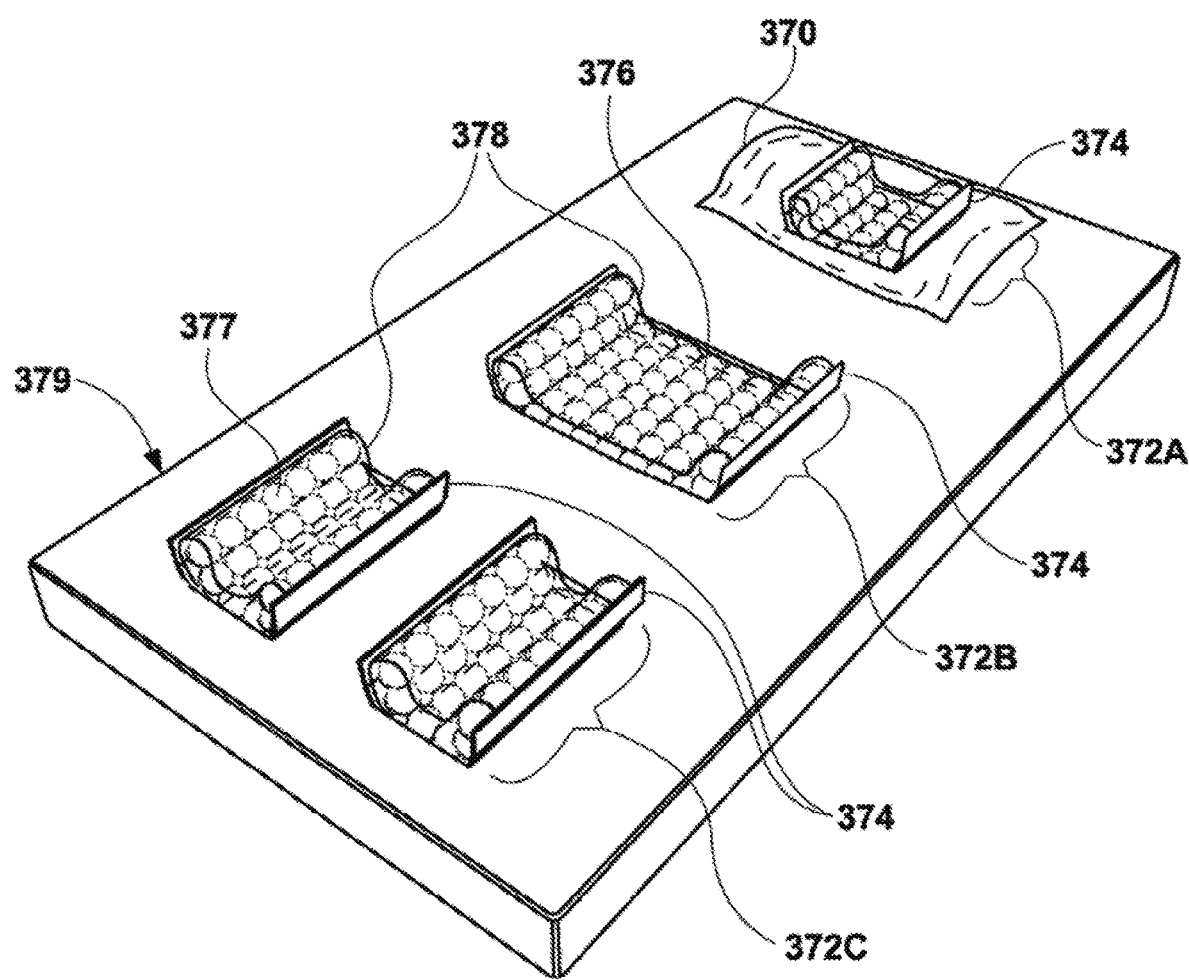
FIGS. 37 and 38 show perspective views of cushion assemblies disposed upon a mattress according to exemplary embodiments of the invention.

FIG. 37 shows a plurality of adjustable support assemblies 372A, 372B, and 372C disposed upon a mattress 379. The adjustable support assemblies 372A, 372B, and 372C are shaped to accommodate regions of a patient's anatomy, such as the head (e.g. assembly 372A), pelvis (e.g., assembly 372B), and/or feet (e.g., assemblies 372C). In each case, the individual shaping of adjustable support assemblies to accommodate specific regions of the patient's anatomy allow for better stability by allowing less fluid to be used in a design. This is particularly true when a design is sold to the consumer without expensive customization for individual sizing and fitting. A conformal pillow 370 may be built into the mattress to allow further support for the patient's head.

Figure 38:
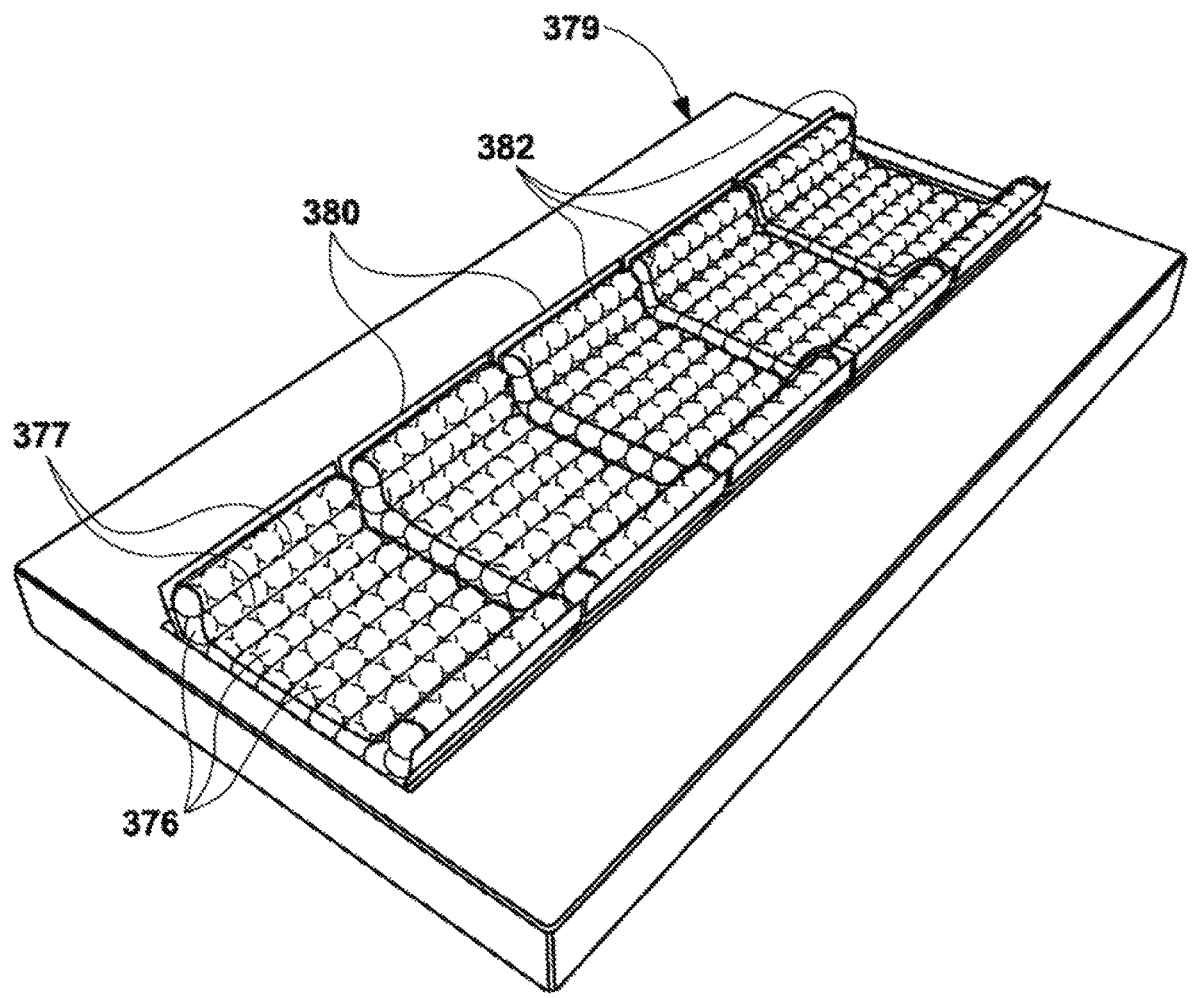

Since regular repositioning of the patient is an important aspect of the prevention of pressure ulcers in bed-restricted patients, mattress geometries that allow easily multiple different configurations to accommodate different positions are desirable. FIG. 38 shows one such configuration. This configuration likely requires slightly more fluid than the embodiment illustrated in FIG. 37, but it allows for increased flexibility in the ways in which the patient can be positioned. In FIG. 38, a plurality of adjustable support assembly segments runs nearly the length of the bed. These adjustable support assembly segments each comprise a segmented adjustable support portion 380 and segmented bladder assembly 382. Five segments are depicted in FIG. 38. In other embodiments, 3 to 100 segments could be used.

Figure 39A:
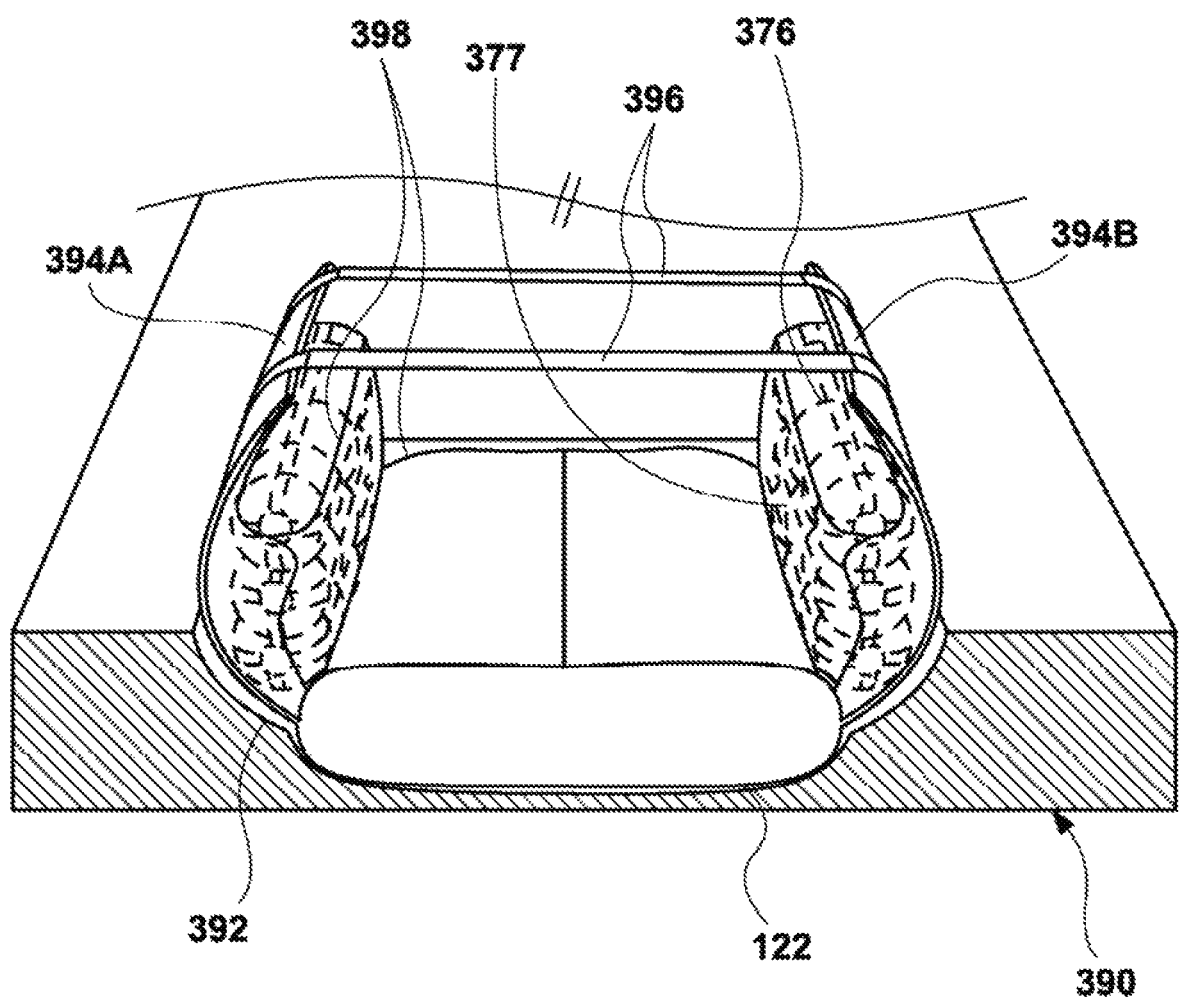
FIGS. 39A and 39B show perspective views of exemplary cross sections of cushion assemblies disposed upon a mattress with recessed cutouts according to exemplary embodiments of the invention.
Figure 39B:
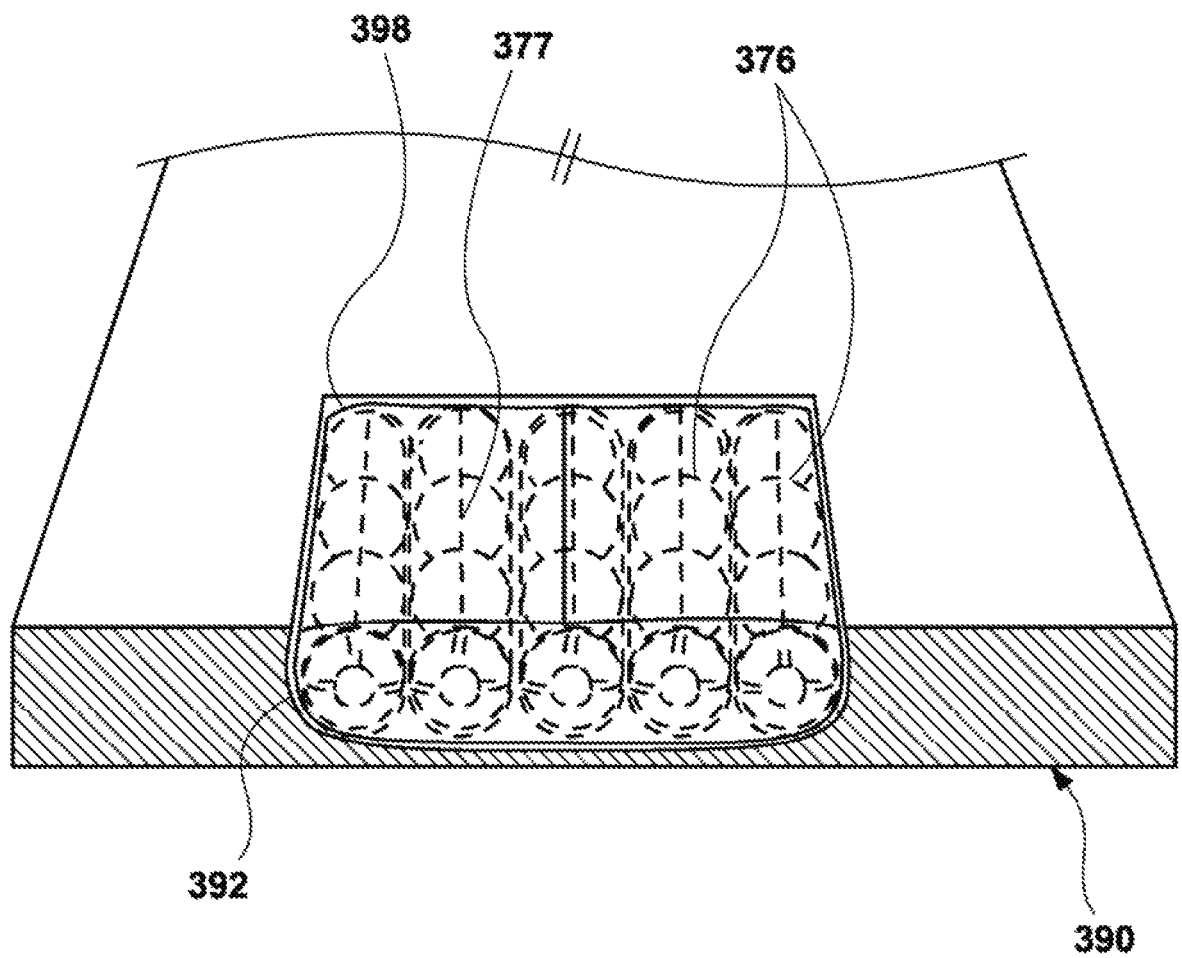

Exemplary cross sections of the embodiments of FIGS. 37 and 38 are shown in the perspective views of FIGS. 39A and 39B. In the embodiments shown in FIGS. 37 and 38, the mattress 379 is intended to be a mattress with a flat top. FIGS. 39A and 39B illustrate slightly variations in which a recessed mattress 390 is used.

In embodiments shown in FIGS. 37, 38, 39A, and 39B, the individual adjustable support assemblies 372A, 372B, and 372C or segmented adjustable support sections 380 each comprise a plurality of pods 376, which are contained within a plurality of inner pads 377. The plurality of inner pads is contained within or disposed upon a bladder assembly 378. The plurality of pods 376, inner pads 377, and bladder assembly 378 components are supported by support portions 374 and each of these components functions in a similar manner to the corresponding components in other embodiments described in this application. The adjustable support assemblies are disposed on a mattress 379 or on a recessed mattress 390. The adjustable support assemblies may be attached to a mattress by a manufacturer or may be a separate assembly that is placed on a mattress by the user or caregiver. The recessed contour 392 in the recessed mattress 390 provides additional stability for the patient because it restricts the movement of an adjustable support assembly relative to the recessed mattress 390. The recess contour 392 may provide additional support for the adjustable support portions 394 as shown in FIG. 39A or may serve in place of the adjustable support portions 394 as shown in FIG. 39B. One advantage of the configuration shown in FIG. 39B is that the top of the mattress can be flat, which allows the use of normal bedding materials.

In FIGS. 37, 38, and 39A, the support portions 374 and 394, can be configured such that they can be moved, by the patient or a caregiver, into a flat position or laterally inward or outward, which can make it easier for the patient to get into and out of the bed.

The mattress 379 or recessed mattress 390 may be of many different types. For example, a spring mattress, a foam mattress, a low air loss mattress, a segmented air mattress, a cyclical air pressure mattress, a water bed, or a bed of air supported glass beads may be used.

Figure 40A:
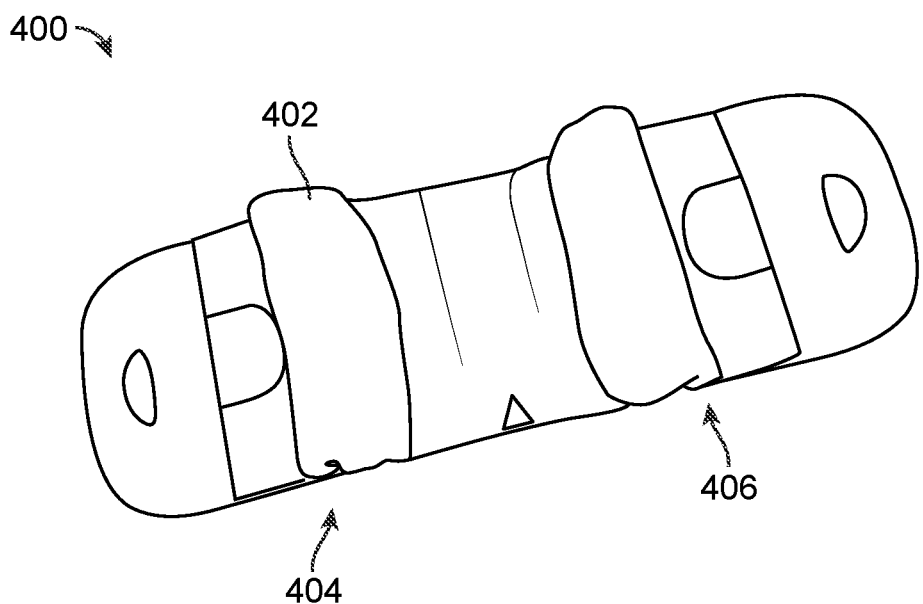
FIGS. 40A and 40B show perspective views of another support assembly variation having separated support portions for unrestricted adjustability along the sides of a patient body.

In yet another variation, FIG. 40A shows an assembly which may utilize a support which may be independent of one another so as to allow for unrestricted adjustability relative to the sides of a patient's body. Generally, the support assembly 400 may have arm outer pad assembly 402 which is positionable partially or entirely over or upon a first support portion 404 and a second support portion 406 which is adjustably apposed to the first support portion 404. Adjusting a position of the first support portion 404 and the second support portion 406 may allow for the outer pad 402 to be adjusted in for optimizing the support provided against the sides of (and beneath) the patient's body.

Figure 40B:
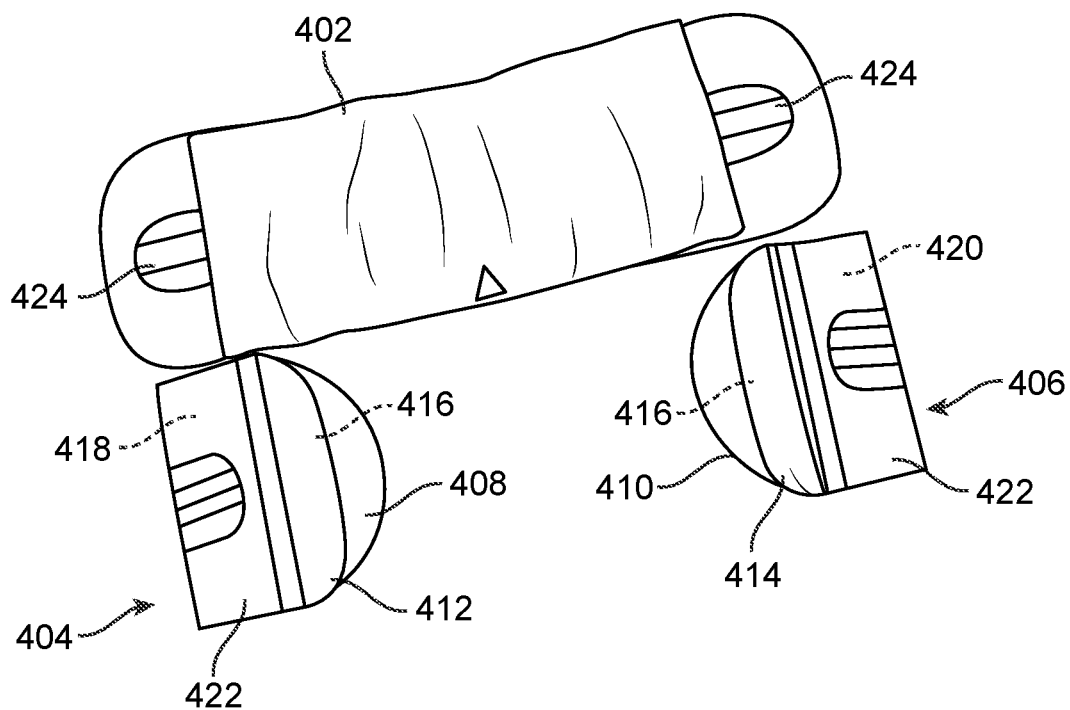

FIG. 40B shows a perspective assembly view of some of the components of the support assembly 400. The outer pad 402, as described in further detail below, may generally comprise a fluid or gas filled layer embodied in any of the variations described above. The first support assembly 404 may generally comprise a support platform 408 upon which a first conforming support member 418 may be secured. The conforming support 418 may be comprised of a relatively soft material such as foam which may be shaped into various sizes and covered in a soft, breathable, and stretchable covering 422 which may be optionally water resistant and anti-bacterial (e.g., Gore-Tex®, BrookWood's Derma Plush®, Eastex Fabrics Tek Stretch). In either case, the conforming support 418 may be secured upon the first support platform 408 and define a surface upon which the one or more pods 416 may be positioned linearly adjacent to one another for placement against the patient's side. The one or more pods 416 may be enclosed by an inner layer or pad 412 which may enclose the one or more pods 416 and, as previously described, the inner layer or pad 412 may be devoid of fluid and constrain the expansion of the individual pods. Optionally, inner layer or pad 412 may be optionally vented to allow for any trapped air to vent from between the pods 416 when the pods 416 undergo compression when placed against the patient's body.

Likewise, the second support assembly 406 may be similarly constructed of a support platform 410 upon which a second conforming support member 420 may be covered in covering 422. The support member 420 may be configured for likewise present a surface upon which the one or more pods 416 may be aligned and enclosed by inner layer or pad 414.

Figure 41A:
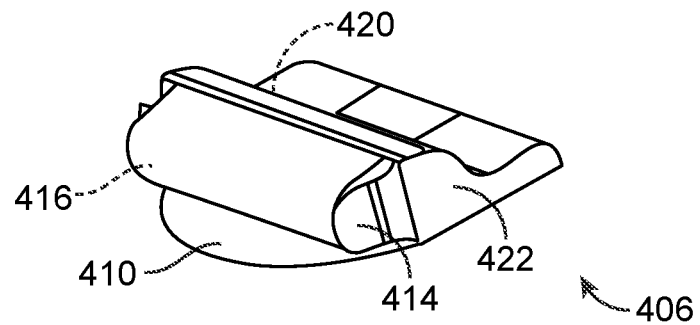
FIGS. 41A to 41B show perspective views of the components of the adjustable support portions.
Figure 41B:
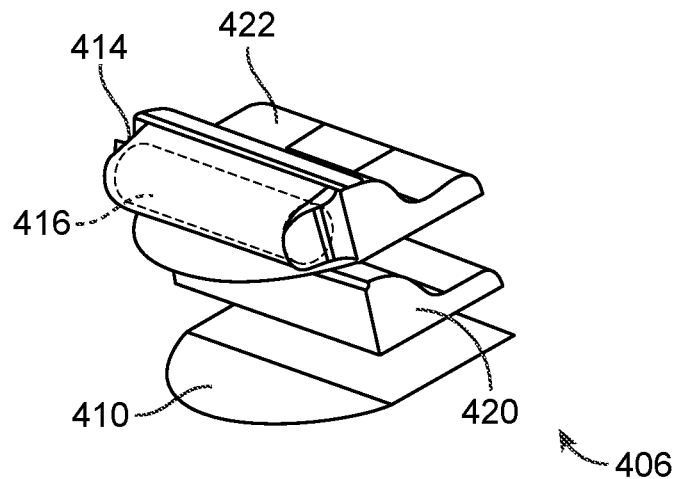
Figure 41C:
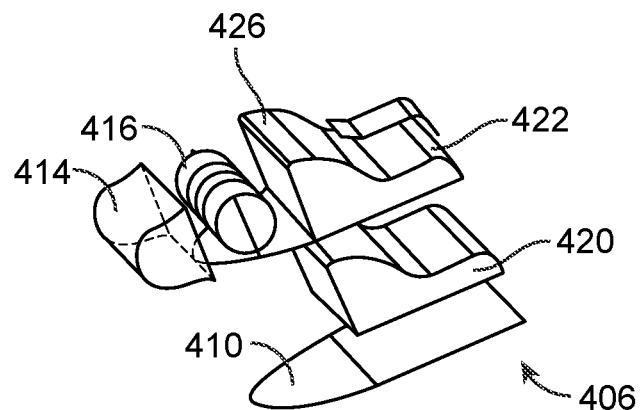

As illustrated in the perspective views of FIGS. 41A to 41C, the second support assembly 406 is shown where the conforming support member 420 may be shaped into a tapered support which presents a transverse or angled surface upon which the inner layer or pad 414 may be attached. The one or more pods 416 may be aligned (shown in this example as five fluid pods although fewer than five or greater than five pods may be used) against this presentation surface and constrained by the inner layer or pad 414. As previously described, the inner layer or pad 414 may be devoid of fluid but instead constrain the expansion of the individual pods 416. The entire inner layer or pad 414 and the pods 416 constrained within may be covered by a fabric covering, as described above. The shapes of the support member 420 as well as platform 410 may be varied depending upon the desired design and conformability against the side of the patient's body.

Optionally, a securement strip 426 (e.g., hook-loop fastener strip) may also be provided along the covering 422 or support member 420 for securing the support assemblies and outer pad 402 to one another.

Figure 42A:
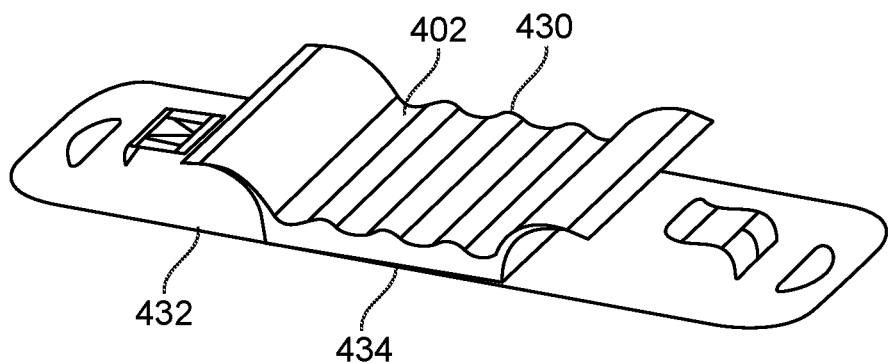
FIGS. 42A and 42B show perspective views of the outer pad assembly.
Figure 42B:
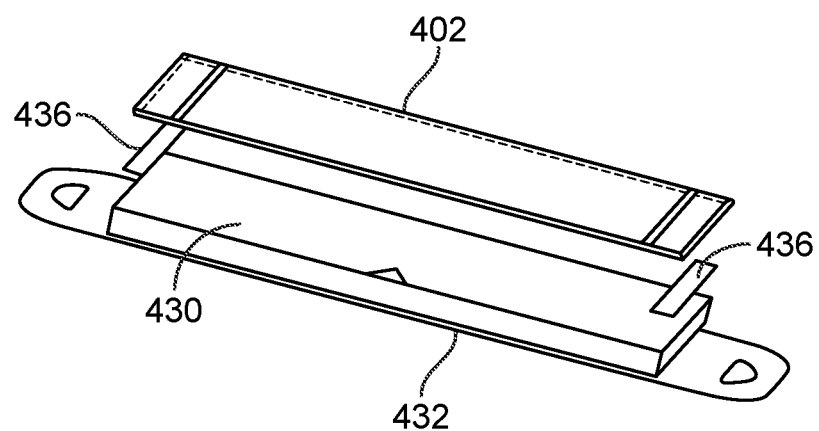

Turning now to the outer pad 402, FIGS. 42A and 42B show perspective views of the assembly. This particular variation of the outer pad 402 may optionally incorporate the pods along portions of the pad or throughout the entire pad if so desired. In this example, the pods are omitted but the outer pad 402 be a continuous bladder filled with any number of fluids or gases (or both) through the entire layer as previously described above (e.g., mineral oil or any other similar low density fluids, water, mixture of water or oil, additional microspheres or beads in composition with the water, oil, or both to create a composite low density fluid mixture, etc.). The outer pad 402 may be sized to have different lengths (e.g., 28 inches although pad 402 may be shorter or longer, for example, to extend across the width of a bed) so long as the outer pad 402 is sufficiently long enough to provide support beneath the patient's body when positioned upon the supports 404, 406 as described above. The outer pad 402 may be situated upon the supports 404, 406 such that the pressure from the patient's body may be transferred between the outer pad 402 and pods 416 and through the inner layer or pad 412, 414.

The outer pad 402 may be optionally secured and enclosed within a covering 430 which may be a soft, breathable, and stretchable covering as described above. Moreover, the covering 430 (and/or outer pad 402) may be secured to a support layer 432 which may be comprised of a fabric layer (which may be non-stretching). The covering 430 may also include micro-climate management layers (eg. thinsulate, primaloft or similar insulating fabrics). The covering 430 may be optionally attached (removably or permanently) along the entire length of the support layer 432 or the covering 430 may be attached alternatively along a central portion 434.

Additionally and/or optionally, the outer pad 402 may also incorporate one or more securement strips 436 (e.g., hook-loop fastener strip) for corresponding attachment to the securement strips 426 positioned along supports 404, 406. Moreover, it is intended that any of the materials or components may be incorporated into the adjustable variation. For instance any of the controllers, one or more pressure sensors, and/or actuators described above may be fully incorporated into, upon, or within any of the layers, pads, or the support portions 404,406 if so desired.

The applications of the devices and methods discussed above are not limited to particular regions of the body such as the sacrum, trochanter, heel, etc. but may include any number of further applications. Modification of the above-described device and methods for carrying out the invention, and variations of aspects of the invention that are obvious to those of skill in the art are intended to be within the scope of the claims.

What is claimed is:

1. A support assembly, comprising:
   fluid-filled pods;
   a first compliant inner layer and a second compliant inner layer each enclosing two or more adjacent fluid-filled pods selected from the fluid-filled pods whereby the first and second compliant inner layers restrict the expansion of the respective two or more adjacent fluid-filled pods;
   a first support portion having a first conforming support member and a second support portion, having a second conforming support member wherein the first and second support portions each have a first end and a second end, wherein at least one of the fluid-filled pods of the two or more adjacent fluid-filled pods enclosed in the first compliant inner layer is between the first end and the second end of the first support portion, wherein at least one of the fluid filled-pods of the two or more adjacent fluid-filled pods enclosed in the second compliant inner layer is between the first end and the second end of the second support portion, wherein the first and second ends of the first support portion are adjustably positionable in a lateral direction relative to the first and second ends of the second support portion, wherein the first conforming support member is attached to the first compliant inner layer and the second conforming support member is attached to the second compliant inner layer such that the first and second compliant inner layers are apposed to one another;
   a fluid-filled outer layer positioned upon at least the first and second compliant inner layers such that pressure is transferable therebetween.

2. The support assembly of claim 1 wherein the fluid-filled outer layer is configured to support a sacrum of a patient positioned upon the support assembly.

3. The support assembly of claim 1 wherein the fluid-filled pods contains a gas.

4. The support assembly of claim 1 wherein the fluid-filled pods further comprise beads.

5. The support assembly of claim 1 wherein the first and second compliant inner layers are vented.

6. The support assembly of claim 1 wherein the first and second support portions are comprised of a foam material.

7. The support assembly of claim 1 wherein one or more pressure sensors are positioned upon or within the support assembly to sense a first pressure.

8. The support assembly of claim 7 further comprising:
   a controller; and
   an actuator, wherein the controller calculates a pressure difference between the first pressure and a second pressure and controls the actuator to adjust a force applied to the support assembly in response to the pressure difference.

9. The support assembly of claim 1 further comprising a pump fluidly coupled to the support assembly to increase or decrease a volume of fluid.

10. The support assembly of claim 9 wherein the pump is configured to selectively direct fluid to at least one of the fluid-filled pods based on a sensed pressure.

11. The support assembly of claim 1 wherein the support assembly is integrated into a piece of furniture or platform on which a subject sits, lies, or stands.

12. The support assembly of claim 1 wherein the support assembly further comprises one or more heating or cooling elements.

13. The support assembly of claim 1 wherein the first and second compliant inner layers are attached to their respective first and second support portions such that adjustment of the first or second support portions moves the respective first or second compliant inner layers and fluid-filled pods in a corresponding manner.

14. The support assembly of claim 1, wherein the first support portion and the second support portion are positionable along a plane, and wherein at least a portion of each of the first and second ends is simultaneously positionable along the plane.

15. The support assembly of claim 1, wherein the first support portion is positionable on a plane such that at least a portion of the first and second ends of the first support portion and a portion between the first and second ends are simultaneously positionable on the plane, and wherein the second support portion is positionable on the plane such that at least a portion of the first and second ends of the second support portion and a portion between the first and second ends are simultaneously positionable on the plane.

16. The support assembly of claim 1 wherein the first support portion is separable from the second support portion.

17. A support assembly, comprising:
   a first support portion and a second support portion, each support portion including:
      fluid-filled pods;
      a compliant inner layer enclosing the fluid-filled pods; and wherein the fluid-filled pods of the first support portion are laterally adjustably positionable relative to the fluid-filled pods of the second support portion, and a fluid-filled outer layer positioned upon the compliant inner layer of the first support and upon the compliant inner layer of the second support portion such that the pressure is transferable therebetween.

* * * * *